(12) United States Patent
Kim

(10) Patent No.: US 12,076,269 B2
(45) Date of Patent: *Sep. 3, 2024

(54) HAND-HELD CRYOTHERAPY DEVICE INCLUDING CRYOGEN TEMPERATURE PRESSURE CONTROLLER AND METHOD THEREOF

(71) Applicant: RECENSMEDICAL, INC., Ulsan (KR)

(72) Inventor: Gun-Ho Kim, Ulsan (KR)

(73) Assignee: RecensMedical, Inc., Ulsan (KR)

( * ) Notice: Subject to any disclaimer, the term of this patent is extended or adjusted under 35 U.S.C. 154(b) by 755 days.

This patent is subject to a terminal disclaimer.

(21) Appl. No.: 17/223,860

(22) Filed: Apr. 6, 2021

(65) Prior Publication Data

US 2021/0220164 A1  Jul. 22, 2021

Related U.S. Application Data

(63) Continuation of application No. 17/036,311, filed on Sep. 29, 2020, now Pat. No. 10,993,827, which is a
(Continued)

(30) Foreign Application Priority Data

| Apr. 27, 2018 | (KR) | 10-2018-0049110 |
| Dec. 7, 2018 | (KR) | 10-2018-0157478 |
| Mar. 8, 2019 | (KR) | 10-2019-0027184 |

(51) Int. Cl.
*A61F 7/00* (2006.01)
*A61M 19/00* (2006.01)

(52) U.S. Cl.
CPC ............. *A61F 7/00* (2013.01); *A61F 7/007* (2013.01); *A61F 7/0085* (2013.01); *A61M 19/00* (2013.01);
(Continued)

(58) Field of Classification Search
CPC ...... A61B 18/0218; A61B 2018/00065; A61B 2018/00101; A61B 2018/00452;
(Continued)

(56) References Cited

U.S. PATENT DOCUMENTS

| 2,044,823 A | 6/1936 | Whiteside |
| 4,412,538 A | 11/1983 | Yamauchi et al. |

(Continued)

FOREIGN PATENT DOCUMENTS

| CN | 2660834 Y | 12/2004 |
| EP | 1 030 611 B1 | 9/2004 |

(Continued)

OTHER PUBLICATIONS

Chinese First Office Action dated Dec. 22, 2020 for CN 201780083128.0.
(Continued)

*Primary Examiner* — Tigist S Demie
(74) *Attorney, Agent, or Firm* — Knobbe, Martens, Olson & Bear, LLP

(57) ABSTRACT

This application relates to a hand-held cooling device for supplying a cryogen to a target region for cryotherapy. The device can include a cryogen container configured to contain a first cryogen having a first temperature and a nozzle configured to spray a first modified cryogen to the target region, the first modified cryogen having a second temperature higher than the first temperature. The device can also include a cryogen temperature regulator configured to receive the first cryogen and output the first modified cryogen to the nozzle, the cryogen temperature regulator disposed closer to the nozzle than the cryogen container. The cryogen temperature regulator can include a holder tube, a porous structure disposed inside a holder tube and a heater disposed around the holder tube and heating the holder tube
(Continued)

so as to increase the first temperature to the second temperature while the first cryogen passes through the porous structure.

20 Claims, 47 Drawing Sheets

Related U.S. Application Data continuation of application No. PCT/KR2019/005105, filed on Apr. 26, 2019.

(52) U.S. Cl.
CPC .............. *A61F 2007/0004* (2013.01); *A61F 2007/0058* (2013.01); *A61F 2007/0063* (2013.01); *A61F 2007/0064* (2013.01); *A61F 2007/0068* (2013.01); *A61F 2007/0086* (2013.01); *A61F 2007/0087* (2013.01); *A61M 2205/3653* (2013.01)

(58) Field of Classification Search
CPC ........... A61B 2018/00744; A61B 2018/00791; A61B 2018/0237; A61F 2007/0004; A61F 2007/0058; A61F 2007/0063; A61F 2007/0064; A61F 2007/0068; A61F 2007/0086; A61F 2007/0087; A61F 7/00; A61F 7/007; A61F 7/0085; A61F 9/00; A61M 11/00; A61M 19/00; A61M 2202/03; A61M 2205/3313; A61M 2205/3368; A61M 2205/3393; A61M 2205/3606; A61M 2205/3633; A61M 2205/3653; A61M 2205/3673; A61M 2205/7536; A61M 2205/7545; A61M 2205/8206; A61M 2205/8225; A61M 2209/084; A61M 2210/04; A61M 2210/0612

See application file for complete search history.

(56) References Cited

U.S. PATENT DOCUMENTS

| | | | |
|---|---|---|---|
| 4,646,735 A | 3/1987 | Seney |
| 5,653,113 A | 8/1997 | Sawano |
| 5,979,454 A | 11/1999 | Anvari et al. |
| 6,099,521 A | 8/2000 | Shadduck |
| 6,141,985 A | 11/2000 | Cluzeau et al. |
| 6,226,996 B1 | 5/2001 | Weber et al. |
| 6,632,219 B1 | 10/2003 | Baranov et al. |
| 6,669,688 B2 | 12/2003 | Svaasand et al. |
| 7,037,326 B2 | 5/2006 | Lee |
| 7,780,656 B2 | 8/2010 | Tankovich |
| 7,963,959 B2 | 6/2011 | Silva et al. |
| 8,083,734 B2 | 12/2011 | Steinfatt et al. |
| D658,775 S | 5/2012 | Jiangminhui |
| 8,177,827 B2 | 5/2012 | Shapiro |
| 8,256,233 B2 | 9/2012 | Boyden et al. |
| 8,409,184 B2 | 4/2013 | Baust et al. |
| 8,652,131 B2 | 2/2014 | Muller et al. |
| 8,672,879 B2 | 3/2014 | Grant et al. |
| 8,747,397 B2 | 6/2014 | Baust et al. |
| 8,788,060 B2 | 7/2014 | Nebrigic et al. |
| 8,858,583 B2 | 10/2014 | Shtram et al. |
| 9,017,318 B2 | 4/2015 | Fourkas et al. |
| 9,039,688 B2 | 5/2015 | Palmer, III et al. |
| 9,066,712 B2 | 6/2015 | Fourkas et al. |
| 9,113,855 B2 | 8/2015 | Burger et al. |
| 9,155,584 B2 | 10/2015 | Fourkas et al. |
| 9,398,975 B2 | 7/2016 | Müller et al. |
| 9,522,031 B2 | 12/2016 | Anderson et al. |
| 9,549,773 B2 | 1/2017 | Anderson et al. |
| 9,642,741 B2 | 5/2017 | Feng et al. |
| 9,801,677 B2 | 10/2017 | Anderson et al. |
| 9,855,166 B2 | 1/2018 | Anderson et al. |
| 9,956,355 B2 | 5/2018 | Besirli et al. |
| 9,974,684 B2 | 5/2018 | Anderson et al. |
| D822,841 S | 7/2018 | Cheng |
| 10,085,881 B2 | 10/2018 | Karik et al. |
| 10,154,870 B2 | 12/2018 | Ottanelli |
| 10,188,444 B2 | 1/2019 | Fourkas et al. |
| 10,213,244 B2 | 2/2019 | Fourkas et al. |
| 10,322,248 B2 | 6/2019 | Besirli et al. |
| 10,349,997 B1 | 7/2019 | O'Reilly |
| 10,363,080 B2 | 7/2019 | Elkins et al. |
| 10,543,032 B2 | 1/2020 | Babkin et al. |
| 10,993,827 B2 | 5/2021 | Kim |
| 11,154,417 B2 | 10/2021 | Kim |
| 11,207,488 B2 | 12/2021 | Kim |
| 2004/0102768 A1 | 5/2004 | Cluzeau et al. |
| 2004/0111087 A1 | 6/2004 | Stern et al. |
| 2005/0005626 A1 | 1/2005 | McMahon |
| 2005/0059940 A1 | 3/2005 | Weber et al. |
| 2005/0261753 A1 | 11/2005 | Littrup et al. |
| 2006/0200117 A1 | 9/2006 | Hermans |
| 2006/0213509 A1 | 9/2006 | Marin et al. |
| 2007/0005048 A1 | 1/2007 | Niedbala et al. |
| 2008/0164296 A1 | 7/2008 | Shelton et al. |
| 2008/0221561 A1 | 9/2008 | Geiger et al. |
| 2009/0036846 A1 | 2/2009 | Dacquay et al. |
| 2009/0062751 A1 | 3/2009 | Newman, Jr. |
| 2009/0124972 A1 | 5/2009 | Fischer et al. |
| 2009/0149930 A1 | 6/2009 | Schenck |
| 2009/0163902 A1 | 6/2009 | DeLonzor et al. |
| 2009/0171333 A1 | 7/2009 | Hon |
| 2010/0010480 A1 | 1/2010 | Mehta et al. |
| 2010/0087805 A1 | 4/2010 | Citterio et al. |
| 2010/0196343 A1 | 8/2010 | O'Neil et al. |
| 2010/0198207 A1 | 8/2010 | Elkins et al. |
| 2011/0060322 A1 | 3/2011 | Manstein |
| 2011/0072834 A1 | 3/2011 | Ishikura et al. |
| 2011/0098791 A1 | 4/2011 | Kim |
| 2011/0137268 A1 | 6/2011 | Thomason et al. |
| 2011/0152850 A1 | 6/2011 | Niedbala et al. |
| 2011/0177474 A1 | 7/2011 | Jamnia et al. |
| 2011/0224761 A1 | 9/2011 | Manstein |
| 2012/0130458 A1 | 5/2012 | Ryba et al. |
| 2012/0191166 A1 | 7/2012 | Callister et al. |
| 2012/0232549 A1 | 9/2012 | Willyard et al. |
| 2012/0265278 A1 | 10/2012 | Fourkas et al. |
| 2013/0116719 A1 | 5/2013 | Shtram et al. |
| 2013/0184694 A1 | 7/2013 | Fourkas et al. |
| 2013/0296811 A1 | 11/2013 | Bangera et al. |
| 2013/0315924 A1 | 11/2013 | Hsu et al. |
| 2014/0012226 A1 | 1/2014 | Hochman |
| 2014/0200511 A1 | 7/2014 | Boyden et al. |
| 2014/0277023 A1 | 9/2014 | Sekino et al. |
| 2014/0303608 A1 | 10/2014 | Taghizadeh |
| 2015/0051545 A1 | 2/2015 | Henderson et al. |
| 2016/0058488 A1 | 3/2016 | Fourkas et al. |
| 2016/0135864 A1 | 5/2016 | Babkin |
| 2016/0143802 A1 | 5/2016 | Tranfaglia et al. |
| 2016/0183996 A1 | 6/2016 | Burger et al. |
| 2016/0242956 A1 | 8/2016 | Gomez |
| 2016/0262820 A1 | 9/2016 | Allison et al. |
| 2016/0279350 A1 | 9/2016 | Besirli et al. |
| 2017/0014174 A1 | 1/2017 | Levine et al. |
| 2017/0062793 A1 | 3/2017 | Zakharyan et al. |
| 2017/0231816 A1 | 8/2017 | Ryan |
| 2017/0232243 A1 | 8/2017 | Herweijer |
| 2017/0304558 A1 | 10/2017 | Besirli et al. |
| 2017/0354451 A1 | 12/2017 | Marin et al. |
| 2018/0116705 A1 | 5/2018 | Lee et al. |
| 2018/0235805 A1 | 8/2018 | Burger et al. |
| 2018/0310979 A1 | 11/2018 | Peled et al. |
| 2019/0000524 A1 | 1/2019 | Rosen et al. |
| 2019/0015146 A1 | 1/2019 | DuBois et al. |
| 2019/0038459 A1 | 2/2019 | Karnik et al. |
| 2019/0175394 A1 | 6/2019 | Kim |
| 2019/0175395 A1 | 6/2019 | Kim |
| 2019/0175396 A1 | 6/2019 | Kim |

(56) References Cited

U.S. PATENT DOCUMENTS

| | | |
|---|---|---|
| 2019/0239938 A1 | 8/2019 | Kazic et al. |
| 2019/0254866 A1 | 8/2019 | Whiteley et al. |
| 2019/0290881 A1 | 9/2019 | Kim |
| 2020/0054483 A1 | 2/2020 | Kim |
| 2020/0100934 A1 | 4/2020 | Ariano et al. |
| 2020/0309436 A1 | 10/2020 | Kim |
| 2021/0007882 A1 | 1/2021 | Kim |
| 2021/0007883 A1 | 1/2021 | Kim |

FOREIGN PATENT DOCUMENTS

| | | |
|---|---|---|
| EP | 1 401 347 B1 | 8/2011 |
| EP | 2 010 087 B1 | 11/2014 |
| EP | 2 910 276 A1 | 8/2015 |
| EP | 2 759 272 B1 | 11/2018 |
| GB | 1443069 A | 7/1976 |
| GB | 2002236 A | 2/1979 |
| JP | 04-092663 A | 3/1992 |
| JP | 06-086818 A | 3/1994 |
| JP | 10-230435 A | 9/1998 |
| JP | 2002-505155 A | 2/2002 |
| JP | 4049358 B2 | 2/2002 |
| JP | 2004-515270 A | 5/2004 |
| JP | 2005-080832 A | 3/2005 |
| JP | 2008-212638 A | 9/2008 |
| JP | 2008-545462 A | 12/2008 |
| JP | 2009-034273 A | 2/2009 |
| JP | 2009-056320 A | 3/2009 |
| JP | 2011-077314 A | 4/2011 |
| JP | 2012-143279 A | 8/2012 |
| JP | 2013-142410 A | 7/2013 |
| JP | 2014-198238 A | 10/2014 |
| JP | 2015-510802 A | 4/2015 |
| JP | 2017-51645 A | 3/2017 |
| JP | 2017-113635 A | 6/2017 |
| KR | 20-1998-0005117 U | 3/1998 |
| KR | 10-0200669 B1 | 3/1999 |
| KR | 10-2003-0068633 A | 8/2003 |
| KR | 10-2004-0093706 A | 11/2004 |
| KR | 10-0786539 B1 | 12/2007 |
| KR | 10-0790758 B1 | 12/2007 |
| KR | 10-2008-0045022 A | 5/2008 |
| KR | 10-0851274 B1 | 8/2008 |
| KR | 10-2010-0041207 A | 4/2010 |
| KR | 10-2010-0060222 A | 6/2010 |
| KR | 10-2010-0135863 A | 12/2010 |
| KR | 10-1053835 B1 | 8/2011 |
| KR | 10-2011-0119640 A | 11/2011 |
| KR | 10-2012-0115703 A | 10/2012 |
| KR | 10-2013-0087770 A | 8/2013 |
| KR | 10-1366126 B1 | 2/2014 |
| KR | 10-1386137 B1 | 4/2014 |
| KR | 10-2014-0052667 A | 5/2014 |
| KR | 10-2014-0069431 A | 6/2014 |
| KR | 10-2015-0030264 A | 3/2015 |
| KR | 10-2015-0062305 A | 6/2015 |
| KR | 10-2015-0062492 A | 6/2015 |
| KR | 10-2016-0048425 A | 5/2016 |
| KR | 10-2016-0121019 A | 10/2016 |
| KR | 10-2016-0146337 A | 12/2016 |
| KR | 10-1707659 B1 | 2/2017 |
| KR | 10-1719459 B1 | 3/2017 |
| KR | 10-2017-0041776 A | 4/2017 |
| KR | 10-2017-0083399 A | 7/2017 |
| KR | 10-2017-0089842 A | 8/2017 |
| KR | 10-1813652 B1 | 8/2017 |
| KR | 10-2017-0130470 A | 11/2017 |
| KR | 10-1819204 B1 | 1/2018 |
| KR | 10-2018-0054247 A | 5/2018 |
| KR | 10-1840346 B1 | 5/2018 |
| KR | 10-1862127 B1 | 5/2018 |
| KR | 10-1300120 B1 | 8/2018 |
| KR | 10-2018-0109828 A | 10/2018 |
| KR | 10-1905830 B1 | 10/2018 |
| KR | 10-1936890 B1 | 1/2019 |
| KR | 10-2019-0074150 A | 6/2019 |
| WO | WO 2016/154399 A1 | 9/2016 |
| WO | WO 2018/093141 A2 | 5/2018 |
| WO | WO 2018/231868 A1 | 12/2018 |

OTHER PUBLICATIONS

International Search Report dated Jun. 4, 2018 for PCT/KR2017/012935.
International Search Report dated Jul. 6, 2018 for PCT/KR2018/003773.
International Search Report dated Aug. 8, 2018 for PCT/KR2017/013901.
International Search Report dated May 30, 2019 for PCT/KR2018/016491.
International Search Report and Written Opinion dated Aug. 14, 2019 for PCT/KR2019/005105.
International Search Report and Written Opinion dated Nov. 15, 2019 for PCT/KR2019/009411.
International Search Report dated Mar. 27, 2020, for PCT/KR2019/017328.
International Search Report dated Mar. 4, 2021, for PCT/KR2020/012886.
International Written Opinion dated Mar. 4, 2021, for PCT/KR2020/012886.
Korean Notice of Allowance dated Jun. 30, 2018 for KR 10-2016-0151947.
Korean Office Action dated Oct. 22, 2018 for KR 10-2017-0162715.
Korean Notice of Allowance dated Aug. 29, 2019 for KR 10-2017-0162715.
Korean Office Action dated Oct. 22, 2018 for KR 10-2017-0162716.
Korean Notice of Allowance dated Jul. 29, 2019 for KR 10-2017-0162716.
Korean Office Action dated Jul. 29, 2019 for KR 10-2017-0162717.
Korean Final Office Action dated Jan. 17, 2020 for KR 10-2017-0162717 with Translation.
Korean Office Action dated Nov. 26, 2019 for KR 10-2018-0049108—w/ Trans.
Korean Final Office Action dated May 10, 2020, for KR 10-2018-0049109 with Translation.
Korean Office Action dated Nov. 27, 2019 for KR 10-2018-0049109—w/ Trans.
Korean Notice of Allowance dated Jun. 24, 2020 for KR 10-2018-0049109—w/ Trans.
Korean Office Action dated Dec. 6, 2019 for KR 10-2018-0049110—w/ Trans.
Korean Final Office Action dated May 10, 2020 for KR 10-2018-0049110—w/ Trans.
Korean Notice of Allowance dated Jun. 22, 2020 for KR 10-2018-0049110—w/ Trans.
Korean Office Action dated Dec. 9, 2019 for KR 10-2018-0049115—w/ Trans.
Korean Office Action dated May 10, 2020 for KR 10-2018-0049115, with Eng. Translation.
Korean Notice of Allowance dated Jul. 21, 2020 for KR 10-2018-0049115—w/ Trans.
Korean Office Action dated Dec. 10, 2019 for KR 10-2018-0049117—w/ Trans.
Korean Notice of Allowance dated May 10, 2020 for KR 10-2018-0049117.
Korean Office Action dated Oct. 8, 2019 for KR 10-2018-0052601.
Korean Second Office Action, with translation, dated Oct. 28, 2019 for KR 10-2018-0052601.
Korean Notice of Allowance dated Apr. 2, 2020 for KR 10-2018-0052601 with Eng. Translation.
Korean Office Action dated Oct. 22, 2018, for KR 10-2018-0117138.
Office Action dated Oct. 2, 2019 for U.S. Appl. No. 15/828,449.
Office Action dated May 15, 2020 for U.S. Appl. No. 15/828,449.
Office Action dated Sep. 13, 2019 for U.S. Appl. No. 16/412,296.
Final Office Action dated Jan. 31, 2020 for U.S. Appl. No. 16/412,296.
Office Action dated Jun. 26, 2020 for U.S. Appl. No. 16/412,296.

(56) References Cited

OTHER PUBLICATIONS

Final Office Action dated Oct. 28, 2020 for U.S. Appl. No. 16/412,296.
Office Action Dated Dec. 24, 2020 for US App. No. 17,036,269.
Office Action dated Dec. 8, 2020 for U.S. Appl. No. 17/036,311.
Notice of Allowance dated Feb. 22, 2021 for U.S. Appl. No. 17/036,311.
Notice of Allowance dated Mar. 26, 2021 for U.S. Appl. No. 17/036,311.
Office Action dated Nov. 5, 2020 for U.S. Appl. No. 29/701,630.
Notice of Allowance dated Feb. 3, 2021 for U.S. Appl. No. 29/701,630.
Office Action dated Nov. 5, 2020 for U.S. Appl. No. 29/701,631.
Notice of Allowance dated Feb. 3, 2021 for U.S. Appl. No. 29/701,631.
Smith et al., "Ice Anesthesia for Injection of Dermal Fillers," The American Society for Dermatologic Surgery Inc., Dermatol. Surg 2010:36:812-814, 2010.
Sarifakioglu, et al., "Evaluating the Effects of Ice Application on the Pain Felt During Botulinum Toxin Type-A Injections," Annals of Plastic Surgery, vol. 53, No. 6, Dec. 2004.
European (EUIPO) Examination Report dated Jan. 11, 2021 for 008309504-003.
European (EUIPO) Examination Report dated Feb. 5, 2021 for 008309504-003.
Final Office Action Dated Apr. 13, 2021 for US Appl. No. 17,036,269.
Notice of Allowance dated Apr. 13, 2021 for U.S. Appl. No. 29/701,630.
Corrected Notice of Allowance dated Apr. 20, 2021 for U.S. Appl. No. 29/701,630.
Notice of Allowance dated Apr. 13, 2021 for U.S. Appl. No. 29/701,631.
International Search Report and Written Opinion dated Mar. 27, 2020, for PCT/KR2019/017328.
Notice of Allowance Dated Jun. 25, 2021 for U.S. Appl. No. 17/036,269.
European Extended Search Report dated Jan. 12, 2022 for EP 19791867.5.
European Extended Search Report dated Sep. 29, 2022 for EP 19891927.6.
European Extended Search Report dated Feb. 3, 2023 for EP 22208099.6.
Korean Office Action dated Oct. 21, 2021 with English Translation, for KR 10-2021-0104443.
Korean Office Action dated May 24, 2023 with English Translation, for KR 10-2021-0104443.
Notice of Allowance for U.S. Appl. No. 17/340,633 issued on Feb. 14, 2024.
Written Decision on Registration for Korean Patent Application No. 10-2023-0119555 issued on Feb. 1, 2024.

10000

10000

FIG. 27
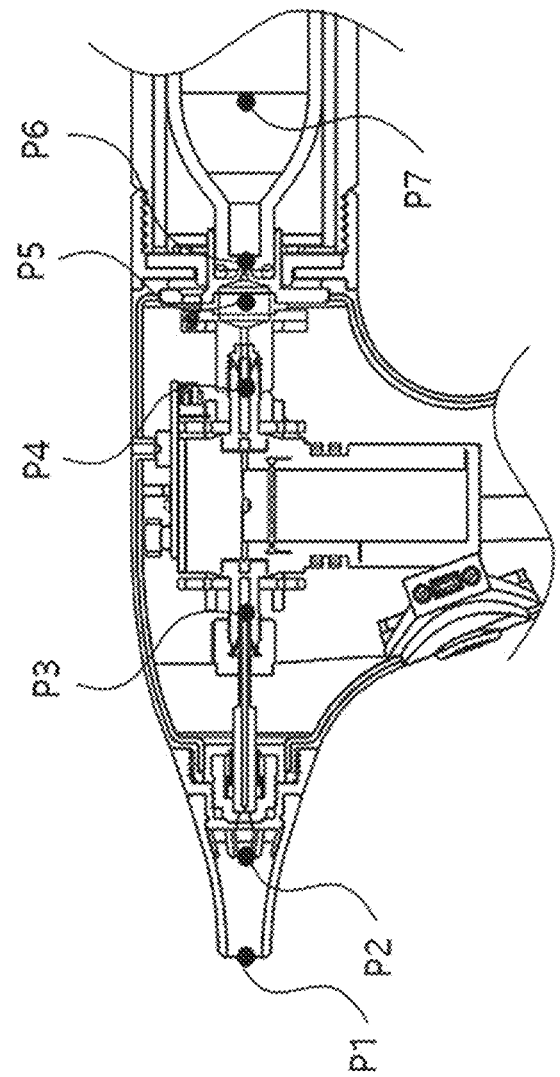
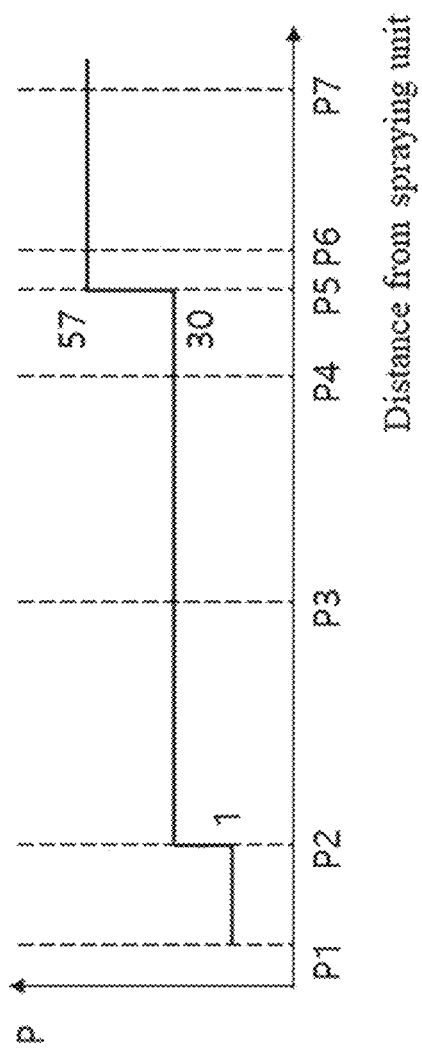

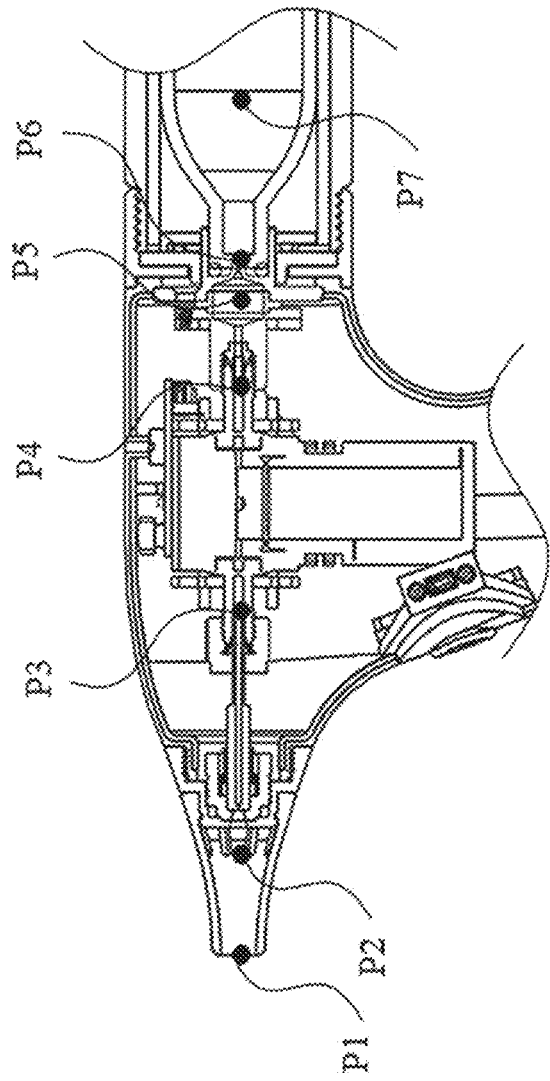
FIG. 28
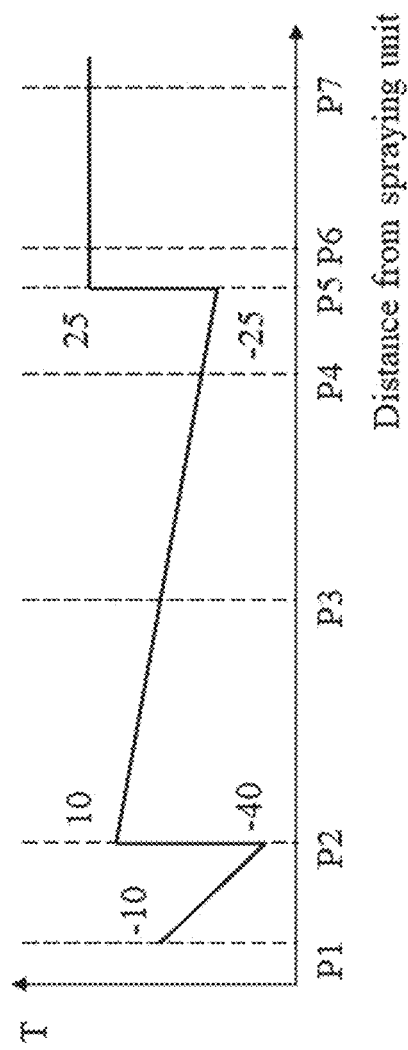

FIG. 30
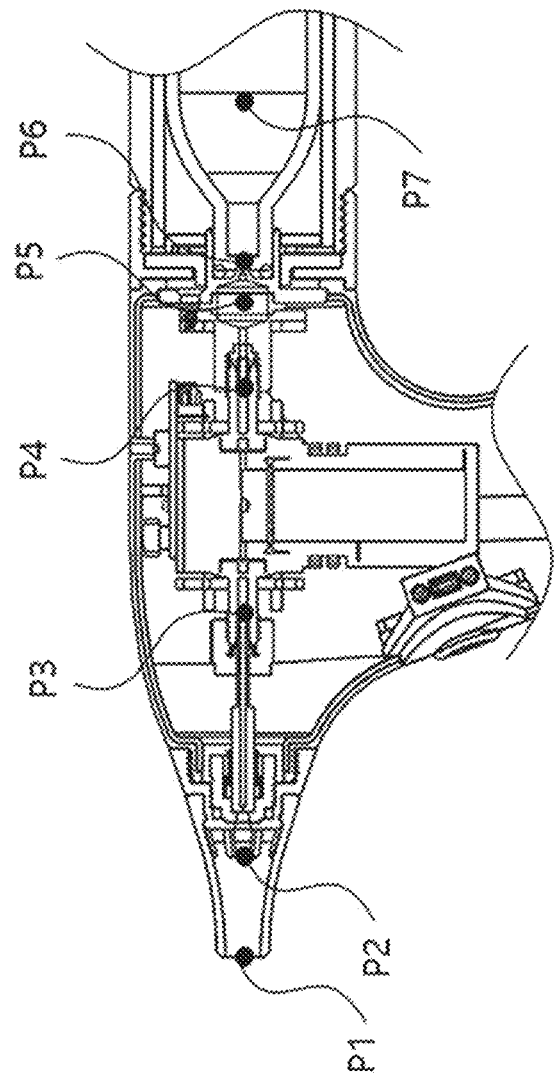
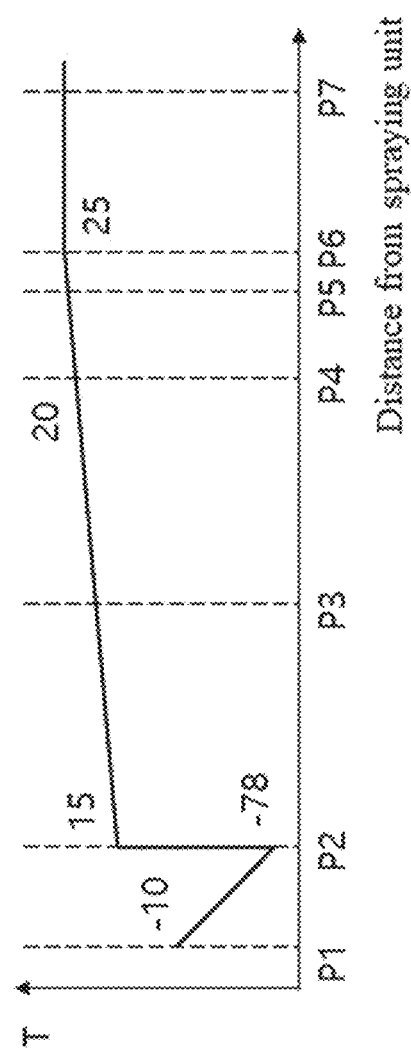

ized about a central axis thereof, and wherein the heater comprises a plurality of heating elements respectively fixed to the plurality of binding fixing surfaces. In the above device, at least a portion of the porous structure is in direct physical contact with an inner wall of the holder tube, and wherein the porous structure extends from the first end of the holder tube to a region in the inner wall of the holder tube adjacent to the second end of the holder tube. In the above device, the first end of the porous structure is substantially radially aligned with the first end of the holder tube, wherein the second end of the porous structure is spaced apart from the second end of the holder tube, wherein the heater is in direct physical contact with the outer circumferential surface of the holder tube, and wherein the heater substantially axially overlaps the porous structure.

In the above device, the holder tube is longer than the porous structure and the heater, and wherein the porous structure is longer than the heater. In the above device, the
HAND-HELD CRYOTHERAPY DEVICE INCLUDING CRYOGEN TEMPERATURE PRESSURE CONTROLLER AND METHOD THEREOF

CROSS-REFERENCE TO RELATED APPLICATION

This is a continuation of U.S. patent application Ser. No. 17/036,311, filed on Sep. 29, 2020, which is a continuation application of International Patent Application No. PCT/KR2019/005105, filed on Apr. 26, 2019, which claims priority to and the benefit of Korean Patent Application No. 10-2018-0049110, filed on Apr. 27, 2018 and Korean Patent Application No. 10-201840157478, filed on Dec. 7, 2018 and Korean Patent Application No. 10-2019-0027184, filed on Mar. 8, 2019, the disclosures of all of which are incorporated herein by reference in their entirety.

BACKGROUND

1. Field

The described technology relates to a cooling method and a cooling device using a cryogen, and more particularly, to a cooling method and a cooling device capable of spraying a cryogen and selectively cooling a target region.

2. Discussion of Related Technology

Cryomedical technology using cooling is used for the purpose of eliminating pain, anesthesia, removing lesions, treating acne, controlling pigmentation, treating hair loss, topical fat reduction, plastic surgery, relieving itching, reducing inflammation, suppressing autoimmune responses, or the like.

Particularly, in the medical field, cryogens, ice, thermoelectric elements, cooled air or water are typical materials used in cryotechnology.

Taking into consideration that heat capacity of body tissues is high, cryomedical technology based on cryogens is the most efficient means for cooling body tissues and is actively discussed in the field of dermatology to remove various types of lesions.

SUMMARY

One aspect is a cooling device and a cooling method that can stably implement cooling conditions, which are required for various clinical effects, such as effective destruction of cells in lesions, minimization of destruction of normal cells surrounding the cells in lesions, cryoanesthesia, and immune activation by cooling.

Another aspect is a cooling device that receives a cryogen from a cryogen reservoir and cools a target region, the cooling device including: a spraying unit from which the cryogen is sprayed; a valve configured to regulate a flow of the cryogen; and a cryogen cooling unit disposed at a rear end of the valve and configured to receive the cryogen from the cryogen reservoir and keep a pressure of the cryogen supplied from the cryogen reservoir at a predetermined pressure.

Another aspect is a cooling device that receives a cryogen from a cryogen reservoir and cools a target region, the cooling device including: a spraying unit from which the cryogen is sprayed; a valve configured to regulate a flow of the cryogen, and a cryogen temperature pressure controller disposed between the spraying unit and the valve and configured to heat the cryogen moving to the spraying unit and control a temperature and a pressure of the cryogen.

Another aspect is a hand-held cooling device for supplying a cryogen to a target region for cryotherapy, the hand-held cooling device comprising: a cryogen container configured to contain a first cryogen having a first temperature; a nozzle configured to spray a first modified cryogen to the target region, the first modified cryogen having a second temperature higher than the first temperature: a valve disposed between the cryogen container and the nozzle and configured to regulate a flow of the first cryogen; a cryogen temperature regulator disposed between the nozzle and the valve and configured to receive the first cryogen from the valve and output the first modified cryogen to the nozzle, the cryogen temperature regulator disposed closer to the nozzle than the valve and the cryogen container: and a main controller configured to control closing and opening operations of the valve and activating and deactivating operations of the cryogen temperature regulator, wherein the cryogen temperature regulator comprises: a holder tube disposed between the valve and the nozzle and configured to receive the first cryogen from the valve via a first end thereof and output the first modified cryogen to the nozzle via a second end thereof; a porous structure disposed inside the holder tube, the porous structure comprising a first end adjacent to the first end of the holder tube, a second end adjacent to the second end of the holder tube, and a body extending from the first end of the porous structure to the second end of the porous structure, the porous structure configured to receive the first cryogen at the first end thereof, pass the received first cryogen through the body and output the first modified cryogen via the second end thereof to the second end of the holder tube; a first insulating member coupled to the first end of the holder tube and configured to thermally insulate the holder tube from the cryogen container and the valve; a second insulating member disposed between the second end of the holder tube and the nozzle and configured to thermally insulate the holder tube from the nozzle; and a heater disposed around an outer circumferential surface of the holder tube and configured to apply heat to the holder tube to increase the first temperature of the first cryogen to the second temperature of the first modified cryogen while the first cryogen passes through the body of the porous structure such that the first modified cryogen having the second temperature is output from the second end of the holder tube to the nozzle.

In the above device, the holder tube comprises a plurality of binding fixing surfaces disposed radially or symmetrically about a central axis thereof, and wherein the heater comprises a plurality of heating elements respectively fixed to the plurality of binding fixing surfaces. In the above device, at least a portion of the porous structure is in direct physical contact with an inner wall of the holder tube, and wherein the porous structure extends from the first end of the holder tube to a region in the inner wall of the holder tube adjacent to the second end of the holder tube. In the above device, the first end of the porous structure is substantially radially aligned with the first end of the holder tube, wherein the second end of the porous structure is spaced apart from the second end of the holder tube, wherein the heater is in direct physical contact with the outer circumferential surface of the holder tube, and wherein the heater substantially axially overlaps the porous structure.

In the above device, the holder tube is longer than the porous structure and the heater, and wherein the porous structure is longer than the heater. In the above device, the nozzle comprises an inlet opening configured to receive the first modified cryogen from the second end of the holder tube and an outlet configured to spray the first modified cryogen to the target region, and wherein the second end of the holder tube has an inner width greater than the inlet opening of the nozzle. In the above device, the first insulation member is disposed around and in direct physical contact with an outer surface of the first end of the holder tube, and wherein the second insulation member is disposed around and in direct physical contact with an outer surface of the second end of the holder tube.

In the above device, the first modified cryogen has a pressure higher than that of the first cryogen. In the above device, the porous structure comprises sintering metal particles having thermal conductivity. In the above device, the main controller is configured to deactivate the cryogen temperature controller before closing the valve so as to cool the cryogen temperature controller. In the above device, the main controller is further configured to transmit a pulse signal for opening or closing the valve, and within a predetermined time from when a transmission of the pulse signal terminates, to transmit a signal for deactivating the cryogen temperature controller.

In the above device, the main controller is further configured to control the valve and the cryogen temperature controller such that the cryogen temperature regulator outputs a second modified cryogen to the nozzle after the cryogen temperature regulator is deactivated, the second modified cryogen having a third temperature not higher than the second temperature. The above device further comprises: a cryogen cooling unit configured to receive the first cryogen from the cryogen container and maintain a pressure of the first cryogen at a predetermined pressure; and a power supply configured to supply power to at least one of the valve and the cryogen temperature controller.

The above device further comprises: an upper body; and a hand body spaced apart from a front end of the upper body by a predetermined distance and integrally formed to have a predetermined angle with the upper body, wherein the cryogen cooling unit is disposed at a rear end of the upper body, wherein the nozzle is disposed at the front end of the upper body, and wherein the power supply is disposed in the hand body. The above device further comprises a heat sink configured to release heat from the cryogen cooling unit, wherein the heat sink is disposed at the rear end of the upper body. In the above device, the valve comprises: an inlet configured to receive the first cryogen from the cryogen container; an outlet configured to output the first cryogen to the cryogen temperature controller; a plunger configured to reciprocate to block a flow of the first cryogen into the cryogen temperature regulator; and an armature configured to generate an induced magnetic force.

In the above device, the valve is disposed at a region where the upper body and the hand body are connected, and the armature is disposed on an upper portion of the hand body. In the above device, the inlet of the valve is formed in a second direction parallel to a first direction in which the outlet of the valve is formed, and the plunger is configured to reciprocate in a third direction substantially perpendicular to the first direction.

Another aspect is a hand-held cooling device for supplying a cryogen to a target region for cryotherapy, the hand-held cooling device comprising: a cryogen container configured to contain a first cryogen having a first temperature; a nozzle configured to spray a first modified cryogen to the target region, the first modified cryogen having a second temperature higher than the first temperature; a valve disposed between the cryogen container and the nozzle and configured to regulate a flow of the first cryogen; and a cryogen temperature regulator disposed between the nozzle and the valve and configured to receive the first cryogen from the valve and output the first modified cryogen to the nozzle, the cryogen temperature regulator disposed closer to the nozzle than the valve and the cryogen container, wherein the cryogen temperature regulator comprises: a holder tube disposed between the valve and the nozzle and configured to receive the first cryogen from the valve via a first end thereof and output the first modified cryogen to the nozzle via a second end thereof; a porous structure disposed inside the holder tube, the porous structure comprising a first end adjacent to the first end of the holder tube, a second end adjacent to the second end of the holder tube, and a body extending from the first end of the porous structure to the second end of the porous structure, the porous structure configured to receive the first cryogen at the first end thereof, pass the received first cryogen through the body and output the first modified cryogen via the second end thereof to the second end of the holder tube; and a heater disposed around an outer circumferential surface of the holder tube and configured to apply heat to the holder tube to increase the first temperature of the first cryogen to the second temperature of the first modified cryogen while the first cryogen passes through the body of the porous structure such that the first modified cryogen having the second temperature is output from the second end of the holder tube to the nozzle.

Another aspect is a method of supplying a cryogen to a target region via a hand-held cooling device for cryotherapy, the method comprising: storing, at a cryogen container of the hand-held cooling device, a first cryogen having a first temperature: regulating, at a valve of the hand-held cooling device, a flow of the first cryogen; controlling, at a cryogen temperature regulator of the hand-held cooling device, the first temperature of the first cryogen to output a first modified cryogen having a second temperature higher than the first temperature to a nozzle of the hand-held cooling device, the cryogen temperature regulator disposed closer to the nozzle than the valve and the cryogen container, the cryogen temperature regulator comprising a holder tube disposed between the valve and the nozzle, a heater disposed around the holder tube, and a porous structure disposed inside the holder tube, the holder tube thermally insulated from the valve, the cryogen container and the nozzle; and spraying the first modified cryogen to the target region via the nozzle, wherein the controlling comprises: receiving the first cryogen at a first end of the porous structure from the valve; passing the received first cryogen through a body of the porous structure: applying heat to the holder tube via the heater while the first cryogen passes through the body of the porous structure to increase the first temperature of the first cryogen to the second temperature of the first modified cryogen; and outputting the first modified cryogen to the nozzle via a second end of the porous structure opposing the first end of the porous structure, the second end of the porous structure being closer to the nozzle than the first end of the porous structure.

Various embodiments can provide the following non-limiting benefits.

By keeping a pressure of a cryogen continuously at a location adjacent to a cryogen spraying unit, the cryogen can reach a predetermined thermodynamic state with a fast dynamic response. Also, by controlling a thermodynamic phase of the cryogen right before the cryogen is sprayed to a treatment site, the cryogen can be sprayed to the treatment site while a temperature of the cryogen is controlled to a desired temperature. In addition, by controlling heat at the treatment site other than a target site to be cooled, it is possible to prevent excessive cooling from occurring outside a target region.

By regulating a cooling site while rapidly controlling the temperature of the cryogen as described above, it is possible to stably implement cooling protocols for various treatment protocols for various clinical effects, such as cryoanesthesia, treatment on cells in lesions using immune activation, and treatment to kill cells in lesions with minimal normal cell destruction, or treatment in which various clinical effects are combined, such as treatment to kill cells in lesions while pain is minimized by first applying cooling conditions corresponding to cryoanesthesia.

BRIEF DESCRIPTION OF THE DRAWINGS

FIGS. 27, 28, 29 and 30 are views for describing an operation of the cooling device according to an embodiment of the present application.

DETAILED DESCRIPTION

Figure 1:
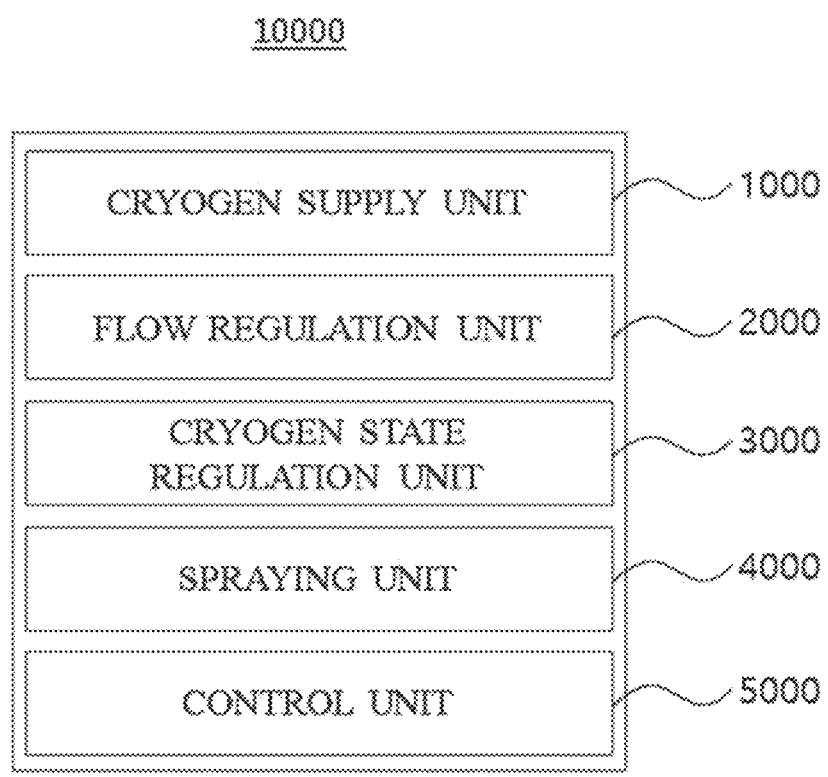
FIG. 1 is a view for describing a configuration of a cooling device according to an embodiment of the present application.

Generally, it is difficult to control temperature of cryogens and cooling means other than the cryogens are unable to efficiently cool the body tissues, despite the clinical expectations that cryomedical technology might be used for many medical symptoms, it has not been used effectively beyond surgical therapies such as tissue resection so far.

In the means of cooling body tissues with cryogens that is most used in cryomedical treatment nowadays, the control of cooling temperature is performed by simply controlling a speed of a cryogen, mixing the cryogen with another fluid, or the like, and thus precise control is difficult over a wide range of temperatures.

For example, even until now, precision in temperature control is insufficient for applying cryomedical technology to medical fields such as anesthesia, pain relief, acne treatment, skin pigmentation control, and hair loss treatment, and thus satisfactory results have not been obtained.

The described technology is directed to providing a more precise and efficient cooling technology, and the means of the described technology are expected to bring further effects in the aforementioned treatment of lesions.

Specifically, the described technology will introduce a cooling device that, in applying a cryogen (referred to as "cryogen") to the body, controls a thermodynamic state of the cryogen and is typically capable of precisely controlling temperature by the Joule-Thomson effect. Particularly, in order to apply cryomedical technology, the described technology may precisely and promptly control a temperature of a target region of the body, a depth of the target region, an area of the target region, and the like.

In the described technology, in presenting cryomedical technology using cryogen, products and technologies for anesthetizing or treating eyes and body tissues other than the eyes will be mainly described.

In order to perform intravitreal injection or vision correction surgery such as LASIK or LASEK, the patient's eye needs to be anesthetized first. In the case of anesthetic agents, the anesthetic effect may be insufficient due to the limitation that the anesthetic agents take time to reach pain-sensing nerves and the possibility that chemicals may not diffuse well. To effectively compensate for this, the described technology proposes a device and method capable of spraying a cryogen to the eye and anesthetizing the eye before performing intravitreal injection, vision correction surgery, and the like.

Particularly, in the case of ocular anesthesia, precision is required to effectively anesthetize only the portion where an injection needle is inserted, and promptness is required to reduce waiting time for the main medical treatment after the patient is anesthetized. For precise control of ocular anesthesia, doctors have a high demand for medical devices that are easy to use and have high portability. Therefore, cryogens for anesthesia need to be mounted in small amounts in medical devices so as not to degrade the usability of the medical devices.

A cooling device proposed by the described technology that applies a container-type or cartridge-type cryogen product which holds a small amount of cryogen has high portability and is designed to facilitate replacement of the cryogen product when the cryogen is used up.

On the other hand, when cryomedical technology is applied to parts of the body other than the eye, such as the skin, the amount of cryogen consumed is very large due to the need to perform multiple treatments per patient. In this case, the cryogen product which is attached to and detached from a medical device and replaced may degrade the usability of the medical device due to rapid consumption of cryogen. Therefore, the described technology also discloses a cooling device which receives a cryogen from a high-capacity cryogen reservoir or the like outside the cooling device so that there is less need for replacement even after multiple treatments.

The two types of cooling devices have the advantage that they can be selectively applied according to the lesion and the preference of the doctor, and are not mutually exclusive.

The above-mentioned objectives, features, and advantages of the present application will become more apparent from the following detailed description related to the accompanying drawings. However, the present application may be modified in various ways and have various embodiments. Hereinafter, specific embodiments which are illustrated in the drawings will be described in detail.

In the drawings, the thicknesses of layers and regions are exaggerated for clarity. Also, when an element or layer is described as being "on" or "above" another element or layer, this includes both a case in which the element or layer is directly on the other element or layer and a case in which still another element or layer is interposed therebetween. In principle, like reference numerals refer to like elements throughout. Also, elements having the same function within the scope of the same idea shown in the drawings of each embodiment will be described using the same reference numerals, and redundant description thereof will be omitted.

When detailed description of known functions or configurations related to the present application is deemed as having the possibility of unnecessarily blurring the gist of the present application, the detailed description thereof will be omitted. Also, ordinals (e.g., first and second) used in the description process of the present specification are merely identification symbols for distinguishing one element from another element.

In addition, the terms "module" and "part" which are used to refer to elements in the following embodiments have been given or used in combination with other terms only in consideration of ease of writing the specification and thus do not have meanings or roles that are distinguished from each other.

In the following embodiments, a singular expression includes a plural expression unless the context clearly indicates otherwise.

In the following embodiments, terms such as "include" or "have" designate that features or elements described herein exist and do not preclude the possibility of adding one or more other features or elements in advance.

In the following embodiments, when a part such as a film, a region, or an element is described as being on or above another part, this not only includes a case in which the part is directly on the other part, but also includes a case in which still another film, region, element, or the like is interposed therebetween.

In the drawings, sizes of elements may have been exaggerated or reduced for convenience of description. For example, the size and thickness of each element shown in the drawings are arbitrarily shown for convenience of description, and the described technology is not necessarily limited thereto.

When a certain embodiment may be implemented differently, a specific process may be performed in an order different from a described order. For example, two processes described in succession may be performed substantially concurrently or performed in the reverse order.

In the following embodiments, when films, regions, or elements are described as being connected, this not only includes a case in which the films, the regions, or the elements are directly connected, but also includes a case in which the films, the regions, or the elements are indirectly connected with other films, regions, or elements interposed therebetween. For example, in the present specification, when films, regions, or elements are described as being electrically connected, this not only includes a case in which the films, the regions, or the elements are directly electrically connected, but also includes a case in which the films, the regions, or the elements are indirectly electrically connected with other films, regions, or elements interposed therebetween.

An embodiment of the present application may provide a cooling device that receives a cryogen from a cryogen reservoir and cools a target region, the cooling device including: a spraying unit from which the cryogen is sprayed; a valve configured to regulate a flow of the cryogen; and a cryogen cooling unit disposed at a rear end of the valve and configured to receive the cryogen from the cryogen reservoir and keep a pressure of the cryogen supplied from the cryogen reservoir at a predetermined pressure.

The cryogen cooling unit may receive the cryogen from the cryogen reservoir through a first flow path and discharge the cryogen to the valve through a second flow path. The cryogen cooling unit may cool the cryogen so as to increase a proportion of liquid phase in the cryogen in the second flow path more than a proportion of liquid phase in the cryogen in the first flow path.

The cryogen cooling unit may further include a thermoelectric element configured to cool the cryogen.

While the cryogen is supplied to the target region, proportions of liquid phase in the second flow path and the cryogen cooling unit may be substantially the same.

While the cryogen is supplied to the target region, a proportion of liquid phase in the cryogen may be high in the order of the cryogen cooling unit, the second flow path, and the first flow path.

The cryogen sprayed from the spraying unit may include gas phase and solid phase.

An embodiment of the present application may provide a cooling device that receives a cryogen from a cryogen reservoir and cools a target region, the cooling device including: a spraying unit from which the cryogen is sprayed; a valve configured to regulate a flow of the cryogen, and a cryogen temperature pressure controller disposed between the spraying unit and the valve and configured to heat the cryogen moving to the spraying unit and control a temperature and a pressure of the cryogen.

The cryogen temperature pressure controller may include a thermoelectric element thermally connected to the cryogen and having a first side configured to heat the cryogen and a second side configured to perform an endothermic reaction according to an exothermic reaction of the first side, wherein the first side is disposed closer to a moving path of the cryogen than the second side.

The cryogen temperature pressure controller may include a heating element configured to heat the cryogen and a heat transfer medium thermally connected to the heating element and coming in contact with the cryogen.

The heat transfer medium may be a porous structure formed by sintering metal particles having thermal conductivity.

The cooling device may further include a control unit configured to control the cryogen temperature pressure controller. To cool the cryogen temperature pressure controller, the control unit may stop driving of the cryogen temperature pressure controller before the valve is closed.

The cooling device may further include a control unit configured to control the valve and the cryogen temperature pressure controller. The control unit may transmit a pulse signal which opens or closes the valve and, within a predetermined time from when the transmission of the pulse signal ends, transmit a signal which stops driving of the cryogen temperature pressure controller.

The cooling device may further include a control unit configured to control the valve and the cryogen temperature pressure controller. The control unit may control the valve and the cryogen temperature pressure controller so that a cryogen whose temperature is in a first temperature range is sprayed through the spraying unit and then a cryogen whose temperature is in a second temperature range is sprayed. The first temperature range may include a temperature of a cryogen heated by the cryogen temperature pressure controller, and the second temperature range may include a temperature of a cryogen sprayed after termination of driving of the cryogen temperature pressure controller ends.

The cooling device may further include a cryogen cooling unit configured to receive a cryogen from the cryogen reservoir and keep a pressure of the cryogen supplied from the cryogen reservoir at a predetermined pressure and a power supply unit configured to supply power to at least one of the valve and the cryogen temperature pressure controller.

The cooling device may further include a body unit including a horizontal body and a hand body spaced a predetermined distance apart from a front end of the horizontal body and integrally formed to have a predetermined angle with the horizontal body. The cryogen cooling unit may be disposed at a rear end of the horizontal body, the spraying unit may be disposed at the front end of the horizontal body, and the power supply unit may be disposed at the hand body.

The cooling device may further include a heat sink configured to release heat from the cryogen cooling unit. The heat sink may be disposed at the rear end of the horizontal body.

The valve may include an inlet into which the cryogen flows, an outlet from which the cryogen is discharged, a plunger configured to reciprocate to block a flow of the cryogen, and an armature configured to generate an induced magnetic force.

The valve may be disposed in a region where the horizontal body and the hand body are connected, and the armature may be disposed at an upper end of the hand body.

The inlet may be formed in a second direction parallel to a first direction in which the outlet is formed, and the plunger may reciprocate in a third direction which is substantially perpendicular to the first direction.

An embodiment of the present application may provide a cooling device that sprays a cryogen and cools a target region, the cooling device including: a cryogen supply unit configured to supply the cryogen; a valve configured to receive the cryogen from the cryogen supply unit and regulate a flow of the cryogen; a spraying unit from which the cryogen is sprayed; a control unit configured to control the valve and control an amount of the cryogen being sprayed; and a limited-capacity cryogen reservoir disposed between the cryogen supply unit and the valve and configured to accommodate the cryogen of a predetermined amount.

The spraying unit may further include a nozzle unit connected to the valve and configured to discharge the cryogen to the outside.

The cooling device may further include a first flow path disposed between the limited-capacity cryogen reservoir and the cryogen supply unit and a second flow path disposed between the limited-capacity cryogen reservoir and the valve. A cross-sectional area of the first flow path may be less than a cross-sectional area of the second flow path.

In a state in which the valve is open, the cryogen may be in a state of being movable from the limited-capacity cryogen reservoir to the spraying unit. In a state in which the valve is closed, the cryogen may be in a state in which movement thereof from the limited-capacity cryogen reservoir to the spraying unit is blocked.

In the open or closed state of the valve, the cryogen may be movable from the cryogen supply unit to the limited-capacity cryogen reservoir.

The cooling device may further include a filter disposed inside the limited-capacity cryogen reservoir and having a cross-sectional area less than or equal to a cross-sectional area of the limited-capacity cryogen reservoir.

The cross-sectional area of the filter may be greater than at least one of the cross-sectional area of the first flow path and the cross-sectional area of the second flow path.

The control unit may control the valve so that the cryogen is continuously sprayed to a target region for a predetermined time and cool the target region. While the cryogen is sprayed through the spraying unit, the cryogen supplied from the cryogen supply unit may pass through the limited-capacity cryogen reservoir, and a pressure of the cryogen may decrease.

While the cryogen is sprayed through the spraying unit, the cryogen supplied from the cryogen supply unit may pass through the limited-capacity cryogen reservoir, and a temperature of the cryogen may decrease.

While the cryogen is sprayed through the spraying unit, a temperature of the spraying unit may gradually increase as the cryogen reaches the spraying unit from the limited-capacity cryogen reservoir.

The control unit may control an operation of opening the valve and an operation of closing the valve to be performed multiple times for a predetermined time and cool the target region. While the cryogen is sprayed through the spraying unit, a pressure of a cryogen from the limited-capacity cryogen reservoir to the inlet of the valve may be lower than a pressure of a cryogen from the outlet of the valve to an outer side of the spraying unit.

While the cryogen is sprayed through the spraying unit, a temperature of the cryogen from the limited-capacity cryogen reservoir to the inlet of the valve may be lower than a temperature of the cryogen from the outlet of the valve to the outer side of the spraying unit.

The temperature and pressure of the cryogen when the cryogen is discharged to the outside of the nozzle unit may rapidly decrease compared to the temperature and pressure of the cryogen before the cryogen is discharged.

After being discharged from the nozzle unit, the cryogen may be mixed with a fluid inside the spraying unit until the cryogen reaches the target region, and the temperature of the cryogen may increase.

The valve may include an inlet into which the cryogen flows, an outlet from which the cryogen is discharged, a plunger configured to reciprocate to block a flow of the cryogen, and an armature configured to generate an induced magnetic force.

The cooling device may further include a body unit including a horizontal body and a hand body spaced a predetermined distance apart from a front end of the horizontal body and integrally formed to have a predetermined angle with the horizontal body. The cryogen supply unit may be disposed at a rear end of the horizontal body, the spraying unit may be disposed at the front end of the horizontal body, and the power supply unit may be disposed at the hand body.

The valve may be disposed in a region where the horizontal body and the hand body are connected, and the armature may be disposed at an upper end of the hand body.

The inlet may be formed in a second direction parallel to a first direction in which the outlet is formed, and the plunger may reciprocate in a third direction which is substantially perpendicular to the first direction.

An embodiment of the present application may provide a cooling device that sprays a cryogen and cools a target region, the cooling device including: a valve configured to regulate a flow of the cryogen: a spraying unit from which the cryogen is sprayed; a control unit configured to control the valve and control an amount of the cryogen being sprayed; and an input unit configured to detect a user input and transmit an input signal to the control unit, wherein, when an input time during which an input is made to the input unit is a predetermined time or more, the control unit controls the valve to operate so that the cryogen is sprayed, and the input time and an operation time of the valve are not proportional to each other.

An embodiment of the present application may provide a cooling device including: a cryogen supply unit from which a cryogen is supplied; a spraying unit configured to spray the cryogen to a target region; a valve disposed between the cryogen supply unit and the spraying unit; and a control unit configured to control the valve and control an amount of the cryogen being sprayed, wherein, while the cryogen is sprayed to the target region, the control unit controls a sprayed amount of the cryogen being sprayed to the target region, and a minimum temperature time point, which is a time point at which a temperature of the target region is the lowest, is delayed by a predetermined time as compared with a maximum pressure time point, which is a time point at which a pressure applied to the target region is the highest.

A time required to reach the maximum pressure time point from a time point at which the cryogen reaches the target region may be shorter than a time required to reach the minimum temperature time point from the time point at which the cryogen reaches the target region.

The control unit may control the cryogen to be continuously sprayed to a target region for a predetermined time and cool the target region.

The control unit may control an operation of opening the valve and an operation of closing the valve to be performed multiple times for a predetermined time and cool the target region. During one opening of the valve, the minimum temperature time point, which is the time point at which the temperature of the target region is the lowest, may be delayed by a predetermined time as compared with the maximum pressure time point, which is the time point at which the pressure applied to the target region is the highest.

The control unit may control the operation of opening the valve and the operation of closing the valve to be performed multiple times for a predetermined time. When the valve sequentially performs first opening, first closing, second opening, and second closing in that order, a time during which the first opening is performed and a time during which the second opening is performed may be the same, and a time during which the first closing is performed and a time during which the second closing is performed may be the same.

The time during which the first opening is performed may be shorter than the time during which the first closing is performed, and the time during which the second opening is performed may be shorter than the time during which the second closing is performed.

The control unit may control the operation of opening the valve and the operation of closing the valve to be performed multiple times for a predetermined time. When the valve sequentially performs first opening, first closing, second opening, and second closing in that order, a time during which the first opening is performed may be different from a time during which the second opening is performed.

The control unit may control the operation of opening the valve and the operation of closing the valve to be performed multiple times for a predetermined time. When the valve sequentially performs first opening, first closing, second opening, and second closing in that order, a time during which the first closing is performed may be different from a time during which the second closing is performed.

An embodiment of the present application may provide a cooling device including: a cryogen supply unit from which a cryogen is supplied: a spraying unit configured to spray the cryogen to a target region; a valve disposed between the cryogen supply unit and the spraying unit; and a control unit configured to control the valve and control an amount of the cryogen being sprayed, wherein the control unit controls the valve to perform an opening operation and a closing operation multiple times for a predetermined time, and the valve receives a pulse signal from the control unit periodically or non-periodically, controls a supply amount of the cryogen, and periodically or non-periodically provides a first pressure and a second pressure lower than the first pressure to the target region for the predetermined time.

The valve may include an inlet into which the cryogen flows, an outlet from which the cryogen is discharged, a plunger configured to reciprocate to block a flow of the cryogen, and an armature configured to generate an induced magnetic force. The valve may receive the pulse signal from the control unit, generate an electromagnetic force at the armature, change the plunger to an open state, and transfer the cryogen supplied to the first flow path to the second flow path. The cryogen transferred to the second flow path while having a first temperature may be sprayed from the spraying unit, be mixed with a flow of an external fluid present at the guide unit or freely expand before coming into contact with the target region, have the first temperature changed to a second temperature, and be sprayed to the target region.

A flow-rate of the cryogen when the first pressure is provided may be higher than a flow-rate of the cryogen when the second pressure is provided.

The first pressure and the second pressure provided to the target region may generate vibration in the target region.

The reciprocation of the plunger may generate vibration in the target region.

The first pressure and the second pressure provided to the target region may generate first vibration in the target region, and the reciprocation of the plunger may generate second vibration in a direction substantially perpendicular to the first vibration in the target region.

<Cooling Device 10000>

A cooling device 10000 according to an embodiment of the present application may be a device used in lowering a temperature of a target region TR in an environment in which at least one phenomenon of radiation, conduction, and/or convection occurs.

The cooling device 10000 according to an embodiment of the present application may be a device that sprays a gas-, liquid-, and/or solid-phase material (e.g., cryogen) to the target region TR and lowers a temperature of the target region TR.

For example, the cooling device 10000 may spray a cryogen, and the cryogen may come into contact with the target region TR. A heat transfer due to conduction may occur through the contact between the target region TR and the cryogen. The cooling device 10000 may cool at least a portion of the target region TR through the above-described process.

As another example, the cooling device 10000 may spray a cryogen, and the cryogen may flow in one region of the target region TR. In the target region TR, a heat transfer due to convection may occur through the flow of the cryogen. The cooling device 10000 may cool at least a portion of the target region TR through the above-described process.

As still another example, the cooling device 10000 may spray a cryogen, and the cryogen may remain in the target region TR. In the target region TR, a heat transfer may occur due to a phase change of a portion of the cryogen remaining in the target region TR. As a more specific example, when a cryogen in a liquid phase remains in the target region TR and then the phase of the cryogen changes to a gas phase, the cryogen may receive heat corresponding to heat of evaporation or heat of sublimation from the target region TR and cool the target region TR.

The above-described processes may simultaneously occur or sequentially occur, or only at least one of the above-described phenomena may occur. Also, the present application is not limited thereto, and the cooling device 10000 may cool the target region TR using various other methods that may be easily practiced by those of ordinary skill in the art.

The cooling device 10000 according to an embodiment of the present application may perform cooling of the target region TR. For example, the target region TR may be one region related to the human body. As a specific example, the target region TR may be the stratum corneum, the stratum *granulosum*, the stratum *spinosum*, and/or the stratum basale which are located in the epidermis. As another specific example, the target region TR may be sweat glands, hair follicles, sebaceous glands, and/or the layer of fat which are located in the dermis. As another specific example, the target region TR may be oral mucosa, conjunctiva, or the like. As still another specific example, the target region TR may be a tissue including an epidermal tissue, an epithelial tissue, a connective tissue, a cartilage tissue, an osseous tissue, blood, lymph, a muscle tissue, and/or a nerve tissue.

The cooling device 10000 according to an embodiment of the present application may be utilized in various fields. For example, the cooling device 10000 may be used to perform cooling of the target region TR and induce an anesthetic effect in the target region TR or used for effective destruction of cells in lesions. Alternatively, the cooling device 10000 according to an embodiment of the present application may perform cooling of the target region TR and induce effects such as fat reduction in a local site, reduction of skin aging, relief of itching, reduction of inflammation, and suppression of autoimmune responses.

Alternatively, the cooling device 10000 according to an embodiment of the present application may perform cooling of the target region TR and cause a hypopigmentation effect, thereby eliminating or reducing hyperpigmentation such as freckles.

The present application is not limited thereto, and the cooling device 10000 may be used to stably implement cooling conditions and cause various clinical effects.

One objective of the present application is to provide the cooling device 10000 capable of performing precise cooling control.

Hereinafter, the cooling device 10000 according to an embodiment of the present application will be described.

1. Elements of Cooling Device 10000

FIG. 1 is a view for describing a configuration of the cooling device 10000 according to an embodiment of the present application.

The cooling device 10000 according to an embodiment of the present application may include a cryogen supply unit 1000, a flow regulation unit 2000, a cryogen state regulation unit 3000, a spraying unit 4000, and a control unit 5000.

However, the above description only clearly discloses that the cooling device 100(*x*) according to an embodiment of the present application may include the above elements, and the cooling device 10000 according to an embodiment of the present application may also be a device from which at least one of the above elements of the cooling device 10000 is removed, a device that further includes an element other than the above elements of the cooling device 10000, or a device in which some of the above elements of the cooling device 10000 are provided in a plurality.

Hereinafter, for better understanding, functions, structures, and specific embodiments of the cryogen supply unit 1000, the flow regulation unit 2000, the cryogen state regulation unit 3000, the spraying unit 4000, and the control unit 5000.

1.1 Cryogen supply unit 1000

1.1.1 Cryogen supply unit 1000

The cryogen supply unit 1000 according to an embodiment of the present application may perform a cryogen providing function. The cryogen supply unit 1000 may perform a function of providing a cryogen flowing in the cooling device 10000. The cryogen supply unit 1000 may perform a function of providing a cryogen flowing in the flow regulation unit 2000, the cryogen state regulation unit 3000, and/or the spraying unit 4000.

The cryogen may be in a gas-, liquid-, and/or solid-phase. In other words, the cryogen may be in a gas phase, a liquid phase, or a solid phase, or may be a mixture in which cryogens in at least two or more phases are distributed together.

The cryogen may be a material capable of performing cooling by the Joule-Thomson effect when the cryogen is sprayed at normal pressure. For example, the cryogen may be nitrogen ($N_2$), nitrous oxide ($N_2O$), carbon dioxide ($CO_2$), or the like. However, the cryogen is not limited to materials disclosed in the present application and may also correspond to general materials used as cryogens by those of ordinary skill in the art.

The cryogen supply unit 1000 according to an embodiment of the present application may perform a cryogen supplying function. The cryogen supply unit 1000 may perform a function of supplying a cryogen flowing to the cooling device 10000. The cryogen supply unit 1000 may perform a function of supplying a cryogen to the flow regulation unit 20(x), the cryogen state regulation unit 3000, and/or the spraying unit 4000.

The cryogen supply unit 1000 according to an embodiment of the present application may perform a function of supplying a cryogen so that the cryogen moves to at least a partial region of the elements of the cooling device 10000. For example, the cryogen may be influenced by gravity and move from the cryogen supply unit 1000 to at least a partial region of the elements of the cooling device 10000. As another example, the cryogen may be influenced by a pressure difference and move from the cryogen supply unit 1000 to at least a partial region of the elements of the cooling device 10000.

The cryogen supply unit 1000 according to an embodiment of the present application may be disposed at one end of a flow path formed in the cooling device 10000.

The cryogen supply unit 1000 according to an embodiment of the present application may be disposed at a position spaced apart from the spraying unit 4000 relative to the flow path formed in the cooling device 10000. The cryogen supply unit 1000 may be disposed at a position most spaced apart from the spraying unit 4000 relative to the flow path formed in the cooling device 10000.

1.1.2 Examples of Cryogen Supply Unit 1000

1.1.2.1 Reservoir 1100

According to an embodiment of the present application, the cryogen supply unit 1000 may include a reservoir 1100.

The reservoir 1100 according to an embodiment of the present application may perform a function of keeping a cryogen for an arbitrary time. The reservoir 1100 may perform a function of holding a cryogen for an arbitrary time. The reservoir 1100 may perform a function of accommodating a cryogen for an arbitrary time. The reservoir 1100 may perform a function of storing a cryogen for an arbitrary time.

A relatively high-pressure environment may be formed in the reservoir 1100. A high-pressure environment whose pressure is higher than atmospheric pressure may be formed in the reservoir 1100. A high-pressure environment whose pressure is higher than the those in the flow regulation unit 2000, the cryogen state regulation unit 3000, and/or the spraying unit 4000 may be formed in the reservoir 1100.

According to an embodiment of the described technology, the reservoir 1100 may keep $CO_2$ therein. Here, an environment having a pressure in a range of 1 to 150 bar may be formed in the reservoir 1100. More preferably, an environment having a pressure in a range of 3 to 100 bar may be formed in the reservoir 1100. More preferably, an environment having a pressure in a range of 5 to 80 bar may be formed in the reservoir 1100. More preferably, an environment having a pressure in a range of 20 to 70 bar may be formed in the reservoir 1100.

The reservoir 1100 may have a pressure-resistant characteristic. The reservoir 1100 may be implemented to withstand a pressure of a cryogen stored therein. The reservoir 1100 may be formed to have a pressure-resistant characteristic by properly selecting a material, a thickness, and/or a welding method of the reservoir 1100. For example, the reservoir 1100 may be formed of metal. As a specific example, the reservoir 1100 may be formed of steel or stainless steel. As another example, the reservoir 1100 may be formed of a composite material. As a specific example, the reservoir 1100 may be formed of a composite material including carbon fiber.

The reservoir 1100 may be a tank accommodating a cryogen. The reservoir 1100 may be a cartridge accommodating a cryogen. The reservoir 1100 may be an ordinary bombe accommodating a cryogen. As an example, the reservoir 1100 may be a tank accommodating low-temperature, high-pressure liquefied nitrogen ($N_2$) or carbon dioxide ($CO_2$) therein.

The cooling device 10000 according to an embodiment of the present application may be provided in a structure in which leakage of a cryogen from the reservoir 1100 is prevented.

For example, a structure which prevents leakage of the cryogen may be formed in the reservoir 1100. A structure that closes to prevent leakage of the cryogen stored in the reservoir 1100 may be formed in the reservoir 1100. A structure that performs opening and closing operations so that the cryogen stored in the reservoir 1100 leaks at a time point at which the cryogen should leak may be formed, in the reservoir 1100.

As a specific example, a valve 2100 that allows the cryogen stored in the reservoir 1100 to selectively leak may be provided in the reservoir 1100. The valve 2100 may be opened or closed by a manual operation of a user. Alternatively, the valve 2100 may be opened or closed in response to a specific signal. In this case, the valve 2100 may be opened or closed in response to an electrical signal. Alternatively, the valve 2100 may be opened or closed in response to a pressure change due to a fluid.

As another example, the cooling device 10000 may be provided in the form in which the cryogen continuously leaks from the reservoir 1100. A structure that blocks leakage of the cryogen may be formed in an element of the cryogen that is connected to the reservoir 1100 so that a fluid is movable.

As a specific example, the reservoir 1100 and the flow regulation unit 2000 of the cooling device 10000 may be connected so that a fluid is movable, and continuous leakage of the cryogen stored in the reservoir 1100 may be prevented by a cryogen leakage blocking structure of the flow regulation unit 2000. Alternatively, the cooling device 10000 may have a pipe formed between the reservoir 1100 and the flow regulation unit 2000, and the pipe and the reservoir 1100 may be connected through an O-ring that prevents cryogen loss, thereby preventing cryogen leakage.

1.1.2.2 Transfer Unit 1200

According to an embodiment of the present application, the cryogen supply unit 1000 may include a transfer unit 1200.

The transfer unit 1200 according to an embodiment of the present application may perform a function of receiving a cryogen from the outside and supplying the cryogen to the cooling device 10000. For example, the transfer unit 1200 may perform a function of receiving a cryogen from a tank disposed outside the cooling device 1000 and supplying the cryogen to the cooling device 10000.

The transfer unit 1200 according to an embodiment of the present application may perform a function of providing a passage through which the cooling device 10000 may receive a fluid from the outside. The transfer unit 1200 may perform a function of receiving a cryogen from outside the cooling device 10000 and transferring the cryogen to at least one element of the cooling device 10000.

As a specific example, the transfer unit 1200 may provide a passage that allows a cryogen discharged from a tank physically spaced apart from the cooling device 10000 to flow into the cooling device 10000. The cryogen discharged from the tank may pass through the transfer unit 1200 and move to at least one space of the flow regulation unit 2000, the cryogen state regulation unit 3000, and/or the spraying unit 4000.

The transfer unit 1200 may have a pressure-resistant characteristic. The transfer unit 1200 may be implemented to withstand a pressure of a cryogen so that the cryogen passing through the transfer unit 1200 does not leak. The transfer unit 1200 may be formed to have a pressure-resistant characteristic by properly selecting a material, a thickness, and/or a welding method of the transfer unit 1200.

According to an embodiment of the present application, the transfer unit 1200 may have weather resistance and/or heat resistance. The transfer unit 1200 may be implemented using a heat-resistant material in order to prevent a rapid change in a temperature of the cryogen passing through the transfer unit 1200. The transfer unit 1200 may be implemented using a weather-resistant material in order to prevent corrosion of the transfer unit 1200 due to contact with external moisture or the like.

As a specific example, the transfer unit 1200 may be formed of an aluminum alloy, stainless steel, steel, and/or a copper alloy.

According to an embodiment of the present application, the transfer unit 1200 may be implemented so that a tube in which a cryogen may move is connected to the transfer unit 1200. For example, the transfer unit 1200 may be connected through a tube to a tank in which a cryogen is kept, and the cryogen discharged from the tank may flow into the transfer unit 1200. The tube connecting the tank and the transfer unit 1200 may have flexibility. As a specific example, the tube may be a hose.

The tube connecting the tank and the transfer unit 1200 may have weather resistance and/or heat resistance. For example, the tube connecting the tank and the transfer unit 1200 may be formed of rubber.

1.2 Flow Regulation Unit 2000
1.2.1 Flow Regulation Unit 2000

The flow regulation unit 2000 according to an embodiment of the present application may perform a function of regulating a flow-rate of the cryogen moving along a flow path in the cooling device 10000. The flow regulation unit 2000 may perform a function of regulating a flow-rate of the cryogen moving to the flow regulation unit 2000, the cryogen state regulation unit 3000, and/or the spraying unit 4000.

The flow regulation unit 2000 according to an embodiment of the present application may perform a function of forming a difference between a pressure of a moving flow in a flow path disposed at a first side of the flow regulation unit 2000 and a pressure of a moving flow in a flow path disposed at a second side of the flow regulation unit 2000.

For example, the flow regulation unit 2000 may perform a function of forming a turbulent flow or a chocked flow in the cryogen passing through the flow regulation unit 2000 so that the flow-rate of the cryogen is decreased. Here, due to adiabatic expansion, the temperature of the cryogen may be decreased in advance before the cryogen is supplied to the spraying unit. In other words, the flow regulation unit 2000 may perform a function of causing a temperature of a fluid at an upstream side of the flow regulation unit 2000 to be higher than a temperature of a fluid at a downstream side of the flow regulation unit 2000.

As another example, the flow regulation unit 2000 may regulate discharge of the cryogen passing through the flow regulation unit 2000 and blocking of the discharge of the cryogen. When the flow regulation unit 2000 is in a closed state, the flow regulation unit 2000 may perform a function of causing a plurality of cryogens to be distributed at the upstream side of the flow regulation unit 2000 while a relatively smaller amount of cryogen is distributed at the downstream side of the flow regulation unit 2000. When the flow regulation unit 2000 is in an open state, the flow regulation unit 2000 may perform a function of causing a flow per unit area of the upstream side of the flow regulation unit 2000 to be similar to a flow per unit area of the downstream side of the flow regulation unit 2000.

1.2.2 Examples of Flow Regulation Unit 2000

1.2.2.1 Valve 2100

According to an embodiment of the present application, the flow regulation unit 2000 may include the valve 2100.

The valve 2100 may perform a function of regulating the flow of a cryogen. The valve 2100 may perform a function of causing discharge of a cryogen passing through the valve 2100 or blocking the discharge of the cryogen. Alternatively, the valve 2100 may perform a function of controlling the degree of discharge of the cryogen passing through the valve 2100. The valve 2100 may perform a function of controlling an amount of the cryogen passing through the valve 2100.

According to an embodiment of the present application, the valve 2100 may regulate a flow-rate of the cryogen discharging to the spraying unit 4000 and affect a temperature change of a target region TR where the cryogen discharged from the spraying unit 4000 reaches. Specific embodiments related thereto will be described in detail below.

The valve 2100 according to an embodiment of the present application may be controlled according to a specific signal. The valve 2100 may perform opening and closing operations in response to an electronic signal generated by the control unit 5000. As a specific example, the valve 2100 may be an electronic valve 2100 (e.g., a solenoid valve 2100), but is not limited thereto.

The valve 2100 according to an embodiment of the present application may be controlled according to a mechanical structure and movement of fluid. The valve 2100 may perform the opening and closing operations according to a pressure formed by a fluid moving along the flow path in the cooling device 10000. As a specific example, the valve 2100 may be a hydraulic valve 2100 (e.g., a pressure-control valve 2100), but is not limited thereto.

The valve 2100 according to an embodiment of the present application may be controlled according to a user's input. The valve 2100 may be placed in an open state or a closed state by the user. As a specific example, the valve 2100 may be a manual valve 2100 (e.g., a globe valve 2100), but is not limited thereto.

1.2.2.2 Flow-Rate Restriction Unit 2200

The flow regulation unit 2000 according to an embodiment of the present application may include a flow-rate restriction unit 2200.

The flow-rate restriction unit 2200 may perform a function of reducing an amount of cryogen passing through the flow-rate restriction unit 2200.

Alternatively, the flow-rate restriction unit 2200 may perform a function of keeping the amount of cryogen passing through the flow-rate restriction unit 2200 to a flow-rate less than or equal to a predetermined flow-rate.

According to an embodiment of the present application, the flow-rate restriction unit 2200 may perform a function of setting the maximum amount of a flow-rate of a cryogen discharging to the spraying unit 4000 and preventing the amount of cryogen discharged by passing through the flow-rate restriction unit 2200 from exceeding the limit for safety of the cooling device 10000.

Figure 2:
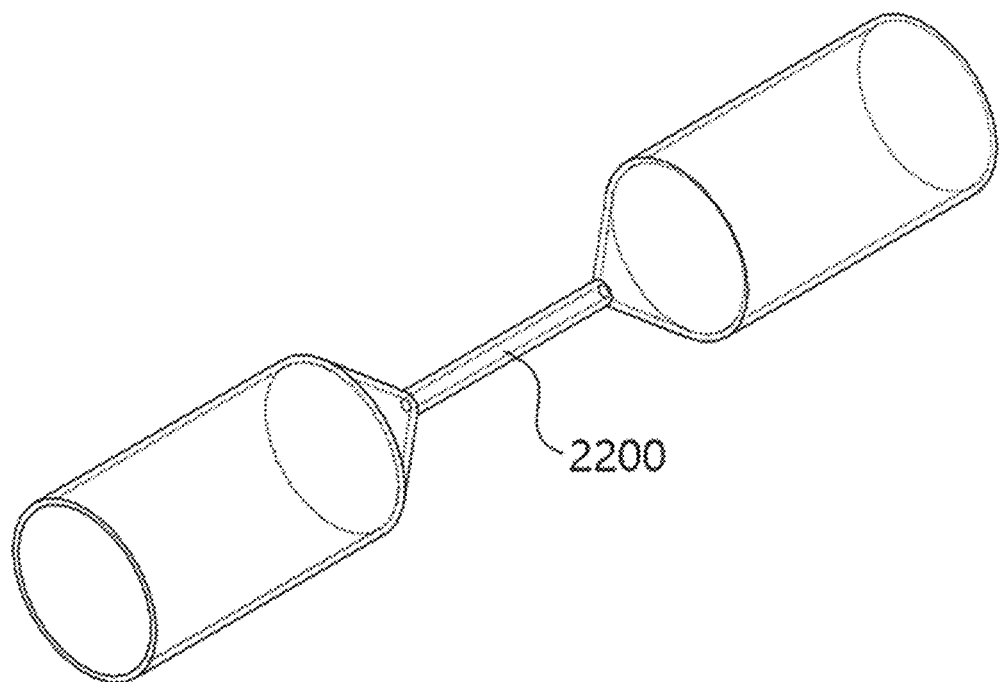
FIGS. 2, 3 and 4 are views for describing a flow-rate restriction unit according to an embodiment of the present application.
Figure 3:
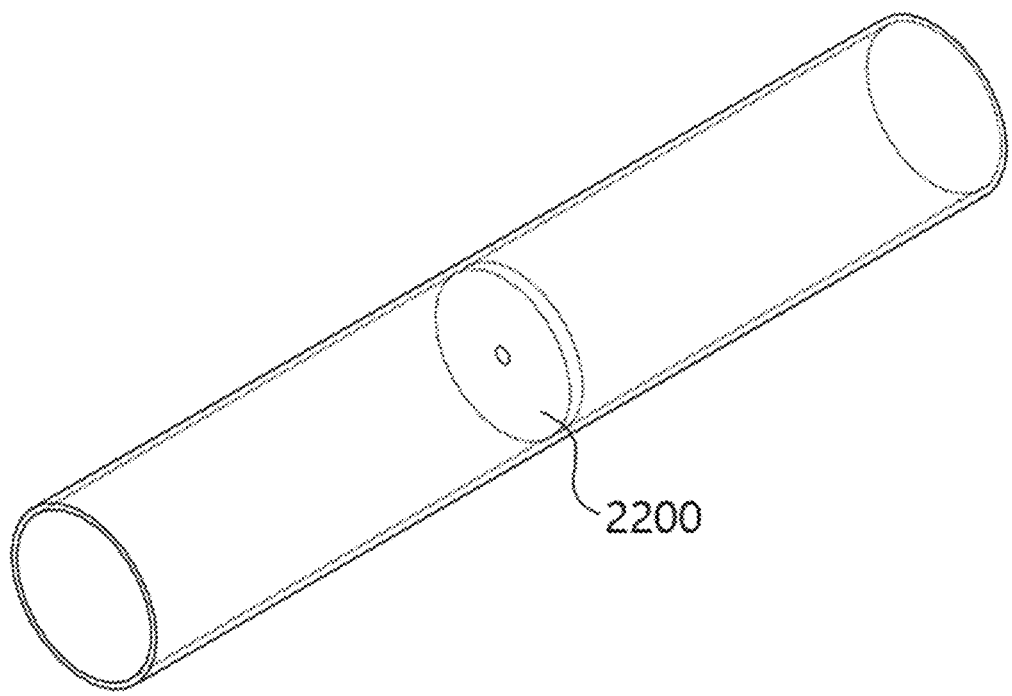
Figure 4:
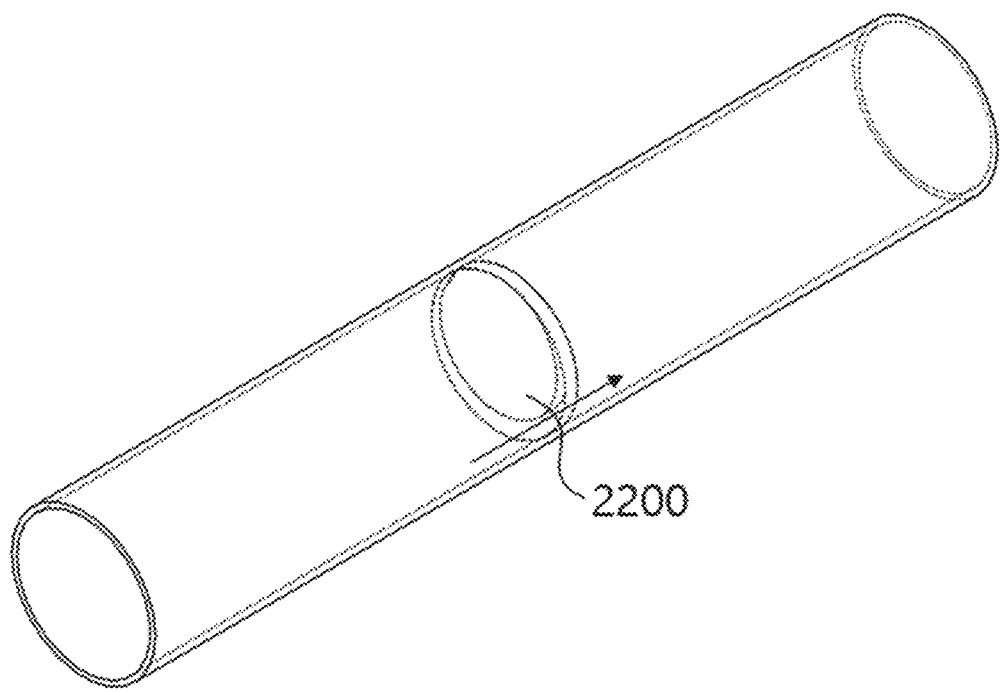

FIGS. 2 to 4 are views for describing the flow-rate restriction unit 2200 according to an embodiment of the present application.

Referring to FIG. 2, the flow-rate restriction unit 2200 according to an embodiment of the present application may refer to a region in which a cross-sectional area is relatively small in the flow path formed in the cooling device 10000. The flow-rate restriction unit 2200 may refer to a region in which a cross-sectional area is the smallest in the flow path formed in the cooling device 10000.

As a specific example, in a case in which a first point, a second point, and a third point are present in the flow path formed in the cooling device 10000 from the upstream side to the downstream side, a section corresponding to the second point may serve as the flow-rate restriction unit 2200 when cross-sectional area of pipes at the first point and the third point are the same and a cross-sectional area of a pipe at the second point is significantly small. The upstream and downstream described herein may refer to positions according to a chronological order while the cryogen flows in the passage through which the cryogen flows, instead of referring to positions according to the direction in which gravity is applied.

Referring to FIGS. 3 and 4, the flow-rate restriction unit 2200 according to an embodiment of the present application may refer to a region in which a barrier for reducing a cross-sectional area through which a fluid is movable is installed in at least a partial region of the flow path formed in the cooling device 10000.

As a specific example, in a case in which a first point, a second point, and a third point are present in the flow path formed in the cooling device 10000 from the upstream side to the downstream side, a section corresponding to the second point may serve as the flow-rate restriction unit 2200 when a cross-sectional area through which a fluid is movable at the second point is significantly small as compared with those at the first point and the third point.

Referring to FIG. 3, the barrier may have a shape corresponding to the shape of the pipe and have a structure in which a hole, through which a fluid may pass, is formed. Referring to FIG. 4, the barrier may have a shape corresponding to the shape of the pipe and have a structure in which a barrier is formed with a cross-sectional area smaller than that of the pipe so that a clearance is present between the barrier and an internal diameter of the pipe.

As illustrated in FIG. 4, the cryogen distributed inside the pipe may move through the clearance between the barrier and the internal diameter of the pipe.

In this way, the flow-rate restriction unit 2200 may be implemented by forming a relatively narrow flow path in a flow path through which the cryogen flows. Here, the cryogen passing through the flow-rate restriction unit 220 may form a turbulent flow or a chocked flow. In this way, the flow-rate restriction unit 2200 may restrict the flow-rate of the cryogen.

Further, the turbulent flow or chocked flow formed by the cryogen may cause irreversible reduction of the pressure of the cryogen. In this way, the temperature of the cryogen may be decreased before the cryogen is transferred to the spraying unit.

For example, the flow-rate restriction unit 2200 according to an embodiment of the present application may also perform a function of limiting the temperature of the cryogen by performing the function of restricting the flow-rate of the cryogen passing through the flow-rate restriction unit 2200, thereby inducing an effect of safely cooling the target region TR.

1.3 Cryogen State Regulation Unit 3000

1.3.1 Cryogen State Regulation Unit 3000

The cryogen state regulation unit 3000 according to an embodiment of the present application may perform a function of regulating a physical state of a cryogen. The cryogen state regulation unit 30000 may perform a function of regulating a physical state of a cryogen passing through the cryogen state regulation unit 3000.

The cryogen state regulation unit 3000 according to an embodiment of the present application may perform a function of regulating a physical state of a cryogen in the cooling device 10000. The cryogen state regulation unit 3000 may perform a function of regulating a physical state of a cryogen moving through the cryogen supply unit 1000, the flow regulation unit 2000 and/or the spraying unit 4000.

For example, the cryogen state regulation unit 3000 may control a temperature of a cryogen. The cryogen state regulation unit 3000 may heat the cryogen. Alternatively, the cryogen state regulation unit 3000 may cool the cryogen. Alternatively, the cryogen state regulation unit 3000 may perform heating and/or cooling according to a state of the cryogen and keep a temperature of the cryogen. Alternatively, the cryogen state regulation unit 3000 may perform heating and/or cooling according to a state of the cryogen and keep a pressure of the cryogen.

As another example, the cryogen state regulation unit 3000 may regulate a speed of the cryogen. The cryogen state regulation unit 3000 may provide a space in which the cryogen expands, thereby decreasing the speed of the cryogen and decreasing the pressure of the cryogen. Alternatively, the cryogen state regulation unit 3000 may provide a space in which the cryogen is compressed, thereby increasing the speed of the cryogen and increasing the pressure of the cryogen.

1.3.2 Examples of Cryogen State Regulation Unit 3000

1.3.2.1 Cryogen Temperature Controller

According to an embodiment of the present application, the cryogen state regulation unit 3000 may include a cryogen temperature controller.

The cryogen temperature controller may perform a function of heating the cryogen. As a specific example, the cryogen temperature controller may perform a function of heating the cryogen and controlling the temperature and/or pressure of the cryogen.

The cryogen temperature controller may perform a function of cooling the cryogen. As a specific example, the cryogen temperature controller may perform a function of cooling the cryogen and controlling the temperature and/or pressure of the cryogen.

The cryogen temperature controller may perform a function of heating and cooling the cryogen. As a specific example, the cryogen temperature controller may perform a function of heating or cooling the cryogen to control the temperature and/or pressure of the cryogen.

The cryogen temperature controller according to an embodiment of the present application may include an element capable of supplying thermal energy.

The cryogen temperature controller may include one or more heating elements capable of generating thermal energy.

The heating element may generate thermal energy using chemical energy or generate thermal energy using electrical energy. Also, the heating element may generate thermal energy using the Joule-Thomson method which uses a condensable gas.

Alternatively, the heating element may also supply thermal energy using a thermoelectric element such as the Peltier element. In a case in which the heating element is a thermoelectric element, when current is applied to the thermoelectric element, due to the Peltier effect, an endothermic reaction may occur at a first side of the thermoelectric element and an exothermic reaction may occur at a second side of the thermoelectric element.

According to an embodiment of the present application, the cooling device 10000 in which a side corresponding to the second side of the thermoelectric element is disposed to thermally come into contact with a flow path through which the cryogen moves may be provided. Here, the thermoelectric element may serve as the cryogen temperature controller.

According to another embodiment of the present application, the control unit 5000 may reverse a direction of current applied to the thermoelectric element and control an endothermic reaction to occur at the second side of the thermoelectric element. Here, the cryogen flowing through the cryogen temperature controller may be cooled by the endothermic reaction by the thermoelectric element.

Therefore, when the thermoelectric element is applied to the cryogen temperature controller, the control unit 5000 may control a direction of current applied to the thermoelectric element and heat or cool the cryogen passing through the cryogen temperature controller.

According to an embodiment of the present application, the cooling device 10000 may include, as the cryogen temperature controller, a spraying temperature controller 3100 disposed between the flow regulation unit 2000 and the spraying unit 4000. The spraying temperature controller 3100 may perform a function of controlling a temperature of a cryogen discharged from the flow regulation unit 2000 and discharging the cryogen at the controlled temperature through the spraying unit 4000. A specific operation related thereto will be described in more detail below.

A cryogen cooling unit 3200 according to an embodiment of the present application may include an element capable of supplying cooling energy. The cryogen cooling unit 3200 may include one or more cooling elements capable of generating cooling energy.

The cooling element may generate cooling energy by using a Stirling cooler as the cooling device 10000, using a thermodynamic cycle such as a vapor compression refrigeration cycle, using evaporation of liquid, or using the Joule-Thomson method which uses an expanding gas. The cooling element may generate cooling energy by using liquid nitrogen or liquid carbon dioxide.

Alternatively, the cooling element may generate cooling energy using a thermoelectric element such as a Peltier element. The thermoelectric element is an element that performs cooling using the Peltier effect. Here, the Peltier effect refers to a phenomenon in which, when n- and p-type thermoelectric materials are paired and current is caused to flow therein, an exothermic reaction occurs at one side while an endothermic reaction (cooling) occurs at the other side. The Peltier effect, in other words, can be referred to as a heat-pump capable of electrical feedback control.

In a case in which the cooling element is a thermoelectric element, when current is applied to the thermoelectric element, due to the Peltier effect, an endothermic reaction may occur at a first side of the thermoelectric element, and an exothermic reaction may occur at a second side of the thermoelectric element.

According to an embodiment of the present application, the cooling device 10000 in which a side corresponding to the first side of the thermoelectric element is disposed to thermally come into contact with a flow path through which the cryogen moves may be provided. Here, the thermoelectric element may serve as the cryogen temperature controller.

The cryogen temperature controller according to an embodiment of the present application may further include a heat radiating element. The cryogen temperature controller according to an embodiment of the present application may further include an element for radiating thermal energy naturally generated when the cooling element generates an endothermic reaction.

According to an embodiment of the present application, the cooling device 10000 may include, as the cryogen temperature controller, the cryogen cooling unit 3200 disposed between the cryogen supply unit 1000 and the flow regulation unit 2000. The cryogen cooling unit 3200 may perform a function of cooling a cryogen received from the cryogen supply unit 1000 to control a pressure of the cryogen and allowing the cryogen with the controlled pressure to pass through the flow regulation unit 2000. A specific operation related thereto will be described in more detail below.

1.3.2.2 Cryogen Speed Controller

According to an embodiment of the present application, the cryogen state regulation unit 3000 may include a cryogen speed controller.

The cryogen speed controller may control a speed of the cryogen. The cryogen speed controller may control a speed at which the cryogen of the cooling device 10000 moves in a direction in which the cryogen is sprayed. As a more specific example, on the basis of a direction in which a fluid moves from the cryogen supply unit 1000 to the spraying unit 4000 of the cooling device 10000, the cryogen speed controller may control a speed at which the cryogen moves in one region of a moving path of the fluid.

The cryogen speed controller according to an embodiment of the present application may perform a function of providing a space in which the fluid may contract. When the cryogen passes through the cryogen speed controller, the cryogen may contract, and the speed and pressure of an expanded cryogen may increase. As the pressure of the expanded cryogen increases, the temperature of the cryogen may increase.

The cryogen speed controller according to an embodiment of the present application may perform a function of providing a space in which the fluid may expand. When the cryogen passes through the cryogen speed controller, the cryogen may expand, and the speed and pressure of the expanded cryogen may decrease. As the pressure of the expanded cryogen decreases, the temperature of the cryogen may decrease.

According to an embodiment of the present application, the cooling device 10000 may include, as the cryogen speed controller, a limited-capacity cryogen reservoir 3410 disposed between the reservoir 1100 and the valve 2100. The limited-capacity cryogen reservoir 3410 may perform a function of providing a space in which the cryogen discharging from the reservoir 1100 is accommodated by a predetermined volume and reducing fluctuations in the speed, pressure, and/or temperature of the cryogen flowing into the valve 2100. A specific operation related thereto will be described in more detail below.

1.4 Spraying Unit 4000

The spraying unit 4000 according to an embodiment of the present application may perform a function of discharging a fluid in the cooling device 10000 to the outside. The spraying unit 4000 according to an embodiment of the present application may perform a function of spraying a fluid in the cooling device 10000 to the outside. The spraying unit 4000 may perform a function of discharging the cryogen that passes through the cryogen supply unit 1000, the flow regulation unit 2000, and/or the cryogen state regulation unit 300 to the outside.

The spraying unit 4000 according to an embodiment of the present application may include a nozzle unit 4100. The nozzle unit 4100 may perform a function of jetting a cryogen flowing in at least one region in the cooling device 10000 to a free space.

The jetted cryogen may be in a gas-, liquid-, and/or solid-phase. In other words, the cryogen may be in a gas phase, a liquid phase, or a solid phase, or may be a mixture in which cryogens in at least two or more phases are distributed together. In an example, when the cryogen is $CO_2$, cryogens in a gas phase and a solid phase may be mixed and distributed together in the jetted cryogen. In another example, when the cryogen is $N_2$, cryogens in a gas phase and a liquid phase may be mixed and distributed together in the jetted cryogen.

The nozzle unit 4100 according to an embodiment of the present application may perform a function of providing a passage through which the cryogen in the cooling device 1000 may be discharged. For example, the nozzle unit 4100 may be a tube formed to allow the cryogen flowing in at least one region in the cooling device 10000 to be jetted to a free space.

The nozzle unit 4100 according to an embodiment of the present application may be a tube disposed at one end of a flow path formed in the cooling device 10000.

The nozzle unit 410 may include a tube having a relatively small cross-sectional area. The nozzle unit 4100 may include a tube having a relatively smaller cross-sectional area as compared with any one of the cryogen supply unit 1000, the flow regulation unit 2000, the cryogen state regulation unit 3000, and/or a pipe between the elements of the cooling device 10000.

The nozzle unit 4100 may have a wear-resistant characteristic. In other words, the nozzle unit 4100 may be formed of a material which is not damaged much due to friction. For example, the nozzle unit 4100 may be formed of an aluminum alloy, a steel alloy, stainless steel, or a copper alloy, but the material of the nozzle unit 4100 is not limited thereto.

According to an embodiment of the present application, the spraying unit 4000 may further include a spraying site limiting unit 4200 for limiting a region where the cryogen discharged from the spraying unit 4000 reaches.

According to an embodiment of the present application, the spraying site limiting unit 4200 may include a guide unit 4210 which serves as a barrier that prevents the cryogen from reaching a region other than the target region TR.

The guide unit 4210 may perform a function of limiting a region to which the cryogen is sprayed so that the region to which the cryogen is sprayed corresponds to the target region TR. The guide unit 4210 may perform a function of limiting a region to which the cryogen is sprayed so that the region to which the cryogen is sprayed corresponds to a surface area of the target region TR.

Here, the target region TR may be set to have a surface area suitable for the purpose of treatment. For example, when the purpose of cooling is to perform a cryoanesthetic function for injection, the target region TR may be set to have a surface area of an appropriate size which is large enough to find a site for injection treatment after cooling but does not cause discomfort to the patient due to excessive cold sensation caused by cooling an extremely large region.

For example, when performing a cryoanesthetic function for injection using the cooling device 10000, the guide unit 4210 may keep a surface area of the target region TR in a range of 1 $mm^2$ to 50 $mm^2$. As a specific example, the guide unit 4210 may keep the surface area of the target region TR in a range of 5 $mm^2$ to 20 $mm^2$. As a more specific example, the guide unit 4210 may keep the surface area of the target region TR in a range of 5 $mm^2$ to 10 $mm^2$.

The guide unit 4210 may be formed of a material having relatively low thermal conductivity. For example, the guide unit 4210 may be formed of a material having relatively low thermal conductivity as compared with the cryogen supply unit 1000, the flow regulation unit 2000, the cryogen state regulation unit 3000, and/or the nozzle unit 4100. As a specific example, the guide unit 4210 may be formed of a material having thermal conductivity lower than or equal to 20 W/m-K. For example, the guide unit 4210 may be formed of plastic, but the material of the guide unit 4210 is not limited thereto.

The guide unit 4210 may further include at least one hole. Through the hole formed in the guide unit 4210, an external gas may flow into an inner space of the guide unit 4210. Through the hole formed in the guide unit 4210, the cryogen discharged from the nozzle unit 4100 may be discharged to the outside of the spraying site limiting unit 4200. Through the hole formed in the guide unit 4210, the cryogen discharged from the nozzle unit 4100 may be discharged to the outside of the guide unit 4210.

The number of holes formed in the guide unit 4210 and the sizes and positions of the holes may affect the degree of inflow of the external gas. The number of holes formed in the guide unit 4210 and the sizes and positions of the holes may affect the time during which the cryogen discharged from the nozzle unit 4100 stays in the inner space of the spraying site limiting unit 4200. As a result, the number of holes formed in the guide unit 4210 and the sizes and positions of the holes may affect the extent at which the target region TR is cooled.

According to an embodiment of the present application, when the same amount of cryogen is sprayed from the spraying unit 4000 of the cooling device 10000, the temperature of the target region TR may be lower in a case in which cooling is performed using the cooling device 10000 in which the size of the hole formed in the guide unit 4210 is relatively small as compared with the case in which cooling is performed using the cooling device 10000 including the guide unit 4210 in which the size of the hole formed therein is relatively large. In other words, the smaller the size of the hole formed in the guide unit 4210, the smaller the amount of cryogen required to lower the temperature of the target region TR to a certain temperature.

According to an embodiment of the present application, in a case in which a plurality of holes are formed in the guide unit 4210, when the same amount of cryogen is sprayed from the spraying unit 4000 of the cooling device 10000, the temperature of the target region TR may be lower in a case in which cooling is performed using the cooling device 10000 in which the sum of the cross-sectional areas of the plurality of holes formed is relatively small as compared with the case in which cooling is performed using the cooling device 10000 in which the sum of the cross-sectional areas of the plurality of holes formed is relatively large. In other words, the smaller the sum of the cross-sectional areas of the plurality of holes formed in the guide unit 4210, the smaller the amount of cryogen required to lower the temperature of the target region TR to a certain temperature.

According to an embodiment of the present application, the number of holes in the guide unit 4210 and the sizes and positions thereof may be determined to an extent that the efficiency of the cooling device 10000 is not significantly degraded. As a specific example, the guide unit 4210 of the cooling device 10000 may be formed such that the sum of the cross-sectional areas of the holes is less than 100 mm$^2$.

Also, the number of holes formed in the guide unit 4210 and the sizes and positions thereof may affect the extent at which the target region TR is cooled and may affect the phase of the cryogen discharged to the outside via the hole formed in the guide unit 4210. In a preferred embodiment, the hole formed in the guide unit 4210 may have the size and position that allows 90% or more by volume of the cryogen discharged to the outside through the hole formed in the guide unit 4210 to be in a gas phase. Accordingly, it is possible to derive the effect of facilitating discharge of the cryogen through the hole. As a specific example, the guide unit 4210 of the cooling device 10000 may be formed such that the sum of the cross-sectional areas of the holes is greater than 10 mm$^2$.

According to an embodiment of the described technology, the guide unit 4210 may perform a function of applying a pressure to a region related to the target region TR. The guide unit 4210 may perform a function of applying a pressure to at least a partial region of the target region TR. The guide unit 4210 may perform a function of applying a pressure to a barrier region of the target region TR.

According to an embodiment of the present application, the guide unit 4210 may perform a function of, w % ben coming into contact with a surface of the target region TR, further applying a pressure due to contact to one region related to the target region TR. For example, the guide unit 4210 may use its physical shape to apply a pressure to one region related to the target region TR.

The pressure applied by the guide unit 4210 leaves a mark on the one region even after the guide unit 4210 is separated and removed from the target region TR. In this way, it is possible to derive the effect of allowing the cooled region to be easily recognized when performing injection after cooling is performed by the cooling device 10000.

Figure 5:
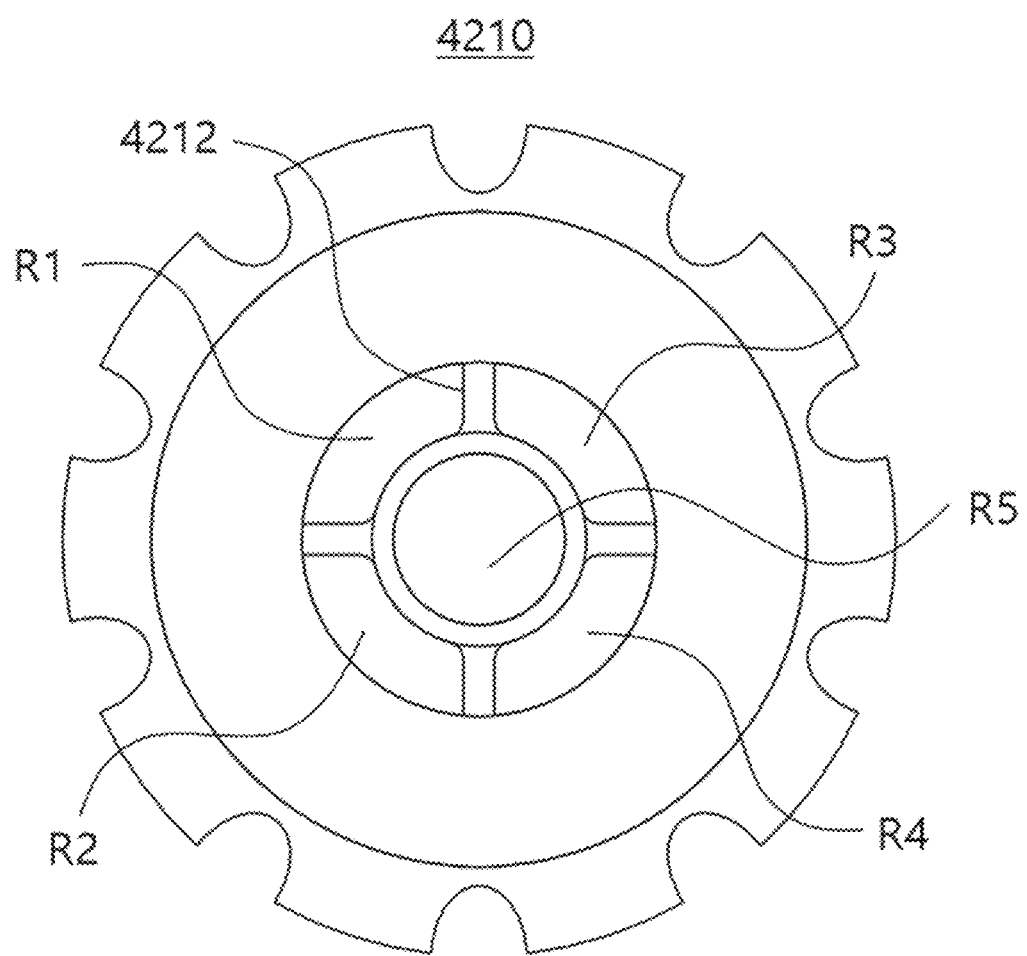
FIG. 5 is a view for describing a guide unit according to an embodiment of the present application.

FIG. 5 is a view for describing the guide unit 4210 according to an embodiment of the present application.

The guide unit 4212 may come into contact with one region related to the target region TR when the cooling device 10000 sprays a cryogen. The guide unit 4212 may come into contact with one region of the target region TR when the cooling device 10000 sprays the cryogen. The guide unit 4212 may come into contact with a barrier region of the target region TR when the cooling device 10000 sprays the cryogen.

FIG. 5 is a view of the guide unit 4212 viewed from the side when the guide unit 4212 comes into contact with the target region TR at a time point when the cooling device 10000 performs cooling.

The cooling device 10000 may include the guide unit 4212 including a region formed to allow the cryogen to pass therethrough and be sprayed to one surface of the target region TR. The cooling device 10000 may include the guide unit 4212 including a through-hole formed to allow the cryogen to pass therethrough and be sprayed to one surface of the target region TR.

According to an embodiment of the present application, the guide unit 4212 may include a first region R1, a second region R2, a third region R3, a fourth region R4, and a fifth region R5. The cryogen sprayed from the nozzle unit 4100 of the cooling device 10000 may be sprayed to one surface of the target region TR through at least one of the first region R1 to the fifth region R5 of the guide unit 4212.

According to an embodiment of the present application, the first region R1 to the fifth region R5 may be implemented in the form of being separated by a marking unit 4212.

The marking unit 4212 may perform a function of leaving a mark on one region related to the target region TR. In other words, when cooling is performed by the cooling device 10000, the guide unit 4212 may come into contact with the target region TR, and, here, a pressure due to spraying the cryogen and a pressure due to contact with the guide unit 4212 may be applied to one surface of the target region TR. Therefore, when the guide unit 4212 comes into contact with the target region TR, the marking unit 4212 formed at a side of the guide unit 4212 coming into contact with the target region TR may apply a pressure due to contact to the target region TR. When the marking unit 4212 has a cross shape with a circle in the center, the marking unit 4212 may leave a mark, which corresponds to the cross shape with the circle in the center, on the target region TR.

When cooling is performed by the cooling device 10000 including the guide unit 4212 having the marking unit 4212, it is possible to derive the effect of allowing the cooled region to be easily recognized when performing injection after cooling is performed.

According to an embodiment of the present application, the spraying site limiting unit 4200 may further include a heat providing barrier 4220 configured to provide heat to a region other than the target region TR in order to limit a region where the cryogen discharged from the nozzle unit 4100 reaches.

The heat providing barrier 4220 according to an embodiment of the present application may use convection to supply heat to the barrier of the target region TR and perform a function of discharging a heated fluid to a region other than the target region TR. The heated fluid may come into contact with a region other than the target region TR and provide heat to the region other than the target region TR.

The heat providing barrier 4220 according to an embodiment of the present application may use conduction to supply heat to the barrier of the target region TR and perform a function of causing a heating element to come into contact with a region other than the target region TR. The heating element may come into contact with the region other than the target region TR and provide heat to the region other than the target region TR.

The heat providing barrier 4220 according to an embodiment of the present application may use radiation to supply heat to the barrier of the target region TR and perform a function of providing light to a region other than the target region TR.

The light may be provided to the region other than the target region TR and provide heat to the region other than the target region.

1.5 Control Unit 5000

The control unit 5000 according to an embodiment of the present application may perform a function of controlling operations of the elements of the cooling device 10000. The control unit 5000 may perform a function of controlling the cryogen supply unit 1000, the flow regulation unit 2000, the cryogen state regulation unit 3000, and/or the spraying unit 4000.

The control unit 5000 according to an embodiment of the present application may be implemented using a computer or a device similar thereto according to hardware, software, or a combination thereof. In terms of hardware, the control unit 5000 may be provided in the form of an electronic circuit such as a central processing unit (CPU) chip that processes an electrical signal and performs a control function. In terms of software, the control unit 5000 may be provided in the form of a program for driving the hardware of the control unit 5000.

The control unit 5000 according to an embodiment of the present application may control driving of the flow regulation unit 2000. As a more specific example, the control unit 5000 may control opening and closing of the valve 2100 and control the opening and closing of the valve 2100 to have a repetitive cycle as necessary. A specific embodiment related thereto will be described in more detail below.

The control unit 5000 according to an embodiment of the present application may control driving of the cryogen state regulation unit 3000. As a more specific example, the control unit 5000 may control whether a heating element is driven and control the on/off of the heating element in consideration of association with the opening and closing of the valve 2100 as necessary. A specific embodiment related thereto will be described in more detail below.

The control unit 5000 according to an embodiment of the present application may be implemented as a single control unit. The control unit 5000 according to another embodiment of the present application may be implemented as a plurality of control units.

Here, the cooling device 10000 including the control unit 5000 which includes a plurality of control units may be interpreted as the cooling device 10000 having a first control unit and a second control unit which operate independently. The first control unit may perform control related to at least a first function, and the second control unit may perform control related to at least a second function.

As a specific example, the first control unit may generally control a function of controlling the opening/closing of the valve 2100 when a cooling operation is performed by the cooling device 10000. The second control unit may control an operation for blocking a flow of a cryogen to be performed when a temperature in at least one region of a flow path through which the cryogen flows decreases to a predetermined temperature or lower when the cooling operation is performed by the cooling device 10000. Here, the second control unit may also block the flow of the cryogen by performing an operation of closing the valve 2100. Since the second control unit which operates independently of the first control unit provides a means capable of preventing supercooling, it is possible to provide the cooling device 10000 that ensures safety of a subject receiving treatment even when the first control unit of the cooling device 10000 malfunctions.

The elements of the cooling device 10000 according to an embodiment of the present application have been described above. However, the above description does not indicate that the cooling device 10000 according to the present application only includes the above elements. Although not illustrated, the cooling device 10000 may further include an input unit 6300 configured to receive a user input, an output unit configured to output specific information to a user, a temperature measuring unit configured to measure a temperature in one region of the cooling device 10000, a filter 6200 configured to filter impurities of a cryogen flowing through the cooling device 10000, and the like.

Hereinafter, the connection relations between the elements of the cooling device 10000 according to an embodiment of the present application and the arrangement of the elements will be described in detail.

2. Structure of Cooling Device 10000

The cooling device 10000 according to an embodiment of the present application may be implemented in the form of being integrated with the reservoir 1100 so as to be provided as a portable device. Alternatively, the cooling device 10000 according to an embodiment of the present application may be implemented in the form of a handpiece having a part connected to an external tank so as to be used by being connected to the external tank.

The cooling device 10000 according to an embodiment of the present application may include at least one element of the above-described cryogen supply unit 1000, flow regulation unit 2000, cryogen state regulation unit 3000, spraying unit 4000, and control unit 5000.

For example, the cooling device 10000 may include the cryogen supply unit 1000, the flow regulation unit 2000, the spraying unit 4000, and control unit 5000. The cooling device 10000 according to an embodiment of the present application may form a flow path by the cryogen supply unit 1000, the flow regulation unit 2000, and the spraying unit 4000 connected in that order, and the control unit 5000 may be implemented to control at least the flow regulation unit 2000.

As another example, the cooling device 10000 may include the cryogen supply unit 1000, the flow regulation unit 2000, the cryogen state regulation unit 3000, the spraying unit 4000, and the control unit 5000. The cooling device 10000 according to an embodiment of the present application may form a flow path by the cryogen supply unit 1000, the flow regulation unit 2000, the cryogen state regulation unit 3000, and the spraying unit 4000 connected in that order, and the control unit 5000 may be implemented to control at least the flow regulation unit 2000 and the cryogen state regulation unit 3000.

The cooling device 10000 according to an embodiment of the present application may include at least one element of the above-described cryogen supply unit 1000, flow regulation unit 2000, cryogen state regulation unit 3000, spraying unit 4000, and control unit 5000 in a plurality. For example, the cooling device 10000 may include at least two valves 2100 as flow regulation units 2000. As another example, the cooling device 10000 may include at least two cryogen cooling units 3200.

The cooling device 10000 according to an embodiment of the present application may include at least one element of the above-described cryogen supply unit 1000, flow regulation unit 2000, cryogen state regulation unit 3000, spraying unit 4000, and control unit 5000 in a plurality. Here, a plurality of a certain element may each perform a different function.

For example, the cooling device 10000 may include at least the valve 2100 and the flow-rate restriction unit 2200 as flow regulation units 2000. The cooling device 10000 according to an embodiment of the present application may form a flow path by the cryogen supply unit 1000, the flow-rate restriction unit 2200, the valve 2100, and the nozzle unit 4100 connected in that order, and the control unit 5000 may be implemented to control at least the valve 2100.

As another example, the cooling device 10000 may include at least the cryogen cooling unit 3200 and the spraying temperature controller 3100 as cryogen state regulation units 3000. The cooling device 10000 according to an embodiment of the present application may form a flow path by the cryogen supply unit 1000, the cryogen cooling unit 3200, the valve 2100, the spraying temperature controller 3100, and the nozzle unit 4100 connected in that order, and the control unit 5000 may be implemented to control at least the valve 2100, the cryogen cooling unit 3200, and the spraying temperature controller 3100.

The cooling device 10000 according to an embodiment of the present application may be implemented as various forms of housings.

For example, the cooling device 10000 may have an elongated body (not illustrated). In a case in which the cooling device 10000 according to an embodiment of the present application has an elongated body, all of the elements of the cooling device 10000 may be disposed in the elongated body extending in a first direction. According to an embodiment of the present application, the elements of the cooling device 10000 disposed in the elongated body may be arranged in an order consistent with the direction of movement of a fluid.

Figure 6:
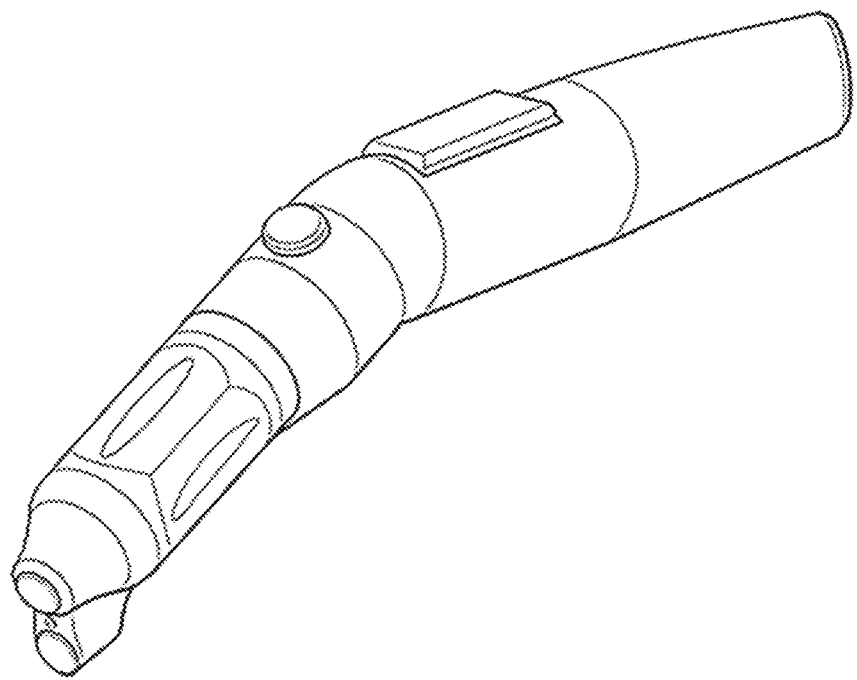
FIGS. 6 and 7 are views for describing a housing of the cooling device according to an embodiment of the present application.

As another example, the cooling device 10000 may have a C-shaped body (see FIG. 6). In a case in which the cooling device 10000 according to an embodiment of the present application has a C-shaped body, all of the elements of the cooling device 10000 may be disposed in the C-shaped body. According to an embodiment of the present application, the elements of the cooling device 10000 disposed in the C-shaped body may be arranged in an order consistent with the direction of movement of a fluid.

Figure 7:
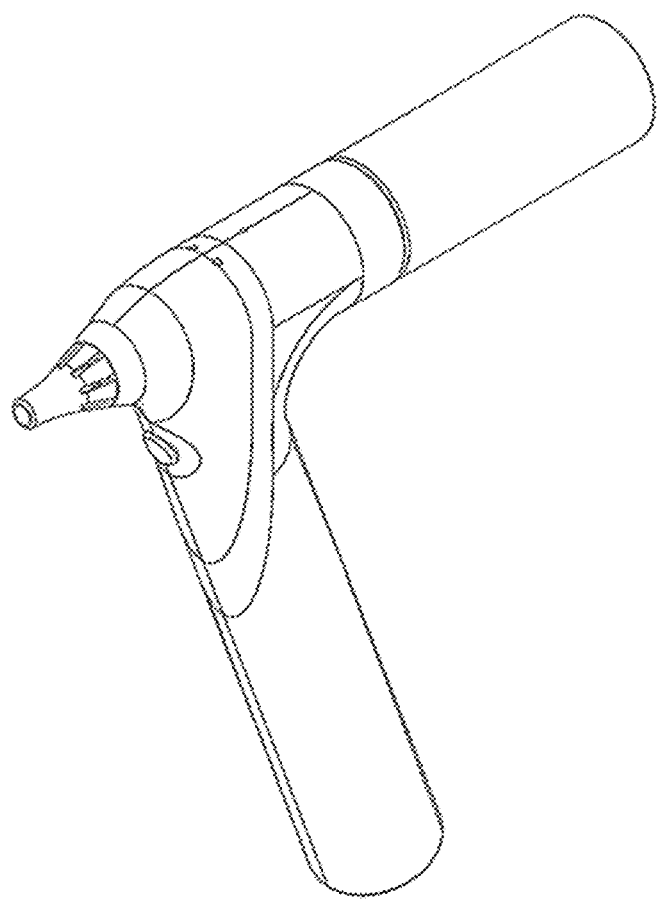

As still another example, the cooling device 10000 may have a T-shaped body (see FIG. 7). In a case in which the cooling device 10000 according to an embodiment of the present application has a T-shaped body, all of the elements of the cooling device 10000 may be disposed in a region of the T-shaped body extending in the first direction. Alternatively, in the case in which the cooling device 10000 according to an embodiment of the present application has a T-shaped body, some of the elements of the cooling device 10000 may be disposed in the region of the T-shaped body extending in the first direction, and the remaining elements may be disposed in a region of the T-shaped body extending in a second direction.

In addition, the cooling device 10000 may be formed in a pen shape, a pistol shape, a polygonal shape, or other shapes for ease of operation during use. Also, the cooling device 10000 may provide a gripping portion that may be gripped by a user. Also, the cooling device 10000 may be formed in a non-elongated structure. The non-elongated structure may include an open structure, a closed structure, a polygonal structure, and a curved structure.

The cooling device 10000 according to some embodiments of the present application has been described in detail above. However, the above-described embodiments only disclose specific embodiments for assisting in understanding of the present specification, and thus the scope of the present application should be determined on the basis of the claims below.

Hereinafter, operations that may be performed by the cooling device 10000 according to an embodiment of the present application will be disclosed in detail.

However, in describing specific operations of the cooling device 10000, for convenience of description, unless there is a specific limitation, the electronic valve 2100 that performs opening and closing in response to an electrical signal will be specified and described as the flow regulation unit 2000, a thermoelectric element that is capable of performing cooling and/or heating according to applied current will be specified and described as the cryogen state regulation unit 3000, and the reservoir 1100 that is mounted on the cooling device 10000 and supplies a cryogen will be specified and described as the cryogen supply unit 1000.

However, such an example of the cooling device 10000 is described only to prevent unnecessary redundant description, and it should be interpreted that any other examples of the cooling device 10000 disclosed by the present application can perform the following operations.

<Operations of Cooling Device 10000>

1. Cooling Control 1.1 Cooling Control

Figure 8:
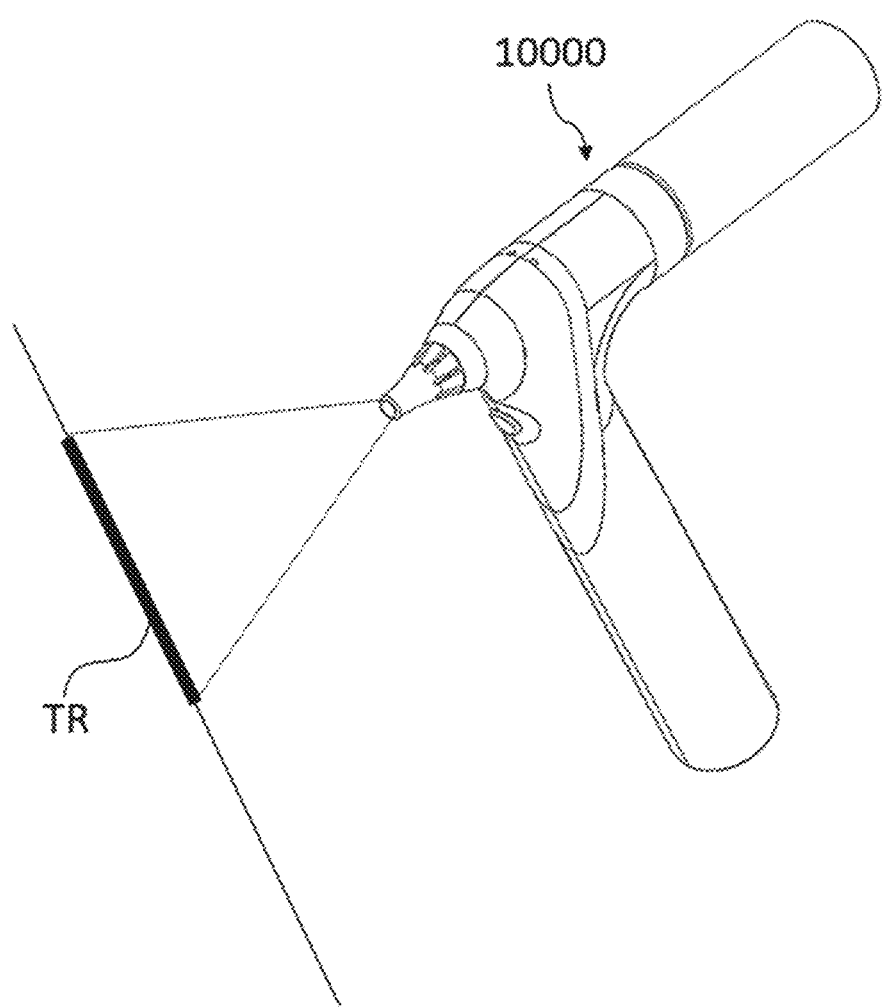
FIG. 8 is a conceptual diagram for describing cooling of the cooling device according to an embodiment of the present application.

FIG. 8 is a conceptual diagram for describing cooling of the cooling device 10000 according to an embodiment of the present application.

The cooling device 10000 according to an embodiment of the present application may perform a function of discharging a cryogen and cooling a target region TR. The cooling device 10000 may discharge a cryogen through the nozzle unit 4100 and cool the target region TR.

When the cryogen is discharged from the cooling device 10000, heat loss may occur in the target region TR, and the target region TR may be cooled. As described above, at least one phenomenon of radiation, conduction, and/or convection may occur in the target region TR, and, when the cryogen is discharged from the cooling device 10000, the target region TR may be cooled.

The extent at which the target region TR is cooled and/or the speed of cooling may be determined by the temperature of the cryogen being discharged from the cooling device 10000 and/or the amount of the cryogen.

Hereinafter, an operation of the cooling device 10000 for controlling the temperature of the cryogen discharged from the cooling device 10000 and/or the amount of the cryogen will be described in detail.

1.2 Examples of Cooling Control 1.2.1 Cooling Control Through Flow Control

A flow-rate of discharge of the cryogen from the cooling device 10000 according to an embodiment of the present application may be regulated by the control unit 5000. For example, the control unit 5000 may control the valve 2100 and regulate the flow-rate of discharge of the cryogen.

As a specific example, the control unit 5000 of the cooling device 10000 according to an embodiment of the present application may output a first signal for opening the valve 2100 during a first time and output a second signal for closing the valve 2100 after the first time elapses.

The control unit 5000 of the cooling device 10000 according to an embodiment of the present application may control the amount of the cryogen discharged from the cooling device 10000. In order to control the amount of the cryogen being discharged, the control unit 5000 may control an opening time of the valve 2100. As the opening time of the valve 2100 is increased, the temperature of the target region TR may be relatively further decreased.

As a specific example, the control unit 5000 of the cooling device 10000 according to an embodiment of the present application may open the valve 2100 during the first time in order to cool the target region TR to a first temperature. The control unit 5000 may open the valve 2100 during a second time, which is longer than the first time, in order to cool the target region TR to a second temperature lower than the first temperature.

The operation of discharging the cryogen from the cooling device 10000 according to an embodiment of the present application may be controlled by the control unit 5000.

The control unit 5000 of the cooling device 10000 according to an embodiment of the present application may control the valve 2100 to reach at least a first state and a second state multiple times in order to perform one cooling. The control unit 5000 may control the valve 2100 to repeatedly reach the first state and the second state periodically. Alternatively, the control unit 5000 may control the valve 2100 to repeatedly reach the first state and the second state non-periodically.

For example, the first state may be a state in which the cryogen is beign discharged through the valve 2100, and the second state may be a state in which the discharge of the cryogen through the valve 2100 is blocked.

As a specific embodiment, in the case of the cooling device 100M which is configured to repeatedly perform discharge of the cryogen through the valve 2100 and blockage of the cryogen discharge, as the cryogen discharges and stops discharging due to opening and closing of the valve 2100, spraying the cryogen and stopping the spraying of the cryogen may be repeated by the spraying unit 4100.

As another specific embodiment, in the case of the cooling device 10000 which is configured to repeatedly perform discharge of the cryogen through the valve 2100 and blockage of the cryogen discharge, although the valve 2100 is in a completely-closed state, the cryogen remaining in a flow path formed from the valve 2100 to the nozzle unit 4100 may discharge through the nozzle unit 4100, and thus spraying of a large amount of cryogen and spraying of a relatively smaller amount of cryogen may be repeated by the spraying unit 4100.

As another example, the first state may be a state in which a cryogen discharges through the valve 2100 as much as a first flow-rate per unit time, and the second state may be a state in which a cryogen discharges through the valve 2100 as much as a second flow-rate per unit time. Here, the first flow-rate may be a flow different from the second flow-rate.

As a more specific embodiment, the second state in which the cryogen discharges as much as the second flow-rate instead of being completely blocked through the valve 2100 may be implemented by providing at least one of the valve 2100 and the reservoir 1100 in a plurality and causing the cryogen to discharge as much as the second flow-rate from one of the plurality of valves 2100 or one of the plurality of reservoirs 1100.

As another specific embodiment, the second state in which the cryogen discharges as much as the second flow-rate instead of being completely blocked through the valve 2100 may be implemented by causing the cryogen to discharge as much as the second flow-rate using the valve 2100 which may be controlled, according to circumstances, to reach a closed state, a state in which the cryogen discharges as much as the first flow-rate, and a state in which the cryogen discharges as much as the second flow-rate.

Figure 9:
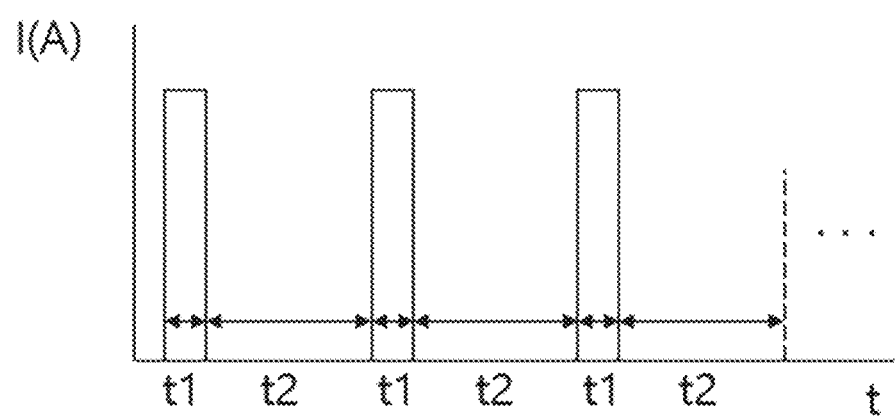
FIGS. 9, 10 and 11 are views for describing a cooling control operation of the cooling device according to an embodiment of the present application.
Figure 10:
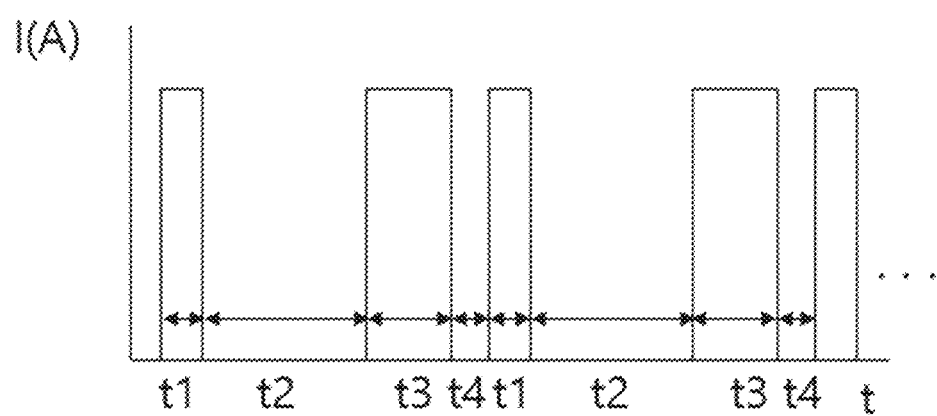
Figure 11:
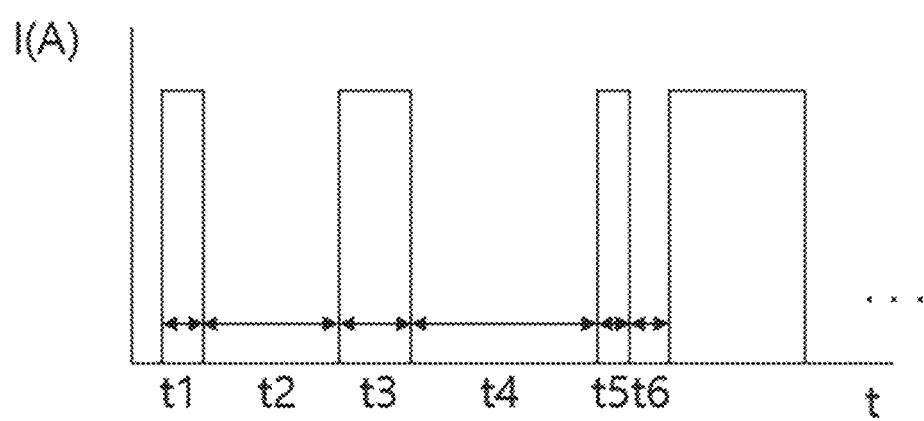

FIGS. 9 to 11 are views for describing a cooling control operation of the cooling device 10000 according to an embodiment of the present application.

Referring to FIG. 9, the control unit 5000 may control the valve 2100 to repeatedly reach a first state and a second state periodically.

Here, in a case in which the first state is a state in which the cryogen is being discharged through the valve 2100, and the second state is a state in which the discharge of the cryogen through the valve 2100 is being blocked, the control unit 5000 may control the valve 2100 to be in an open state during a first time and control the valve 2100 to be in a closed state during a second time. As a result, the control unit 5000 may control the valve 2100 to repeat the opening and closing operations a predetermined number of times.

Here, in a case in which the first state is a state in which a cryogen is being discharged through the valve 2100 as much as a first flow-rate per unit time, and the second state is a state in which a cryogen is being discharged through the valve 2100 as much as a second flow-rate, which is lower than the first flow-rate, per unit time, the control unit 5000 may control the valve 2100 to keep the first state during a first time t1 (hereinafter referred to as "first control"), control the valve 2100 to keep the second state during a second time t2 (hereinafter referred to as "second control"), and repeatedly perform the first control and the second control a predetermined number of times.

According to an embodiment of the present application, in a case in which the control unit 5000 repeatedly performs the first control and the second control a predetermined number of times, the first time t1 may be shorter than the second time t2.

Referring to FIG. 10, the control unit 5000 may control the valve 2100 to repeatedly reach the first state and the second state periodically. The control unit 5000 may control the valve 2100 so that the valve 2100 keeps the first state at least during the first time t1 and a third time t3 and keeps the second state at least during the second time t2 and a fourth time t4.

Here, in a case in which the first state is a state in which the cryogen is being discharged through the valve 2100, and the second state is a state in which the discharge of the cryogen through the valve 2100 is being blocked, the control unit 5000 may control the valve 2100 to be in the open state during the first time t1, control the valve 2100 to be in the closed state during the second time t2, control the valve 2100 to be in the open state during the third time t3, and control the valve 2100 to be in the closed state during the fourth time 4. As a result, the control unit 5000 may control the valve 2100 to repeat the opening corresponding to the first time t1, the closing corresponding to the second time t2, the opening corresponding to the third time t3, and the closing corresponding to the fourth time t4 a predetermined number of times.

Here, in a case in which the first state is a state in which a cryogen is being discharged through the valve 2100 as much as the first flow-rate per unit time, and the second state is a state in which a cryogen is being discharged through the valve 2100 as much as the second flow-rate, which is lower than the first flow-rate, per unit time, the control unit 5000 may control the valve 2100 to keep the first state during the first time t1 (hereinafter referred to as "first control"), control the valve 2100 to keep the second state during the second time t2 (hereinafter referred to as "second control"), control the valve 2100 to keep the first state during the third time t3 (hereinafter referred to as "third control"), and control the valve 2100 to keep the second state during the fourth time t4 (hereinafter referred to as "fourth control"). The control unit 5000 may repeatedly perform the first control, the second control, the third control, and the fourth control a predetermined number of times.

Referring to FIG. 11, the control unit 5000 may control the valve 2100 to repeatedly reach the first state and the second state non-periodically.

Here, in a case in which the first state is a state in which the cryogen is being discharged through the valve 2100, and the second state is a state in which the discharge of the cryogen through the valve 2100 is being blocked, the control unit 5000 may control the valve 2100 to be in the open state during the first time t1, control the valve 2100 to be in the closed state during the second time t2, control the valve 2100 to be in the open state during the third time t3, control the valve 2100 to be in the closed state during the fourth time t4, control the valve 2100 to be in the open state during a fifth time t5, and control the valve 2100 to be in the closed state during a sixth time t6. The first time t1 and the fifth time 5 may be different.

Here, in a case in which the first state is a state in which the cryogen is being discharged through the valve 2100, and the second state is a state in which the discharge of the cryogen through the valve 2100 is being blocked, the control unit 5000 may control the valve 2100 to be in the open state during the first time t1, control the valve 2100 to be in the closed state during the second time t2, control the valve 2100 to be in the open state during the third time t3, control the valve 2100 to be in the closed state during the fourth time t4, control the valve 2100 to be in the open state during the fifth time t5, and control the valve 2100 to be in the closed state during the sixth time t6. The second time t2 and the sixth time t6 may be different.

Here, in a case in which the first state is a state in which a cryogen is being discharged through the valve 2100 as much as the first flow-rate per unit time, and the second state is a state in which a cryogen is being discharged through the valve 2100 as much as the second flow-rate, which is lower than the first flow, per unit time, the control unit 5000 may control the valve 2100 to keep the first state during the first time t1 (hereinafter referred to as "first control"), control the valve 2100 to keep the second state during the second time t2 (hereinafter referred to as "second control"), control the valve 2100 to keep the first state during the third time t3 (hereinafter referred to as "third control"), control the valve 2100 to keep the second state during the fourth time t4 (hereinafter referred to as "fourth control"), control the valve 2100 to keep the first state during the fifth time t5 (hereinafter referred to as "fifth control"), and control the valve 2100 to keep the second state during the sixth time t6 (hereinafter referred to as "sixth control"). The first time t1 and the fifth time t5 may be different.

Here, in a case in which the first state is a state in which a cryogen is being discharged through the valve 2100 as much as the first flow-rate per unit time, and the second state is a state in which a cryogen is being discharged through the valve 2100 as much as the second flow-rate, which is lower than the first flow-rate, per unit time, the control unit 5000 may control the valve 2100 to keep the first state during the first time t1 (hereinafter referred to as "first control"), control the valve 2100 to keep the second state during the second time t2 (hereinafter referred to as "second control"), control the valve 2100 to keep the first state during the third time 3 (hereinafter referred to as "third control"), control the valve 2100 to keep the second state during the fourth time t4 (hereinafter referred to as "fourth control"), control the valve 2100 to keep the first state during the fifth time t5 (hereinafter referred to as "fifth control"), and control the valve 2100 to keep the second state during the sixth time t6 (hereinafter referred to as "sixth control"). The second time t2 and the sixth time t6 may be different.

The control unit 5000 of the cooling device 10000 according to an embodiment of the present application may control the valve 2100 on the basis of the amount of cryogen discharged during a predetermined time.

For example, in a case in which the first state is a state in which the valve 2100 is open and the second state is a state in which the valve 2100 is closed, the cooling device 10000 may control the valve 2100 so that the sum of times corresponding to the first state does not exceed a predetermined time. In a preferred embodiment of the described technology, the control unit 5000 may control the first time t1 constituting the first state not to exceed 10 seconds. More specifically, the control unit 5000 may control the first time t1 constituting the first state not to exceed 5 seconds. The control unit 5000 may control the first time t1 constituting the first state not to exceed 2 seconds. The control unit 5000 may control the first time t1 constituting the first state not to exceed 1 second. The control unit 5000 may control the first time t1 constituting the first state not to exceed 0.5 second. The control unit 5000 may control the first time t1 constituting the first state not to exceed 0.1 second.

As another example, in a case in which an amount of cryogen discharged from the cooling device 10000 in the first state is different from an amount of cryogen discharged from the cooling device 10000 in the second state, the cooling device 10000 may control the valve 2100 so that the sum of a first value, which is obtained by multiplying a time corresponding to the first state by the amount of cryogen discharged from the cooling device 10000 per unit time in the first state, and a second value, which is obtained by multiplying a time corresponding to the second state by the amount of cryogen discharged from the cooling device 10000 per unit time in the second state, does not exceed a predetermined value.

The operation of controlling the on/off of the valve 2100 has been described in detail above as a cooling control method of the cooling device 10000 according to an embodiment of the present application.

Hereinafter, a phenomenon that occurs according to controlling the valve 2100 to reach the first state and the second state multiple times periodically during a predetermined time as described above will be described in detail.

For convenience of description, a case in which the first state is an open state and the second state is a closed state will be described as an example. However, the first state and the second state may be any other states that may be easily derived by those of ordinary skill in the art as long as the flow-rate of discharge of the cryogen per unit time is different in the first state and the second state.

Figure 12:
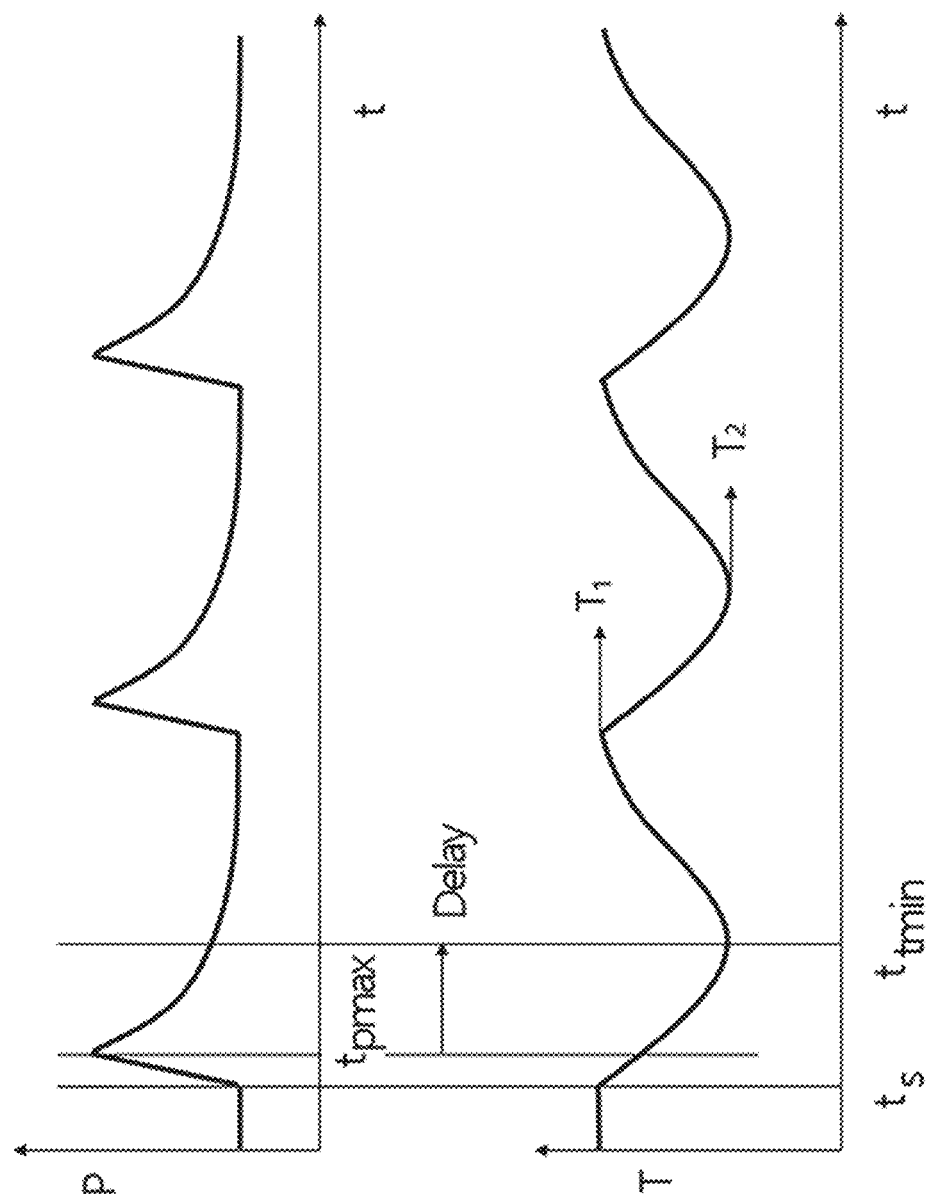
FIG. 12 shows a graph of pressure over time and a graph of temperature over time in a target region TR according to a control method of the cooling device according to an embodiment of the present application.

FIG. 12 shows a graph of pressure over time and a graph of temperature over time in a target region TR according to a control method of the cooling device 10000 according to an embodiment of the present application.

The graph of pressure over time that is shown at the top of FIG. 12 shows a graph of pressure applied to the target region TR over time as the cryogen is sprayed to the target region TR when cooling of the target region TR is performed using the cooling device 10000 according to an embodiment of the present application.

Referring to the graph of pressure over time that is shown at the top of FIG. 12, in a case in which the control unit 5000 of the cooling device 10000 controls the valve 2100 to reach the first state and the second state multiple times, a curve indicating the pressure over time in the target region TR may be a curve in which the pressure repeats increasing, decreasing, and unchanging.

The graph of temperature over time that is shown at the bottom of FIG. 12 shows a graph of temperature of the target region TR over time as the cryogen is sprayed to the target region TR when cooling of the target region TR is performed using the cooling device 10000 according to an embodiment of the present application.

Referring to the graph of temperature over time that is shown at the bottom of FIG. 12, in a case in which the control unit 5000 of the cooling device 10000 controls the valve 2100 to repeatedly reach the first state and the second state, a curve indicating the temperature over time in the target region TR may be a curve in which the temperature repeats decreasing, increasing, and unchanging.

In a case in which the target region TR is cooled using the cooling device 10000 according to an embodiment of the present application, although the pressure and temperature relate to the same target region TR, a time difference may occur between a maximum pressure time point $t_{Pmax}$, which corresponds to the maximum pressure in the pressure curve, and a minimum temperature time point $t_{Tmin}$, which corresponds to the minimum temperature in the temperature curve.

In a case in which the control unit 5000 according to an embodiment of the present application controls the valve 2100 to reach the first state, in relation to the target region TR, the minimum temperature time point $t_{Tmin}$, which corresponds to the minimum temperature in the curve indicating the temperature over time, may be delayed compared to the maximum pressure time point $t_{Pmax}$, which corresponds to the maximum pressure in the curve indicating the pressure over time.

In a case in which the control unit 5000 according to an embodiment of the present application controls the valve 2100 to reach the first state and the second state multiple times, during one time in which the valve is kept at the first state, the minimum temperature time point $t_{Tmin}$ of the target region TR may be delayed by a predetermined time compared to the maximum pressure time point $t_{Pmax}$.

The time difference between the maximum pressure time point $t_{Pmax}$ and the minimum temperature time point $t_{Tmin}$ according to an embodiment of the present application may be determined according to a cycle in which the first state and the second state are repeated and the amount of cryogen sprayed in the first state. As a specific example, a time difference $(t_{Tmin}\text{-}t_{Pmax})$ between the maximum pressure time point $t_{Pmax}$, and the minimum temperature time point $t_{Tmin}$, may be between 0.1 times and 0.9 times the cycle of repeating the first state and the second state. The control unit 5000 may control the valve 2100 so that the time difference $(t_{Tmin}\text{-}t_{Pmax})$ between the maximum pressure time point $t_{Pmax}$, and the minimum temperature time point $t_{Tmin}$ is between 0.1 times and 0.9 times the cycle of repeating the first state and the second state. As a more specific example, the time difference $(t_{Tmin}\text{-}t_{Pmax})$ may be between 0.2 times and 0.8 times the cycle of repeating the first state and the second state. As a more specific example, the time difference $(t_{Tmin}\text{-}t_{Pmax})$ may be between 0.3 times and 0.7 times the cycle of repeating the first state and the second state. As a more specific example, the time difference $(t_{Tmin}\text{-}t_{Pmax})$ may be between 0.4 times and 0.6 times the cycle of repeating the first state and the second state.

Regarding the cooling device 10000 according to an embodiment of the present application, the time difference between the maximum pressure time point $t_{Pmax}$, and the minimum temperature time point $t_{Tmin}$ may be determined according to thermal diffusivity in the target region TR on which the cooling device 10000 is used. In other words, the higher the thermal diffusivity in the target region TR, the smaller the time difference between the maximum pressure time point $t_{Pmax}$ and the minimum temperature time point $t_{Tmin}$.

In a preferred embodiment of the described technology, in a case in which cooling is performed by controlling the valve 2100 to reach the first state and the second state multiple times, the control unit 5000 may control a time difference $(t_{Tmin}\text{-}t_s)$ between a time point $t_s$ at which the cryogen reaches the target region TR and the minimum temperature time point $t_{Tmin}$ so that a difference $(T_1\text{-}T_2)$ between the maximum temperature $T_1$ and the minimum temperature $T_2$ is controlled to 30° C. or lower. The control of the time difference $(t_{Tmin}\text{-}t_s)$ between the time point is at which the cryogen reaches the target region TR and the minimum temperature time point $t_{Tmin}$ may be performed through controlling the valve 2100. As a more specific example, the control unit 5000 may control the time difference $(t_{Tmin}\text{-}t_s)$ so that the temperature difference $(T_1\text{-}T_2)$ is controlled to 20° C. or lower. As a more specific example, the control unit 5000 may control the time difference $(t_{Tmim}\text{-}t_s)$ so that the temperature difference $(T_1\text{-}T_2)$ is controlled to 10° C. or lower. As a more specific example, the control unit 5000 may control the time difference $(t_{Tmim}\text{-}t_s)$ so that the temperature difference $(T_1\text{-}T_2)$ is controlled to 5° C. or lower. As a more specific example, the control unit 5000 may control the time difference $(t_7m\text{-}t_s)$ so that the temperature difference $(T_1\text{-}T_2)$ is controlled to 3° C. or lower.

In another preferred embodiment of the described technology, the control unit 5000 may control a time difference $(t_{Pmax}\text{-}t_s)$ between the time point is at which the cryogen reaches the target region TR and the maximum pressure time point $t_{Pmax}$ so that the difference $(T_1\text{-}T_2)$ between the maximum temperature $T_1$ and the minimum temperature $T_2$ is controlled to 30° C. or lower. The control of the time difference $(t_{Pmax}\text{-}t_s)$ between the time point $t_s$ at which the cryogen reaches the target region TR and the maximum pressure time point $t_{Pmax}$ may be performed through controlling the valve 2100. As a more specific example, the control unit 5000 may control the time difference $(t_{Pmax}\text{-}t_s)$ so that the temperature difference $(T_1\text{-}T_2)$ is controlled to 20° C. or lower. As a more specific example, the control unit 5000 may control the time difference $(t_{Pmax}\text{-}t_s)$ so that the temperature difference $(T_1\text{-}T_2)$ is controlled to 10° C. or lower. As a more specific example, the control unit 5000 may control the time difference $(t_{Pmax}\text{-}t_s)$ so that the temperature difference $(T_1\text{-}T_2)$ is controlled to 5° C. or lower. As a more specific example, the control unit 5000 may control the time difference $(t_{Pmax}\text{-}t_s)$ so that the temperature difference $(T_1\text{-}T_2)$ is controlled to 3° C. or lower.

Also, referring to FIG. 12, in a case in which the target region TR is cooled using the cooling device 10000 according to an embodiment of the present application, although the pressure and temperature relate to the same target region TR, a time $(t_{Pmax}-t_s)$ required to reach the maximum pressure time point $t_{Pmax}$ from the time point $t_s$ at which the cryogen reaches the target region TR may be shorter than a time $(t_{Tmin}-t_s)$ required to reach the minimum temperature time point $t_{Tmin}$ from the time point $t_s$ at which the cryogen reaches the target region.

Here, the time point $t_s$ at which the cryogen reaches the target region TR may be a time point at which a pressure applied to the target region TR begins to increase. The time point $t_s$ at which the cryogen reaches the target region TR may be a time point at which a temperature of the target region TR begins to decrease.

1.2.2 Cooling Control Through State Regulation

The control unit 5000 of the cooling device 10000 according to an embodiment of the present application may control the temperature of the cryogen to be controlled. For example, the control unit 5000 may control the cryogen state regulation unit 3000 to control a spraying temperature of the cryogen.

As a specific example, the control unit 5000 of the cooling device 10000 according to an embodiment of the present application may apply an electrical signal to the spraying temperature controller 3100 to heat the cryogen passing through the spraying temperature controller 3100, thereby controlling the spraying temperature of the cryogen. As a specific example, the control unit 5000 of the cooling device 10000 according to an embodiment of the present application may apply an electrical signal to the spraying temperature controller 3100 to cool the cryogen passing through the spraying temperature controller 3100, thereby controlling the spraying temperature of the cryogen.

The cooling device 10000 disclosed in the present application may perform cooling of the target region TR according to the amount of cryogen sprayed and/or the temperature of the cryogen. The cooling device 10000 disclosed in the present application has an advantage in that cooling of the target region TR may be performed at a temperature more suitable for treatment by artificially heating or cooling the temperature of the cryogen.

Figure 13:
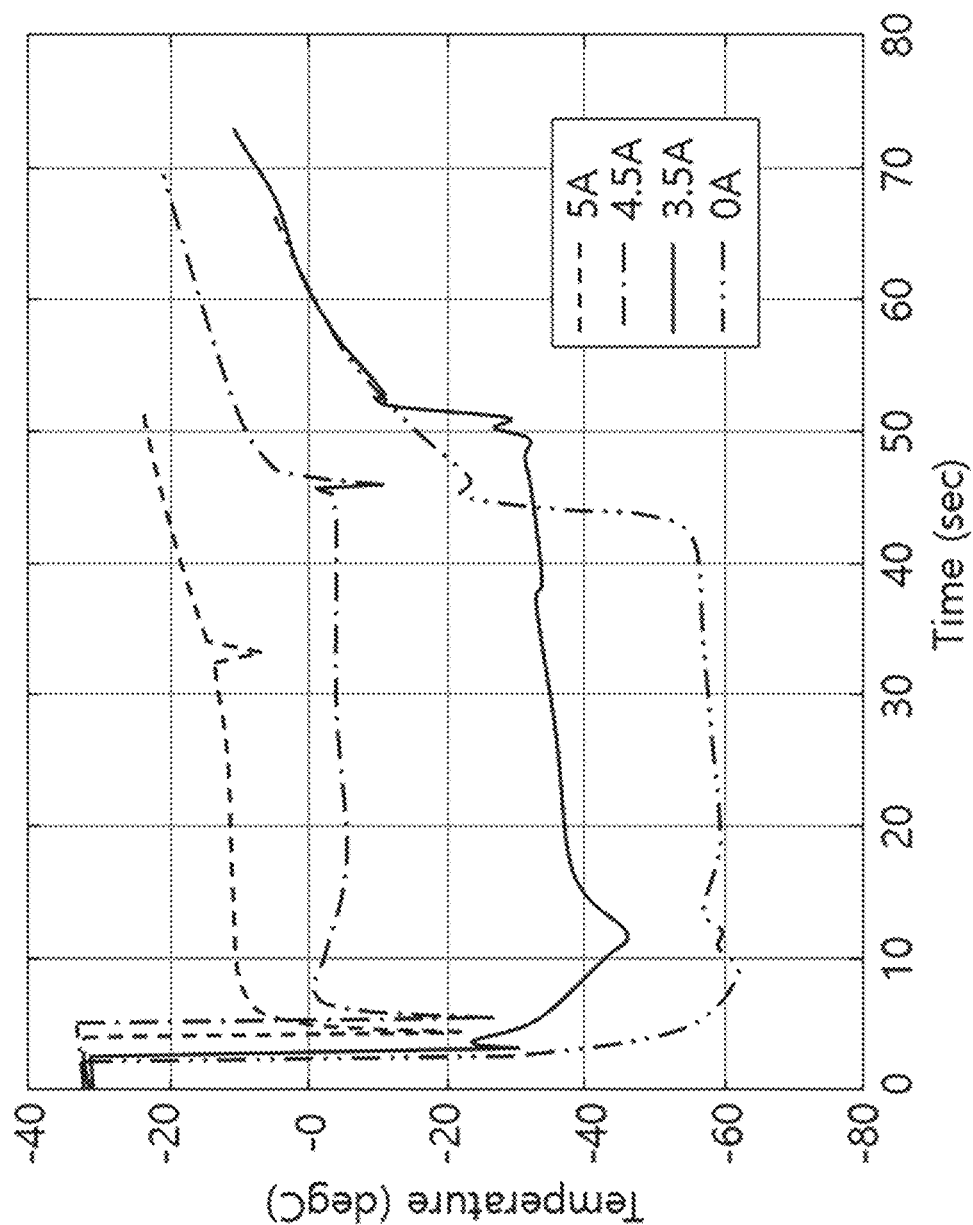
FIG. 13 is a graph showing temperatures of the target region TR in a case in which the cooling device heats and sprays a cryogen according to an embodiment of the present application.

FIG. 13 is a graph showing temperatures of the target region TR in a case in which the cooling device 10000 heats and sprays a cryogen according to an embodiment of the present application.

The cooling device 10000 may include the spraying temperature controller 3100 which includes a heating element, and the spraying temperature controller 3100 may perform a function of heating a cryogen to be discharged to the nozzle unit 4100. As a more specific example, the heating element may be a thermoelectric element.

According to an embodiment of the present application, a cooling temperature of the target region TR may be determined according to current applied to the spraying temperature controller 3100. According to an embodiment of the present application, the extent at which the cryogen to be discharged is heated may be controlled according to the current applied to the spraying temperature controller 3100, and, therefore, the cooling temperature of the target region TR where the heated cryogen reaches may be determined. The cooling device 10000 according to an embodiment of the present application may control a temperature of the target region TR according to the current applied to the spraying temperature controller 3100.

When a value of current applied to the heating element increases, the cooling device 10000 may control the temperature of the target region TR to a relatively higher temperature.

As a specific example, when a first current is applied to the spraying temperature controller 3100 of the cooling device 10000, a cryogen of a first flow-rate that has a first temperature may be discharged. When a second current is applied to the spraying temperature controller 3100 of the cooling device 10000, a cryogen of a second flow-rate that has a second temperature may be discharged. In a case in which the second current is higher than the first current, even when a difference between the first flow-rate and the second flow-rate is small, the second temperature may be higher than the first temperature.

The cooling device 10000 according to an embodiment of the present application may appropriately control the current applied to the spraying temperature controller 3100 and control the temperature of the target region TR within a range of at least an intrinsic temperature $T_0$ of the cryogen at normal pressure to 20° C. According to a specific embodiment, in a case in which $CO_2$ is used as a cryogen, the cooling device 10000 may control the temperature of the target region TR within a range of −78° C. to 20° C. According to a more specific embodiment, in a case in which $CO_2$ is used as a cryogen, the cooling device 10000 may control the temperature of the target region TR within a range of −70° C. to 20° C. According to a more specific embodiment, in a case in which $CO_2$ is used as a cryogen, the cooling device 1000 may control the temperature of the target region TR within a range of −60° C. to 20° C.

Therefore, the cooling device 10000 according to an embodiment of the present application may cool down the temperature of the target region TR to a temperature lower than a temperature at which cells die. For example, the cooling device 10000 according to the present application may perform cooling and cause cell death in cells whose death temperature is −40° C. Alternatively, the cooling device 10000 according to an embodiment of the present application may cool down the temperature of the target region TR to reach temperatures in a range of −40 to 10° C., which are temperatures at which apoptosis, inflammation relief, cryoanesthesia, or immune activation is possible.

The cooling device 10000 according to an embodiment of the present application may have a region in which a fluid may perform expansion and/or contraction, thereby performing cooling and/or heating of the cryogen. For example, the cooling device 10000 may include a first region in which the cryogen may rapidly expand, and the temperature may decrease due to the cryogen rapidly expanding in the first region. The cooling of the cryogen in the first region may be due to the Joule-Thomson effect.

The above-mentioned Joule-Thomson effect refers to a phenomenon in which a temperature decreases when a compressed gas expands. The Joule-Thomson effect refers to a phenomenon in which a temperature of a compressed and/or contracted gas changes in association with a thermodynamic phase consisting of pressure-temperature. The Joule-Thomson effect is a phenomenon applied when liquefying air or cooling through refrigerant.

2. Dynamic Cooling Control 2.1 Dynamic Cooling Control

Figure 14:
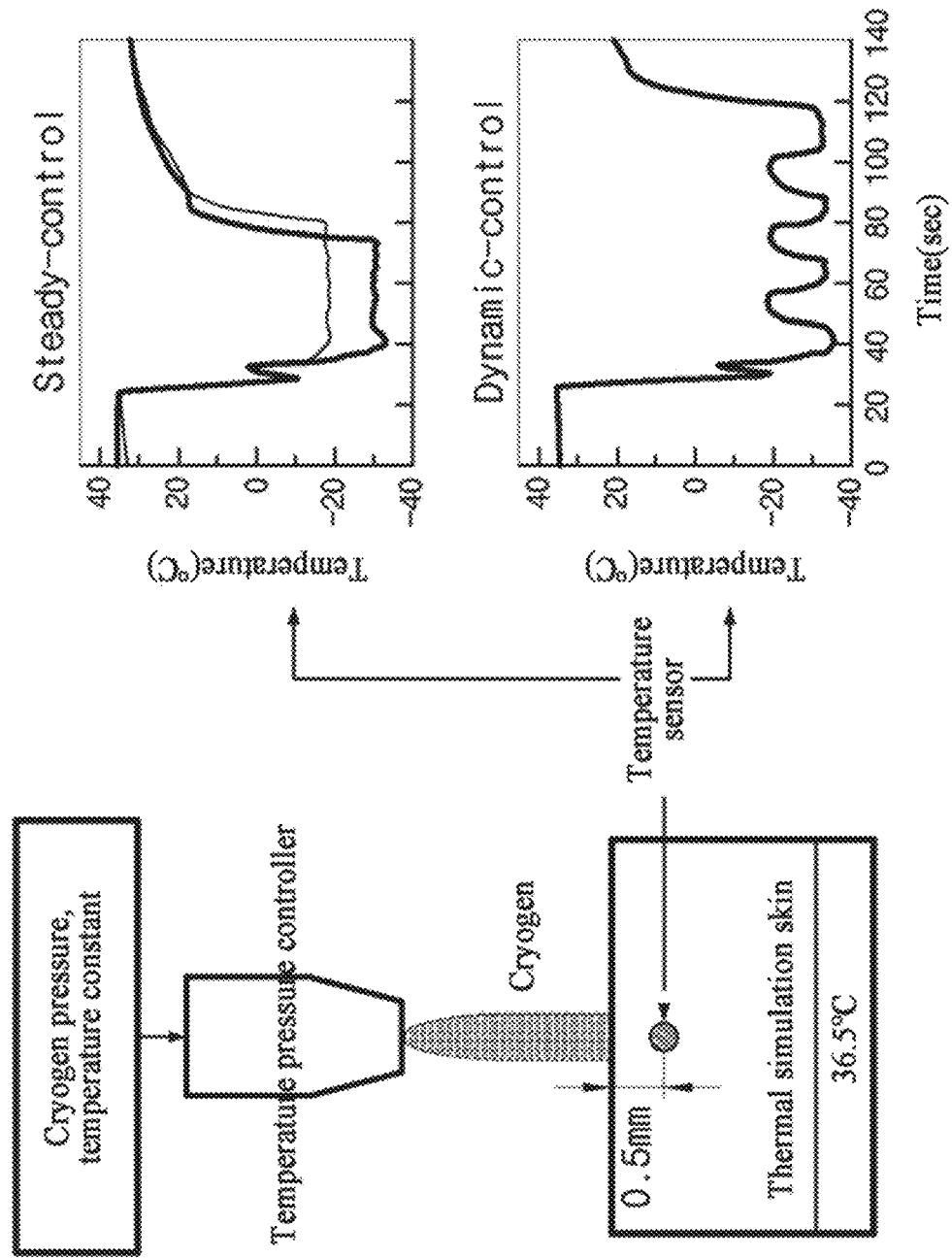
FIGS. 14 and 15 are views illustrating a temperature control method according to an embodiment of the present application.
Figure 15:
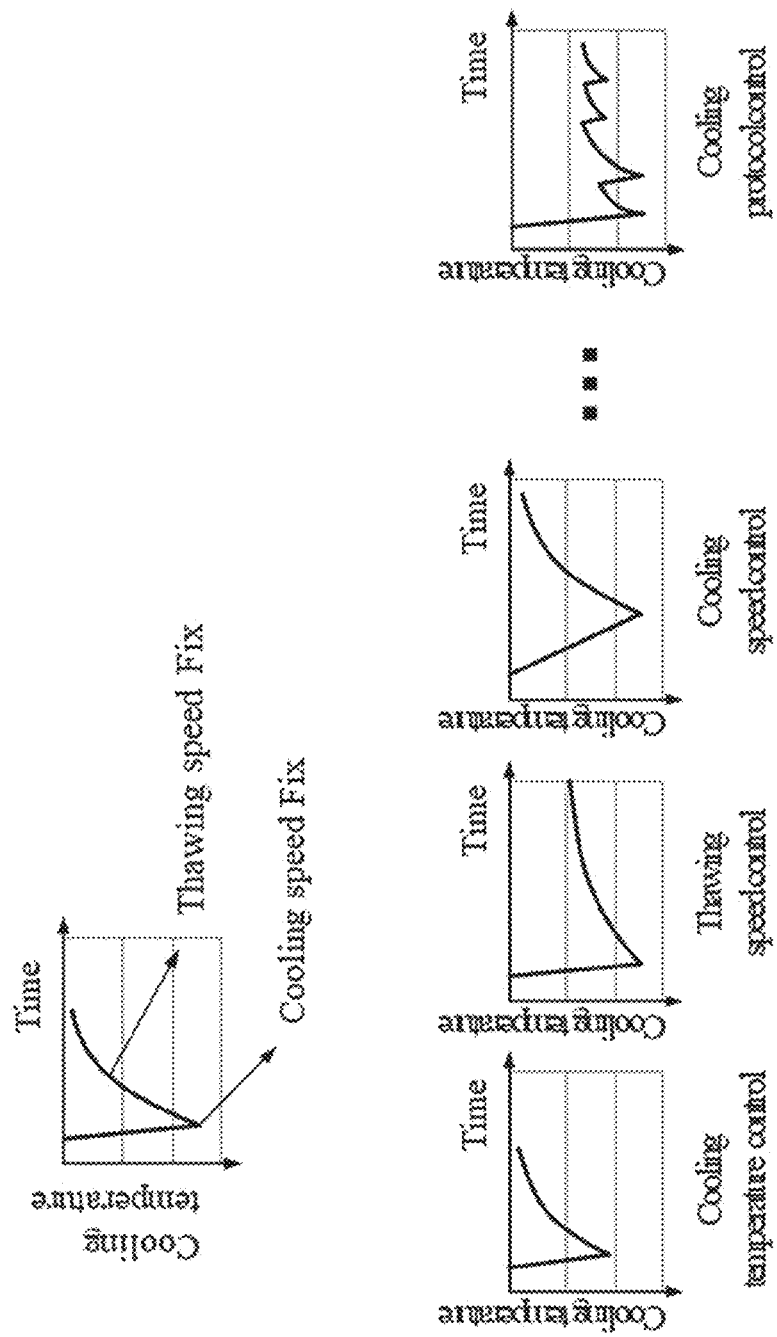

FIGS. 14 and 15 are views illustrating a temperature control method according to an embodiment of the present application.

The described technology may dynamically control a spraying temperature of a cryogen and may cool a target region TR while dynamically controlling a temperature of a cryogen according to protocols which are optimized according to treatment purposes and treatment regions having various depths at various sites according to the purpose of treatment or use.

Referring to FIG. 14, it can be seen that the temperature of the target region is dynamically controlled corresponding to the temperature control of the cryogen. According to an embodiment, the dynamic temperature control of the cooling device 10000 according to the described technology refers to controlling a temperature of a site subject to treatment to be kept within a corresponding temperature range, in which cells are not destructed, in order to prevent cells in the site subject to treatment from being destructed by cooling. Whether a cryogen is sprayed may be checked, a temperature of a site subject to treatment may be tracked, and, when the temperature cools down to a reference temperature or lower, cooling of the cryogen may be stopped or the cryogen may be heated in order to dynamically control the temperature of the site subject to treatment.

That is, through precise temperature control of the cryogen, the cryogen may be sprayed to the target region TR at a temperature different from the basic attribute temperature of the cryogen. The temperature control of the cryogen may include controlling at least one of a target cooling temperature, a cooling speed, a target thawing temperature, and a thawing speed.

In an embodiment of the described technology, a cooling parameter that may be used in calculating a quantity of heat Q (unit: W) applied from the control unit 5000 to the cryogen may be determined by thermal properties of a target treatment site and thermal properties of the cryogen. Here, a cooling amount by the cryogen may be determined by at least one of a cooling amount per unit mass C (unit: J/g-K), which includes at least one of latent heat or specific heat due to a phase change of the cryogen, a cryogen flow-rate V (unit: g/sec), and an intrinsic temperature $T_0$ (unit: K) of the cryogen at normal pressure. However, in a case in which a distance from the treatment site deviates from a predetermined distance, since it is self-evident that the quantity of heat Q is inversely proportional to the square of the distance, the quantity of heat Q will not be included in the parameter to be introduced below. For example Q necessary to reach the target cooling temperature is changed to $Q/x^2$ when a distance along which the cryogen is sprayed is increased x times the predetermined distance.

Also, the cooling parameter may be defined as follows. The quantity of heat Q applied to the cryogen may be expressed by two parameters $G_1$ and $G_2$ using a formula of heat that has a target cooling temperature $T_{c,1}$ (unit: K) on a surface, a cooling speed (unit: K/sec), a target thawing temperature $T_{c,2}$ (unit: K), and a thawing speed (unit: K/sec) as the range and has a depth d (unit: mm) from a surface of a cooling site, a cooling area A (unit: mm$^2$) on the surface, a density p (unit: g/mm$^3$) of a treatment site, an initial temperature ($T_{t0}$, unit: K) of the treatment site, specific heat Ct (unit: J/g) of the treatment site, a cooling amount of the cryogen, and the quantity of heat Q (unit: W) applied to the cryogen as the domain. The cooling parameter may determine the minimum Q required to implement the target cooling temperature and the target thawing temperature which are given in a range of the intrinsic temperature $T_0$ of the cryogen to 30° C. in an embodiment of the described technology. Meanwhile, the cooling parameter may determine the required Q so that the absolute values of the cooling speed and the thawing speed have a speed of 0.001 K/sec or more and may express Q associated with the target cooling temperature and the target thawing temperature and Q associated with the cooling speed and the thawing speed with ranges of the two parameters.

$$G_1 = \frac{VC(T_c - T_0) - Q}{C_t \rho A d (T_{t0} - T_c)} \quad \text{[Equation 1]}$$

Here, $T_c$ is a target temperature and may be represented as $T_{c,1}$ or $T_{c,2}$ according to a cooling process or a thawing process, respectively.

According to an embodiment, in order to implement temperatures in the range of, for example, $T_0$ to 30° C., the described technology may make the range of the parameter $G_1$ to satisfy the following conditions.

$$G_1 = \frac{VC(30 - T_0) - Q}{C_t \rho A d (T_{t0} - 30)} \geq 1 \quad \text{[Equation 2]}$$

Meanwhile, the cooling parameter $G_2$ relating to the cooling speed and the thawing speed is defined and limited as follows so that the absolute values of the cooling speed and the thawing speed have a speed of 0.001 K/sec or more.

$$G_2 = \frac{VC(T_c - T_0) - Q}{C_t \rho A d} \geq 0.001 \quad \text{[Equation 3]}$$

According to an embodiment of the described technology, a parameter $G_3$ which represents a response speed (K/sec) relating to the target cooling temperature or the target thawing temperature in association with the above variables may be defined. Specifically, the parameter $G_3$, in which a response speed of dynamic control corresponds to 1° C./sec or higher, is limited as follows.

$$G_2 = \frac{VC(T_c - T_0) - Q}{C_t \rho A d} \geq 1 \quad \text{[Equation 4]}$$

The target cooling temperature and the target thawing temperature, which are used in the three cooling parameters above, refer to temperatures measured within a depth of 1 mm from a surface of the target region TR according to an embodiment. The target cooling temperature of the cooling device 10000 according to the described technology may have a range of −200° C. to 0° C. when corresponding to a surface temperature of the treatment site, have a range of −70° C. to 0° C. when corresponding to an apoptosis temperature range, have a range of −40° C. to 10° C. when corresponding to a temperature range for immune-related treatment, have a range of −40° C. to 10° C. when corresponding to a temperature range for inflammation relief, have a range of −30° C. to 10° C. when corresponding to a temperature range for suppressing itching, have a range of −30° C. to 10° C. when corresponding to a temperature range for suppressing melanocytes, and have a range of −25° C. to 10° C. when corresponding to a temperature range for cryoanesthesia. The target thawing temperature may have a range of the target cooling temperature to 37° C.

Also, for multistage cooling control, the cooling device 10000 according to the described technology may have a multistage cooling protocol including a plurality of target cooling temperatures, a plurality of cooling speeds, a plurality of target thawing temperatures, and a plurality of thawing speeds.

Figure 16:
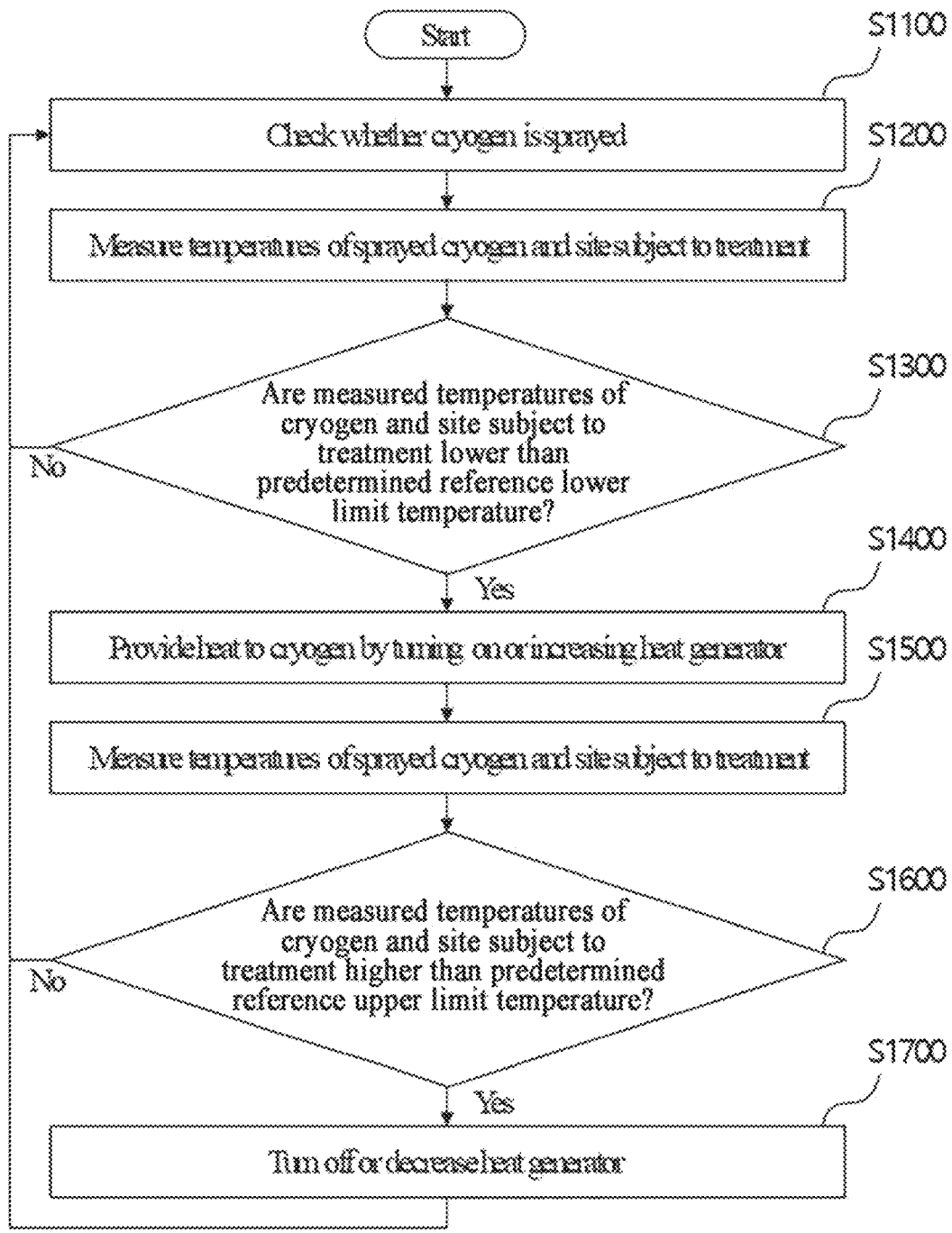
FIG. 16 is a flowchart illustrating an operation of a control unit of the cooling device according to an embodiment of the present application.

FIG. 16 is a flowchart illustrating an operation of the control unit 5000 of the cooling device according to an embodiment of the present application.

In order to dynamically control a temperature of a cryogen and a temperature of a target region corresponding thereto, the control unit 5000 of the cooling device according to the described technology may control each element of the cooling device independently or in association. Hereinafter, for convenience of description, in the sense that the control unit 5000 of the cooling device according to the described technology dynamically controls a temperature, the control unit 5000 may also be referred to as "dynamic temperature control unit."

The dynamic temperature control unit may control each element according to a predetermined cooling protocol. A cooling protocol control unit may perform dynamic cooling control based on a temperature of a cryogen and a temperature of a treatment site according to a non-contact type cooling protocol and, for precise temperature control, may operate control according to a protocol corresponding to a certain indication through control which takes into consideration a technology for measuring a temperature of a treatment site in real time, error correction control, and temperatures of the treatment site and cryogen and a time difference therebetween.

The control unit 5000 according to the described technology may control a spraying speed, a spraying temperature, a spraying pressure, and the like of the cryogen corresponding to a cooling distance. According to another embodiment, the control unit 5000 according to the described technology may optimize the cooling effect through control of a physical cooling distance keeper which is installed adjacent to the nozzle unit 4100, from which the cryogen is sprayed, and is configured to keep a separation distance between the nozzle unit 4100 and the target region TR.

For such control, the described technology may include a temperature sensor unit including at least one of a first temperature sensor unit for measuring a temperature of the nozzle unit 4100, a second temperature sensor unit for measuring a temperature of the target region TR, a third temperature sensor unit for measuring a temperature of the spraying temperature controller 3100, and a fourth temperature sensor unit for measuring a temperature of the cryogen.

Here, preferably, the second temperature sensor unit is formed of a non-contact temperature sensor, and the non-contact temperature sensor measures a temperature in the vicinity of the center of the target region TR as an angle of the non-contact temperature sensor is adjusted according to a given separation distance from the cooling distance keeper. For example, the cooling device 10000 according to the described technology may include the cooling distance keeper whose length is adjustable to a plurality of lengths (e.g., 1 cm, 2 cm, and 3 cm). Here, the cooling distance keeper may be mechanically interlocked with the non-contact temperature sensor and implemented so that an angle of installation of the non-contact temperature sensor, which investigates the central portion of the target region TR, is adjusted according to a set length of the cooling distance keeper.

For example, the control unit 5000 may be electrically connected to the valve 2100 and the heating element, control spraying of the cryogen from the nozzle unit 4100, and control driving of the heating element. The control unit 5000 may control the valve 2100 and/or a heat generating element to control the temperature of the cryogen and may control a temperature of a site subject to treatment to which the cryogen is sprayed. Here, the control unit 5000 controls the nozzle unit 4100 and the heating element on the basis of temperatures measured by the first temperature sensor unit and the second temperature sensor unit. The first temperature sensor unit is electrically connected to the control unit 5000, is disposed at a front end of the nozzle unit 4100, measures a temperature of a gas-phase cryogen sprayed from the nozzle unit 4100, and outputs the measured temperature to the control unit 5000.

Also, the second temperature sensor unit is electrically connected to the control unit 5000, is disposed at the front end of the nozzle unit 4100, measures the temperature of the site subject to treatment, and outputs the measured temperature to the control unit 5000. Here, preferably, the second temperature sensor unit is a non-contact type temperature sensor unit that measures the temperature of the site subject to treatment while being spaced apart therefrom.

The control unit 5000 may use at least one of a predetermined cooling condition or temperature information measured by the temperature sensor unit to control at least one of heat applied to the spraying temperature controller 3100 or a cryogen spraying time.

Also, according to a preferred embodiment of the described technology, the control unit 5000 includes a mode in which the control unit 5000 operates automatically according to a predetermined protocol and a mode in which the control unit 5000 operates according to a command input by a user according to a user operation mode. In the case of a user mode, temperature data measured by the temperature sensor unit may be stored, and the stored data may be analyzed and utilized in various fields in the future.

The control unit 5000 according to the described technology may be configured so that efficient control and power supply are performed by optimizing transmission of electrical signals and power supply between each element and the control unit 5000. Here, the control unit 5000 may include all kinds of devices capable of processing data, such as a processor. Here, for example, "processor" may refer to a data processing device embedded in hardware that has a physically structured circuit to perform a function expressed by a code or a command included in a program. Examples of the data processing device embedded in hardware include processing devices such as a microprocessor, a CPU, a processor core, a multiprocessor, an application-specific integrated circuit (ASIC), and a field programmable gate array (FPGA), but the scope of the described technology is not limited thereto.

Also, the control unit 5000 may control a cooling element or a heating element so that the cryogen is kept at a predetermined temperature. As another embodiment, the control unit 5000 may control a cooling element or a heating element so that at least one or more temperature values are set in advance and, during a time in which cooling is performed, the cryogen has each temperature value sequentially or periodically.

According to the described technology, through high-power and high-precision cooling temperature control, the control unit 5000 may set optimized protocols for different diseases including skin cancer, benign tumor, inflammatory disease, immunodeficiency disease, or other diseases and control the cooling device 10000 according to the protocols. Also, through precise cooling control, the control unit 5000 may prevent death of normal cells surrounding the cells in lesions and perform accurate and safe customized cooling treatment for different diseases including skin cancer, benign tumor, inflammatory disease, immunodeficiency disease, or other diseases. It is also possible to extend to skin regions and other treatment regions through technical or clinical differentiation, and a diagnostic and therapeutic fusion cooling device may be implemented using the present cooling device. Also, the cooling device 10000 may constitute a fusion therapeutic device by being combined with laser, radiofrequency ablation, plasma, or microwave ablation element.

The control unit 5000 according to the described technology may induce treatment to be performed at a predetermined separation distance from the target region TR corresponding to the protocol, and, in a case in which a distance to a treatment site that is measured by a distance sensor deviates from a static cooling distance, e.g., in a case in which the nozzle unit 4100 approaches the target region TR within a proper distance or is spaced apart from the target region TR by a predetermined distance or more, the control unit 5000 according to the described technology may limit the operation of the cooling device 100000 or control the cooling device 10000 to generate an alarm so that the user recognizes the alarm. That is, the control unit 5000 according to the described technology includes the control unit 5000 for controlling a cooling distance for keeping the separation distance between the nozzle unit 4100 and the target region TR. The control unit 5000 may receive temperature information from a temperature sensor unit and control the cooling device 10000 using the temperature information. The temperature sensor unit may include at least one of a first temperature sensor unit for measuring a temperature of the nozzle unit 4100, a second temperature sensor unit for measuring a temperature of the target region TR, a third temperature sensor unit for measuring a temperature of the spraying temperature controller 3100, and a fourth temperature sensor unit for measuring a temperature of the cryogen.

Here, a non-contact temperature sensor is configured to measure a temperature in the vicinity of the center of the target region TR as an angle of the non-contact temperature sensor is adjusted according to a given separation distance from the cooling distance keeper, and the control unit 5000 may use at least one of a predetermined cooling condition or temperature information measured by the temperature sensor unit to control at least one of heat applied to the spraying temperature controller 3100 or a cryogen spraying time.

The control unit 5000 includes a mode in which the control unit 5000 operates automatically according to a predetermined protocol and a mode in which the control unit 5000 operates according to a command input by a user according to a user operation mode. In the case of a user mode, temperature data measured by the temperature sensor unit may be stored, and the stored data may be utilized. Also, in the case of a mode that requires attention such as when cooling at a predetermined temperature or lower, operation of the control unit 5000 may be limited such that the control unit 5000 operates only when a plurality of user inputs are received through a button. In this way, it is possible to prevent malfunctioning due to a user's operation mistake.

2.2 Examples of Dynamic Cooling Control

The cooling device 10000 according to an embodiment of the present application may perform cooling on the basis of a measured temperature measured by at least one of the first to fourth temperature sensor units. As a specific example, the cooling device 10000 may compare a measured temperature, which is measured by at least one of the first to fourth temperature sensor units, with a predetermined numerical value and control a temperature of a cryogen sprayed from the nozzle unit 4100. As a more specific example, the cooling device 10000 may compare a measured temperature, which is measured by at least one of the first to fourth temperature sensor units, with a reference lower limit temperature and, in a case in which the measured temperature is lower than the reference lower limit temperature, increase a temperature of a cryogen sprayed from the nozzle unit 4100 or stop spraying of the cryogen. As a more specific example, the cooling device 10000 may compare a measured temperature, which is measured by at least one of the first to fourth temperature sensor units, with a reference upper limit temperature and, in a case in which the measured temperature is higher than the reference upper limit temperature, decrease a temperature of a cryogen sprayed from the nozzle unit 4100 or increase the amount of cryogen sprayed.

Hereinafter, referring to FIG. 16, each step of a method of controlling a temperature of a site subject to treatment by the cooling device 10000 according to an embodiment of the described technology will be described.

Each step of a method of controlling a temperature of a site subject to treatment by a local cooling device according to an embodiment of the described technology will be described below.

First, in a case in which heat is provided to a cryogen in order to keep a temperature of a site subject to treatment within a corresponding temperature range, as Step S1100, the cooling device 10000 may check whether the cryogen is sprayed. According to an embodiment of the present application, the spraying of the cryogen is performed as a user operates a button exposed to the outside from the housing. When the user operates the button, this is detected by the control unit 5000. When the control unit 5000 controls the solenoid valve 2100 according to a detected signal of the button and opens a flow path, a cryogen which was kept at a corresponding high pressure through the cryogen cooling unit 3200 may flow into the spraying temperature controller 3100, and the cryogen may be sprayed through the nozzle unit 4100.

Here, the control unit 5000 may check whether the cryogen is sprayed and, when the cryogen is not sprayed, perform an operation corresponding thereto or end the operation of the cooling device 10000.

Next, as Step S1200, the cooling device 10000 may measure temperatures of the cryogen sprayed and the site subject to treatment.

According to an embodiment of the present application, the temperatures of the cryogen sprayed and the site subject to treatment may be measured through the first temperature sensor and the second temperature sensor. When it is checked in Step S1100 that the cryogen is sprayed, the first temperature sensor may measure the temperature of the sprayed cryogen in real time and apply the measured value to the control unit 500, and the second temperature sensor may measure the temperature of the site subject to treatment in real time and apply the measured value to the control unit 5000.

Next, as Step S1300, the cooling device 10000 may determine whether the measured temperatures of the cryogen and the site subject to treatment are temperatures lower than a predetermined reference lower limit temperature.

According to an embodiment of the present application, the reference lower limit temperature is a reference lower limit of a temperature range which prevents destruction of cells of the site subject to treatment, and may be set differently according to a treatment site and/or a treatment purpose. Preferably, the reference lower limit temperature is preset in the control unit 5000. However, the user may operate a button provided for temperature control and arbitrarily change the reference lower limit temperature as necessary.

According to an embodiment of the present application, when, in Step S1200, the first temperature sensor and the second temperature sensor measure the temperatures of the sprayed cryogen and the site subject to treatment and apply the measured values to the control unit 5000, the control unit 5000 may compare the temperatures of the cryogen and the site subject to treatment, which are measured in real time through the first temperature sensor and the second temperature sensor, with a predetermined reference lower limit temperature and detect a measured temperature which is lower than the predetermined reference lower limit temperature.

Next, as Step S1400, the cooling device 10000 may, when the measured temperature is lower than the reference lower limit temperature, cause the heating element to provide heat to the cryogen and control the temperature of the site subject to treatment to which the cryogen is sprayed.

According to an embodiment of the present application, when, in Step S1300, the measured temperature of the site subject to treatment is detected as a temperature lower than the reference lower limit temperature by the control unit 5000, power may be supplied to the heating element included in the spraying temperature controller 3100, causing the heating element to be turned on and generate heat. As the heating element generates heat, heat may be provided to the cryogen flowing along a nozzle hole and cause the temperature of the cryogen to increase. In Step S1400, a cryogen at a higher temperature as compared with time points before Step S1300 may be sprayed to the site subject to treatment, and thus the temperature of the site subject to treatment may be controlled. For example, the power applied to the spraying temperature controller 3100 may be controlled using the proportional-integral-derivative (PID) technique.

According to another embodiment of the present application, when, in Step S1300, the measured temperature of the site subject to treatment is detected as a temperature lower than the reference lower limit temperature by the control unit 5000, driving of the heating element included in the spraying temperature controller 3100 may be increased. In other words, when, in Step S1300, the measured temperature of the site subject to treatment is detected as a temperature lower than the reference lower limit temperature by the control unit 5000, the control unit 5000 may control a driving amount of the heating element in Step S1400 to be increased as compared with a driving amount of the heating element in Step S1100, causing the driving of the heating element to be increased. For example, when the driving of the heating element is increased, the amount of current flowing in the heating element in Step S1400 may be increased as compared with the amount of current flowing in the heating element in Step S1100. For example, when the driving of the heating element is increased, the temperature of the heating element in Step S1100 may be lower than the temperature of the heating element in Step S1400.

Next, as Step S1500, the cooling device 10000 may re-measure the temperatures of the cryogen sprayed and the site subject to treatment.

According to an embodiment of the present application, when, in Step S1400, the heating element is driven and the cryogen is sprayed, the temperatures of the cryogen sprayed and the site subject to treatment are re-measured in Step S1500. Even in this case, the temperatures are measured through the first temperature sensor and the second temperature sensor, the first temperature sensor may measure the temperature of the sprayed cryogen in real time and apply the measured value to the control unit 5000, and the second temperature sensor may measure the temperature of the site subject to treatment in real time and apply the measured value to the control unit 5000.

Next, as Step S1600, the cooling device 10000 may determine whether the measured temperatures of the cryogen and the site subject to treatment are temperatures higher than a predetermined reference upper limit temperature.

According to an embodiment of the present application, the reference upper limit temperature is a reference upper limit temperature corresponding to a time point at which the heating element which provides heat to the cryogen is turned off or the power applied to the heating element is reduced. Preferably, the reference upper limit temperature is preset in the control unit 5000. However, the user may operate a button provided for temperature control and arbitrarily change the reference upper limit temperature as necessary. For example, the power applied to the spraying temperature controller 3100 may be controlled by the PID technique.

According to an embodiment of the present application, when, in Step S1500, the first temperature sensor and the second temperature sensor measure the temperatures of the sprayed cryogen and the site subject to treatment and apply the measured values to the control unit 5000, in Step S1600, the control unit 5000 may compare the temperatures of the cryogen and the site subject to treatment, which are measured in real time through the first temperature sensor or the second temperature sensor, with a predetermined reference upper limit temperature and detect a measured temperature which is higher than the predetermined reference upper limit temperature.

Next, as Step S1700, the cooling device 10000 may, when the measured temperature is higher than the reference upper limit temperature, turn off the heating element or reduce the power applied to the heating element to control the temperature of the site subject to treatment.

According to an embodiment of the present application, when, in Step S1600, the measured temperature of the site subject to treatment is detected as a temperature higher than the reference upper limit temperature by the control unit, in Step S1700, the supply of power to the heating element included in the spraying temperature controller 3100 may be terminated such that the heating element is turned off or the power applied to the heating element is reduced. Thus, in Step S1700, a cryogen at a lower temperature as compared with that at time points before Step S1600 may be sprayed to the site subject to treatment, and the temperature of the site subject to treatment may be controlled. For example, the power applied to the spraying temperature controller 3100 may be controlled using the PID technique.

According to another embodiment of the present application, when, in Step S1600, the measured temperature of the site subject to treatment is detected as a temperature higher than the reference upper limit temperature by the control unit, driving of the heating element included in the spraying temperature controller 3100 may be decreased. In other words, when, in Step S1600, the measured temperature of the site subject to treatment is detected as a temperature higher than the reference upper limit temperature by the control unit 5000, the control unit 5000 may control a driving amount of the heating element in Step S1700 to be decreased as compared with a driving amount of the heating element in Step S1400, causing the driving of the heating element to be decreased. For example, when the driving of the heating element is decreased, the amount of current flowing in the heating element in Step S1700 may be decreased as compared with the amount of current flowing in the heating element in Step S1400. For example, when the driving of the heating element is decreased, the temperature of the heating element in Step S1400 may be higher than the temperature of the heating element in Step S1700.

Figure 17:
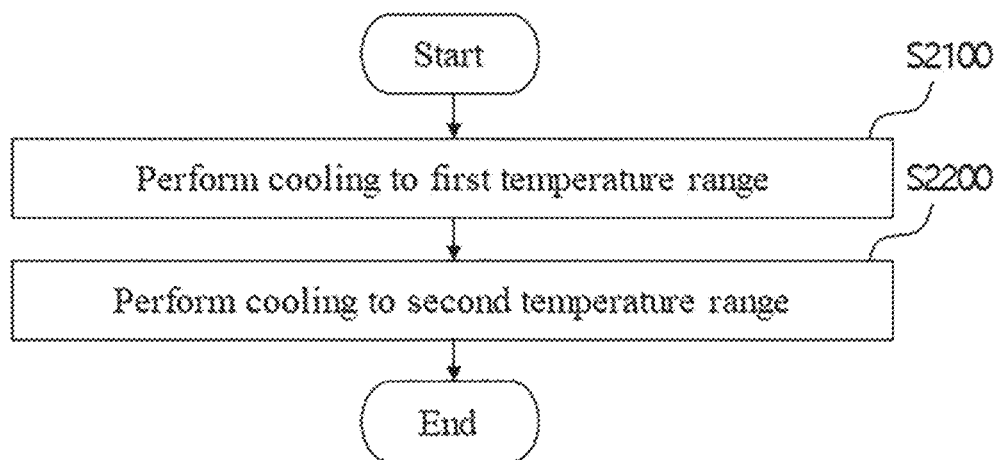
FIGS. 17 and 18 are views for describing operations related to multi-step temperature control using the cooling device according to an embodiment of the present application.
Figure 18:
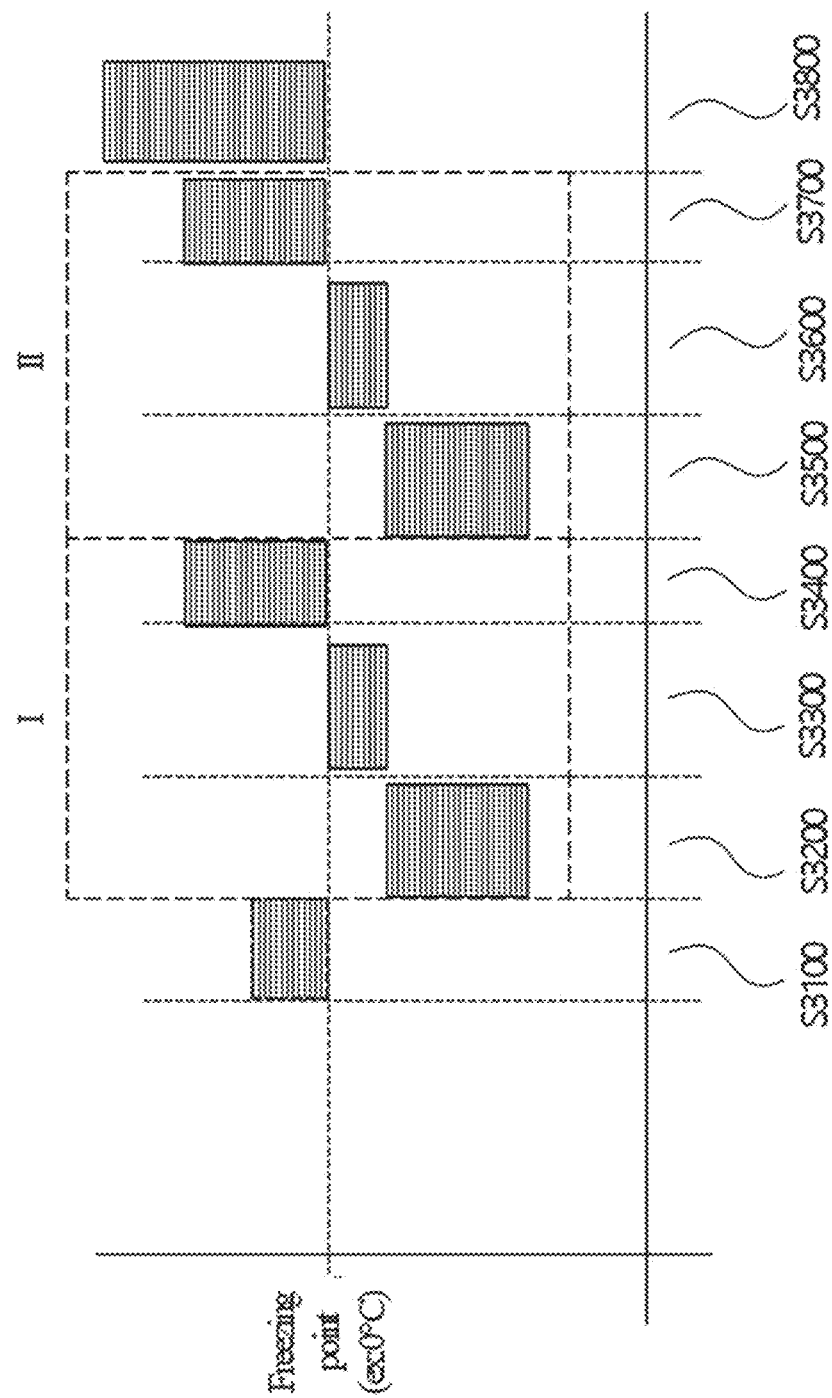

FIGS. 17 and 18 are views for describing operations related to multi-step temperature control using the cooling device 10000 according to an embodiment of the present application.

More specifically. FIG. 17 is a flowchart illustrating sequential steps of a method of cooling the target region TR by the cooling device 10000 according to an embodiment of the present application, and FIG. 18 is a conceptual diagram for describing another embodiment in which the cooling device 10000 according to an embodiment of the described technology cools the target region TR.

Referring to FIG. 17, the cooling device 10000 according to an embodiment of the present application may be used in anesthetizing the target region TR by cooling the target region TR to a precise temperature. Here, the cooling device 10000 may perform cooling so that a temperature range of the target region TR is −25° C. to 10° C. The cooling device 10000 according to an embodiment of the present application may be used in inducing effects other than anesthetizing the target region TR, such as disinfection, vasoconstriction, and hemostasis, by cooling the target region TR to a precise temperature. Here, the cooling device 10000 may perform cooling so that a temperature range of the target region TR is −25° C. to 10° C.

The cooling method by the cooling device according to an embodiment of the present application may control the temperature and/or spraying speed (that is, amount sprayed) of the cryogen sprayed using the nozzle unit 3100 and control the temperature of the target region TR by multiple steps.

The cooling device 10000 according to an embodiment of the present application may perform cooling of the target region TR to a first temperature range (S2100). The control unit 5000 may cool the target region TR to the first temperature range on the basis of pre-stored information. The control unit 5000 may be set to cool the target region TR to the first temperature range.

According to an embodiment of the present application, the cooling in Step S2100 may be a procedure for performing disinfection. For example, Step S2100 may be a procedure for, when disinfecting the target region TR using a disinfecting agent, providing the disinfecting agent in an environment whose temperature is higher than a freezing point of the disinfecting agent. As another example, Step S2100 may be a procedure for inducing a disinfecting effect through cooling of the target region TR.

As a more specific example, in a case in which Step S2100 is performed to induce the disinfecting effect through the cooling of the target region TR, the first temperature range may be a temperature range in which bacteria that may exist on the skin surface of the target region TR, i.e., the treatment site, may be killed or the activity of the bacteria may be decreased.

For example, the temperature range in which bacteria that may exist on the skin surface may be killed or the activity of the bacteria may be decreased may be temperatures lower than or equal to −2° C. As another example, the temperature range in which bacteria that may exist on the skin surface may be killed or the activity of the bacteria may be decreased may be −90° C. to −2° C.

The cooling device 10000 according to an embodiment of the present application may perform cooling of the target region TR to a second temperature range (S2200). The control unit 5000 may cool the target region TR to the second temperature range on the basis of pre-stored information. The control unit 5000 may be set to cool the target region TR to the second temperature range.

According to an embodiment of the present application, the cooling in Step S2200 may be a procedure for performing anesthesia. For example, Step S2200 may be a procedure for, when anesthetizing the target region TR using an anesthetic agent, providing the anesthetic agent in an environment whose temperature is higher than a freezing point of the anesthetic agent. As another example, Step S2200 may be a procedure for inducing an anesthetic effect through cooling of the target region TR.

As a more specific example, in a case in which Step S2200 is performed to induce the anesthetic effect through the cooling of the target region TR, Step S2200 may be performed at a temperature higher than a cooling temperature for inducing the disinfecting effect through the cooling of the target region TR.

For example, the temperature at which the anesthetic effect is induced through the cooling may be in a range of −25° C. to 10° C. As another example, the temperature at which the anesthetic effect is induced through the cooling may be in a range of −2° C. to 10° C.

The cooling device 10000 according to an embodiment of the present application may perform cooling to the first temperature range (S2100) and perform cooling to the second temperature range (S2200). Here, the first temperature range may be a temperature for performing anesthesia. The second temperature range may be a temperature range for injecting a medicinal fluid. For example, Step S2200 may be a procedure for, when injecting a medicinal fluid into the target region TR, providing the medicinal fluid in an environment whose temperature is higher than a freezing point of the medicinal fluid.

As a more specific example, in a case in which Step S2200 is performed to form an environment for providing the medicinal fluid to the target region TR, Step S2200 may be performed at a temperature higher than the cooling temperature for inducing the disinfecting effect through the cooling of the target region TR.

For example, the temperature for providing temperature control at a temperature lower than or equal to the freezing point of the medicinal fluid through the cooling may be in a range of 0° C. to 37° C.

The cooling device 10000 according to an embodiment of the present application may perform cooling to the first temperature range (S2100) and perform cooling to the second temperature range (S2200). Here, the first temperature range may be a temperature for cooling the target region TR. The second temperature range may be a temperature for separating the guide unit 4210 in contact with the vicinity of the target region TR during the cooling of the target region TR. In other words, in a case in which the guide unit 4210 is used in providing the cryogen to the target region TR, the guide unit 4210 comes into contact with the target region TR, and a phenomenon in which, when separating the guide unit 4210 from the target region TR after the cooling is completed, the guide unit 4210 sticks to a surface of the target region TR may occur. To prevent damage thereby, the cooling device 10000 according to an embodiment of the present application may perform cooling to the second temperature range (S2200) before separating the guide unit

4210 from the target region TR. For example, the second temperature range may be −2° C. to 37° C.

However, the above temperature ranges are merely specific embodiments, and specific temperature ranges may be determined by selecting temperature ranges in which treatment is possible according to characteristics of a target region TR on which treatment is to be performed, a method of cooling the target region TR, and the like. Therefore, temperature ranges for treatment should not be limited by the above temperature ranges.

Also, the example in which the cooling device 10000 according to an embodiment of the present application performs multi-step temperature control according to the two temperature ranges in providing cooling energy to the target region TR has been disclosed in detail above. However, the above-described specific embodiment may be easily modified, and multi-step temperature control according to three or more temperature ranges is also possible. The omission of redundant description does not mean that the cooling device 10000 according to the present application is not able to perform the multi-step temperature control according to three or more temperature ranges.

Through the above-described process, the cooling device 10000 according to an embodiment of the present application may perform one anesthesia and/or one medicinal fluid injection on the target region TR. Also, the cooling device 10000 according to an embodiment of the present application may perform anesthesia multiple times and/or medicinal fluid injection multiple times on the target region TR.

FIG. 18 is a view for describing in detail an operation in which the cooling device 10000 according to an embodiment of the present application performs anesthesia and/or medicinal fluid injection multiple times.

The cooling device 10000 according to an embodiment of the present application may include a first injection step of injecting a first medicinal fluid (II) and a second injection step of injecting a second medicinal fluid (I). The cooling device 10000 may store the first medicinal fluid and the second medicinal fluid therein and sequentially transfer the first medicinal fluid and the second medicinal fluid to the target region TR. As a specific example, the first medicinal fluid may be a therapeutic agent, and the second medicinal fluid may be a disinfecting agent.

The cooling device 10000 according to an embodiment of the present application may perform the second injection step (I) for disinfecting the target region using the disinfecting agent prior to starting the first injection step of injecting the first medicinal fluid (II).

In the second injection step of injecting the second medicinal fluid (I), the operation according to multi-step temperature control may be performed. In the second injection step of injecting the second medicinal fluid (I), the cooling device 10000 may perform cooling to a first temperature range (S3200), perform cooling to a second temperature range (S3300), and perform cooling to a third temperature range (S3400). Here, the first temperature range may be a temperature for disinfection, the second temperature range may be a temperature for anesthesia, and the third temperature range may be a temperature range for injection.

In FIG. 18, steps performed by the cooling device 10000 are classified on the basis of freezing points. While the second medicinal fluid, which is a disinfecting agent, is injected, the freezing point may be a freezing point of the second medicinal fluid. In other words, while the second medicinal fluid, which is a disinfecting agent, is injected, the cooling device 10000 may form an environment in which the second medicinal fluid is injected to be at a temperature higher than the freezing point, thereby preventing freezing of the second medicinal fluid when the second medicinal fluid is transferred to the target region.

The cooling device 10000 according to an embodiment of the present application may further perform a pre-cooling operation (S3100). In a case in which a cryogen having a temperature lower than or equal to a freezing point is immediately applied to the target region TR, the pre-cooling operation may be used to eliminate the possibility of an occurrence of damage due to a temperature difference between the target region TR and the cryogen or to stably implement a target cooling temperature and a cooling speed regardless of a temperature of the target region. Here, a pre-cooling temperature may have a temperature range of 0° C. to 10° C. In still another embodiment, the cooling device 10000 may perform the pre-cooling step (S3100) by applying a temperature equal to or higher than a predetermined temperature before the second injection step of injecting the second medicinal fluid (I). Here, a pre-cooling temperature may have a temperature range of 0° C. to 10° C.

Referring back to FIG. 18, after the second injection step (I), the first injection step (II) of injecting the first medicinal fluid, which is a therapeutic agent, to the target region TR may be performed. Like the second injection step (I), a disinfection step (S3500), an anesthesia step (S3600), and an injection step (S3700) may be performed through multi-step temperature control.

In the drawing, steps performed by the cooling device 1000 are classified on the basis of freezing points. While the second medicinal fluid, which is a disinfecting agent, is injected, the freezing point may be a freezing point of the first medicinal fluid. In other words, while the first medicinal fluid, which is a disinfecting agent, is injected, the cooling device 10000 may form an environment in which the first medicinal fluid is injected to be at a temperature higher than the freezing point, thereby preventing freezing of the first medicinal fluid when the first medicinal fluid is transferred to the target region. Although the freezing point of the first medicinal fluid and the freezing point of the second medicinal fluid are illustrated in the drawing as being the same, this is merely more convenience of description, and the freezing point of the first medicinal fluid may also be different from the freezing point of the second medicinal fluid.

The cooling device 10000 according to an embodiment of the present application may, after the first injection step (II), cool the target region TR to a temperature higher than a disinfection temperature, an anesthesia temperature, and/or an injection temperature and separate the guide unit 4210 of the cooling device from the target region TR.

3. Provision of Vibration

The cooling device 10000 according to an embodiment of the present application may perform a function of providing vibration to the target region TR.

The control unit 5000 of the cooling device 10000 may perform a function of providing vibration to the target region TR.

As a specific example, the control unit 5000 may provide vibration to the target region TR by controlling a cryogen discharge cycle. The control unit 5000 may repeatedly perform an operation of discharging a cryogen at a pressure of at least a first strength and discharging the cryogen at a pressure of a second strength different from the first strength. The vibration may be generated by a pressure applied to the target region TR by the cryogen discharged from the cooling device 10000.

As another specific example, the control unit 5000 may provide vibration to the target region TR by controlling an operation of the valve 2100. Here, the vibration of the target region TR may be generated due to transmission of vibration of the valve 2100.

As still another specific example, the control unit 5000 may provide vibration to the target region TR by controlling an operation of a vibration generating device. Here, the vibration generating device may be mounted on one region of the cooling device 10000 that comes into contact with the target region TR.

According to an embodiment of the present application, the cooling device 10000 may be used to provide cooling on a tissue. As a more specific example, the cooling device 10000 may be used to provide cooling on a tissue to anesthetize one region of the tissue.

In a case in which the cooling device 10000 is used for anesthetizing the target region TR, the cooling device 10000 may be used to make the anesthetic effect due to providing cooling and the anesthetic effect due to providing vibration cause synergy.

As a more specific embodiment, the cooling device 10000 according to an embodiment of the present application may control the valve 2100 so that, while the cryogen is sprayed to the target region TR, a pressure applied to the target region TR changes between at least a first pressure and a second pressure. In this way, an anesthetic effect due to a temperature drop and an anesthetic effect due to vibration may occur in the target region TR.

The first pressure may be a value higher than the second pressure. The first pressure may be a value having a relatively higher pressure than the atmospheric pressure. The second pressure may be a value similar to the atmospheric pressure.

4. Cryogen Spraying Uniformity Control

The cooling device 10000 according to an embodiment of the present application may perform a function of improving uniformity of the amount of cryogen sprayed to the target region TR. The control unit 5000 of the cooling device 10000 according to an embodiment of the present application may perform a function of improving uniformity of the amount of cryogen sprayed to the target region TR According to an embodiment of the present application, the control unit 5000 of the cooling device 10000 may improve uniformity of the amount of cryogen sprayed to the target region TR by controlling the valve 2100.

As a more specific example, the control unit 5000 may control an opening time of the valve 2100 on the basis of a pressure of a cryogen stored in the reservoir 1100. The control unit 5000 may, when the pressure of the cryogen stored in the reservoir 1100 decreases, extend the opening time of the valve 210 to a predetermined time or more so that a substantially constant amount of cryogen is sprayed through the nozzle unit 4100.

As another specific example, the control unit 5000 may control the degree of opening of the valve 2100 on the basis of the pressure of the cryogen stored in the reservoir 1100.

When the pressure of the cryogen stored in the reservoir 1100 decreases, the control unit 5000 may increase the degree of opening of the valve 2100 (that is, increase the amount of fluid passing through the valve 2100 per unit time) so that a substantially constant amount of cryogen is sprayed through the nozzle unit 4100.

Alternatively, the control unit 5000 may control a repetitive cycle of opening and closing of the valve 2100 on the basis of the pressure of the cryogen stored in the reservoir 1100. In a specific embodiment, when the pressure of the cryogen stored in the reservoir 1100 has a predetermined numerical value or higher, the control unit 5000 may control the valve 2100 to be opened three times or less and closed three times or less per second. When a duration of the operation in which the valve 2100 is controlled to be opened three times or less and closed three times or less per second is at least one second or more, the control unit 5000 may control the valve 2100 to be opened four times or more and closed four times or more per second when the pressure of the cryogen stored in the reservoir 1100 is decreased to a predetermined numerical value or lower.

According to an embodiment of the present application, the cooling device 10000 may include a configuration for pressure maintenance, thereby improving uniformity of the amount of cryogen sprayed to the target region TR. As a more specific example, the cooling device 10000 may further include the cryogen cooling unit 3200 disposed between the reservoir 1100 and the nozzle unit 4100 and capable of keeping a cryogen, whose temperature is changed due to a surrounding temperature, at a predetermined temperature. The cryogen cooling unit 3200 may control a temperature of a cryogen accommodated within a predetermined volume, thereby reducing fluctuations in the pressure of the cryogen and inducing the cryogen sprayed through the nozzle unit 4100 to be sprayed by a substantially constant amount.

According to an embodiment of the present application, the cooling device 10000 may include a configuration for speed maintenance, thereby improving uniformity of the amount of cryogen sprayed to the target region TR. As a more specific example, the cooling device 10000 may further include the limited-capacity cryogen reservoir 3410 disposed between the reservoir 1100 and the nozzle unit 4100 and capable of accommodating the cryogen by a constant volume. The limited-capacity cryogen reservoir 3410 may keep the speed of the cryogen discharged by the spraying unit 4000 within a predetermined range, thereby reducing fluctuations in the pressure of the cryogen during a limited time and inducing the cryogen sprayed through the nozzle unit 4100 to be sprayed by a substantially constant amount.

5. Driving Control of Cooling Device 10000

The cooling device 10000 according to an embodiment of the present application may perform an operation in which convenience of a user using the cooling device 10000 is improved.

Figure 19:
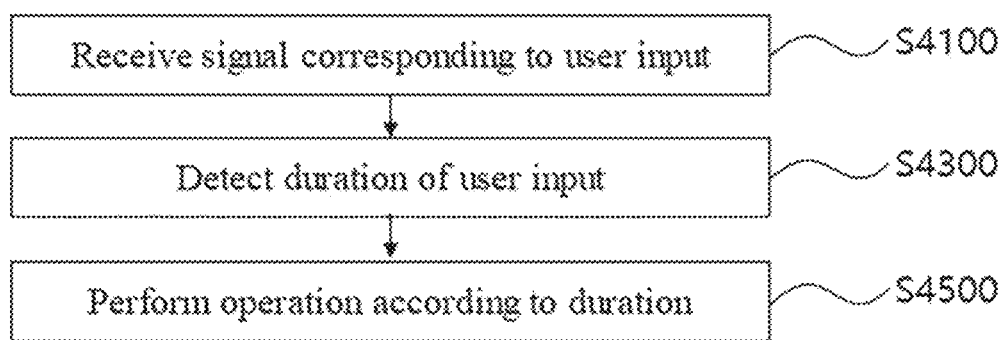
FIG. 19 is a flowchart for describing an operation of controlling driving of the cooling device according to an embodiment of the present application.

FIG. 19 is a flowchart for describing an operation of controlling driving of the cooling device 10000 according to an embodiment of the present application.

The cooling device 10000 according to an embodiment of the present application may receive a signal corresponding to a user input (S4100), detect a duration of the received user input (S4300), and perform an operation according to the duration (S4500).

The cooling device 10000 according to an embodiment of the present application may acquire a signal corresponding to a user input (S4100). The cooling device 10000 may include the input unit 6300, and the input unit 6300 may acquire the signal corresponding to the user input.

For example, the input unit 6300 may be implemented using a keyboard, a keypad, a button, a jog/shuttle, a wheel, and the like. Also, the user input may be pressing a button, touching, dragging, and the like. However, the above are merely some embodiments of the user input and the input unit 6300, and the user input and the input unit 6300 should not be interpreted as being limited thereto.

As a more specific example, the cooling device 10000 according to an embodiment of the present application may receive a signal corresponding to an operation in which a switch is pressed.

The cooling device 10000 according to an embodiment of the present application may detect a duration of a user input (S4300). The control unit 5000 may check a duration of reception of a signal corresponding to the user input that is received through the input unit 6300.

As a more specific example, the cooling device 10000 according to an embodiment of the present application may detect a time during which the signal corresponding to the operation in which the switch is pressed is continuously received. The cooling device 10000 may check the duration of the reception of the signal corresponding to the user input on the basis of a first time point at which the signal corresponding to the operation in which the switch is pressed is detected for the first time and a second time point at which the detection of the signal corresponding to the operation in which the switch is pressed is ended.

The cooling device 10000 according to an embodiment of the present application may perform an operation according to a duration of a user input. The control unit 5000 may be set to perform an operation corresponding to a detected duration of a user input (S4500).

The control unit 5000 may operate the valve 2100 in a case in which a duration of an input received by the input unit 6300 is a predetermined time or more. The control unit 5000 may not operate the valve 2100 in a case in which the duration of the input received by the input unit 6300 has not reached the predetermined time.

As a more specific example, the control unit 5000 may control the valve 2100 to be in the open state during a first time in a case in which a duration of an input received by the input unit 6300 is a predetermined time or more. The control unit 5000 may control the valve 2100 to be in the closed state in a case in which the duration of the input received by the input unit 6300 has not reached the predetermined time. The duration of the input and an operation time of the valve 2100 may not be proportional.

According to an embodiment of the present application, the cooling device 10000 may include a plurality of input units 6300. The cooling device 10000 including the plurality of input units 6300 may control the cooling device 10000 on the basis of a user input that is made through at least one input unit 6300 of the plurality of input units 6300. As a specific example, in a case in which the cooling device includes at least a first input unit 6300 and a second input unit 6300, the control unit 5000 may operate the valve 2100 on the basis of a user input that is made through the first input unit 6300. As another specific example, in a case in which the cooling device includes at least the first input unit 6300 and the second input unit 6300, the control unit 5000 may operate the valve 2100 on the basis of a first user input made through the first input unit 6300 and a second input unit made through the second input unit 6300.

6. Control for Preventing Excessive Temperature Rise

The cooling device 10000 according to an embodiment of the present application may perform a function of preventing at least one element of the cooling device 10000 from reaching a high temperature. The control unit 5000 may perform a function of preventing at least one element of the cooling device 10000 from reaching a high temperature. For example, the control unit 5000 may perform a function of preventing the cryogen state regulation unit 3000 from reaching a high temperature. As a more specific example, the control unit 5000 may perform a function of preventing the heating element of the cooling device 10000 from reaching a high temperature.

The cooling device 10000 according to an embodiment of the present application may use a cryogen flowing in the cooling device 10000 in cooling the heating element in order to prevent damage to the heating element due to an excessive temperature rise of the heating element.

In order to prevent damage to the heating element due to the excessive temperature rise of the heating element, the control unit 5000 may control a closing time point of the valve 2100 in association with a time point at which driving of the heating element ends.

Figure 20:
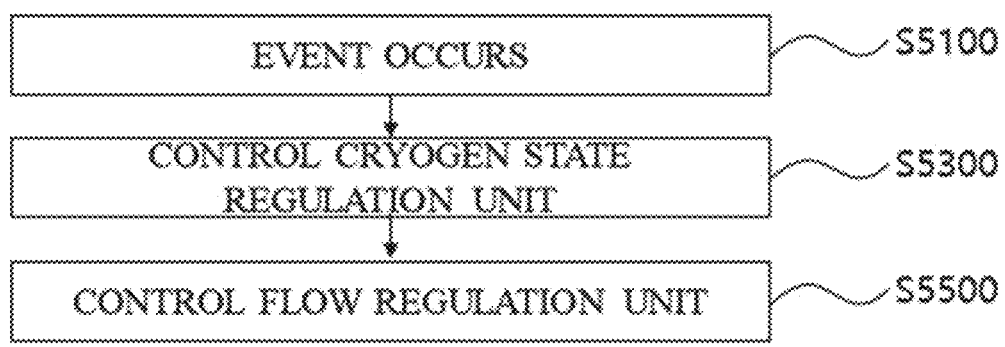
FIGS. 20 and 21 are views for describing an operation for preventing an excessive temperature rise of the cooling device according to an embodiment of the present application.

FIG. 20 is a view for describing an operation for preventing an excessive temperature rise of the cooling device 10000 according to an embodiment of the present application.

According to an embodiment of the present application, the control unit 5000 may end driving of the heating element before closing of the valve 2100 and may control the heating element and the valve 2100 so that the cryogen, which passed through the valve 2100 from the time point at which driving of the heating element ended to the time point at which the closing operation of the valve 2100 was performed, is used in cooling the heating element.

Here, the valve 2100 may be disposed downstream from the reservoir 1100 in the flow path formed in the cooling device 10000. The heating element may be disposed downstream from the reservoir 1100 in the flow path formed in the cooling device 10000. The heating element may be disposed downstream from the valve 2100 in the flow path formed in the cooling device 10000.

The cooling device 10000 according to an embodiment of the present application may, when an event occurs (S5100), control the cryogen state regulation unit 3000 (S5300) and control the flow regulation unit 2000 (S5500).

A time point at which the event occurs may be a time point at which an operation of closing the valve 2100 for a predetermined time or more should be performed. For example, in the case of the cooling device 10000 which performs an operation of opening the valve 2100 during a first time and closing the valve 2100 after the first time elapses, a time point at which the first time has elapsed with the valve 2100 open may be a time point at which an event has occurred.

The control unit 5000 may control the cryogen state regulation unit 3000. The control unit 5000 may transmit a signal for ending the operation of the heating element.

The control unit 5000 may control the flow regulation unit 2000. The control unit 5000 may transmit a signal for closing the valve 2100.

The control unit 5000 may, prior to transmitting the signal for closing the valve 2100 to the valve 2100, transmit the signal for ending the operation of the heating element to the heating element. Through such an operation, the control unit 5000 according to an embodiment of the present application may control the heating element and the valve 2100 in association, thereby performing a function of preventing an excessive temperature rise of the heating element and preventing damage to the heating element.

Figure 21:
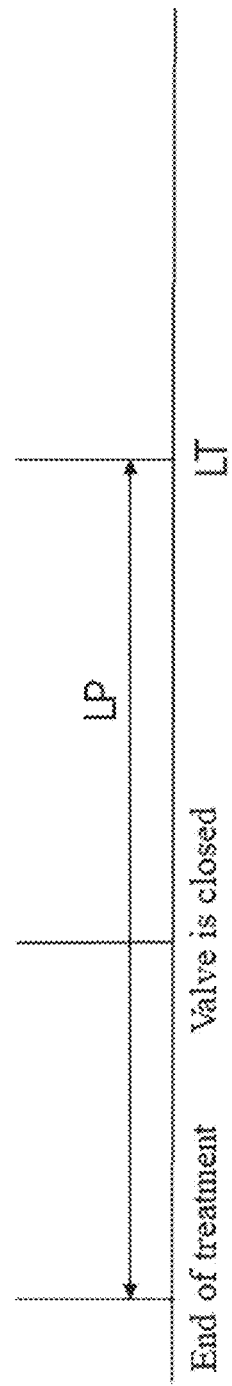

FIG. 21 is a view for describing an operation for preventing an excessive temperature rise of the cooling device 10000 according to an embodiment of the present application.

According to an embodiment of the present application, the control unit 5000 may perform a function of preventing an excessive temperature rise of the heating element and preventing damage to the heating element by ending the driving of the heating element within a limiting period LP which includes a time point at which closing of the valve 2100 starts.

Here, the valve 2100 may be disposed downstream from the reservoir 1100 in the flow path formed in the cooling device 10000. The heating element may be disposed downstream from the reservoir 1100 in the flow path formed in the cooling device 10000. The heating element may be disposed downstream from the valve 2100 in the flow path formed in the cooling device 10000.

Alternatively, here, the valve 2100 may be disposed downstream from the reservoir 1100 in the flow path formed in the cooling device 10000. The heating element may be disposed downstream from the reservoir 1100 in the flow path formed in the cooling device 10000. The valve 2100 may be disposed downstream from the heating element in the flow path formed in the cooling device 10000.

The limiting period LP according to an embodiment of the present application may be determined according to performance of the heating element. The limiting period LP may be determined according to a driving time of the cooling device 10000. The limiting period LP may be determined according to specific heat (unit: J/K) of the cryogen state regulation unit 3000. The limiting period LP may be a predetermined period.

The limiting period LP may be at least after a time point at which treatment is ended. The limiting period LP may be at least before a limiting time point LT which is set to prevent an excessive temperature rise of the heating element. The limiting period LP may include at least a closing time point of the valve 2100. The limiting period LP may be a period from the time point at which treatment is ended to the limiting time point LT set to prevent the excessive temperature rise of the heating element.

The control unit 5000 according to an embodiment of the present application may transmit a signal for opening or closing of the valve 2100 and stop driving of the heating element within a predetermined time from a time point at which the transmission of the signal is ended. The signal may be a pulse signal. Alternatively, the signal may be a continuous signal.

The control unit 5000 according to an embodiment of the present application may transmit a signal for opening or closing of the valve 2100 and stop driving of the heating element within the limiting period LP when an event which causes the valve 2100 to be kept closed for a predetermined time or more occurs.

By the above-described control unit 5000 which controls the valve 2100 and the spraying temperature controller 3100 in association, the cooling device 10000 according to an embodiment of the present application may allow a cryogen in a first temperature range to be sprayed and then a cryogen in a second temperature range to be sprayed through the spraying unit 4000. Here, the first temperature range may include a temperature of a cryogen heated by the cryogen temperature pressure controller 3100, and the second temperature range may include a temperature of a cryogen sprayed after driving of the cryogen temperature pressure controller 3100 is ended.

Cooling Device 10000 According to First Embodiment

Figure 22:
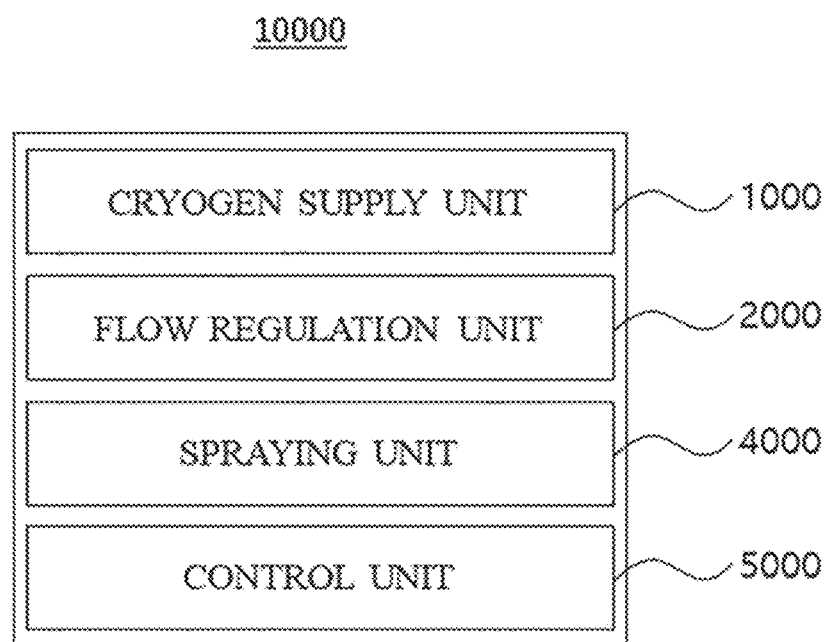
FIG. 22 is a view for describing a cooling device according to a first embodiment of the present application.

FIG. 22 is a view for describing a cooling device 10000 according to a first embodiment of the present application.

The cooling device 10000 according to the first embodiment of the present application may include a cryogen supply unit 1000, a flow regulation unit 2000, a spraying unit 4000, and a control unit 5000.

As a more specific example, the cooling device 10000 according to the first embodiment of the present application may include a cartridge as the cryogen supply unit 1000. The cooling device 10000 according to the first embodiment of the present application may include a solenoid valve 2100 as the flow regulation unit 2000. The cooling device 10000 according to the first embodiment of the present application may include a nozzle as a nozzle unit 4100. The cooling device 10000 according to the first embodiment of the present application may include a controller as the control unit 5000.

Figure 23:
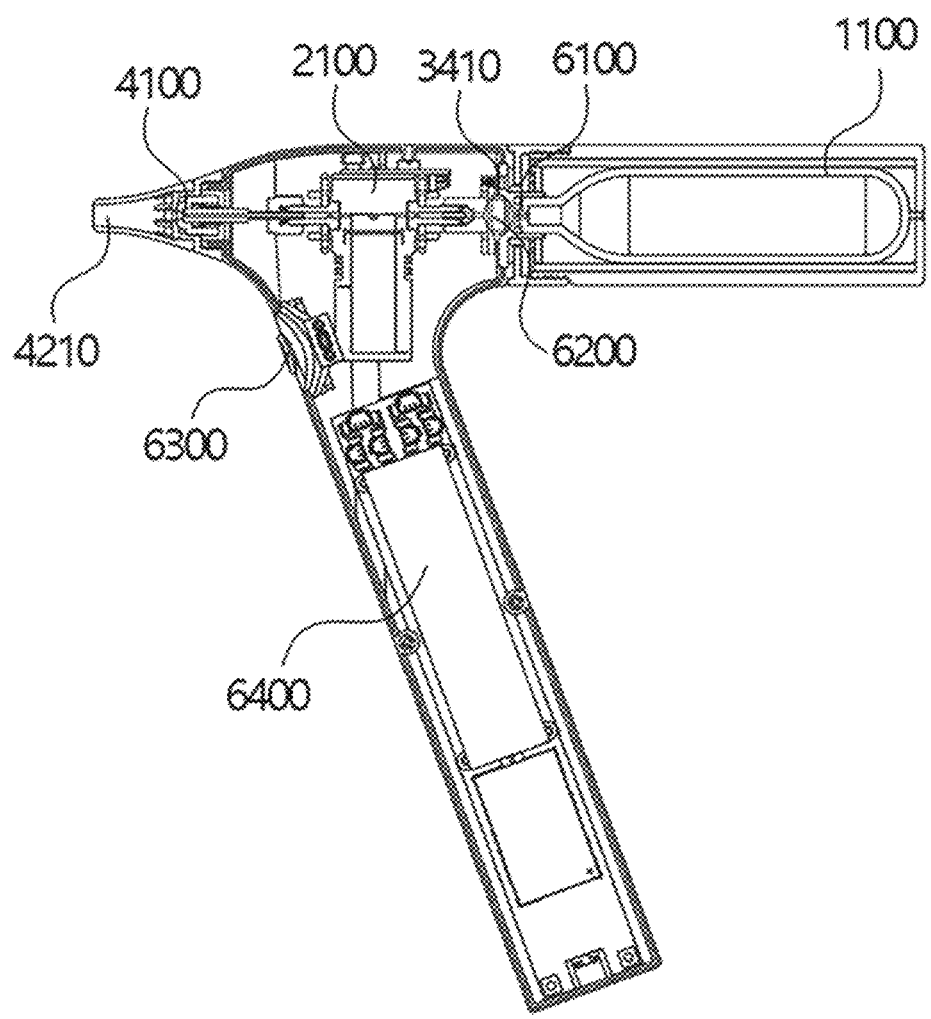
FIG. 23 is a cross-sectional view of the cooling device according to the first embodiment of the present application.

FIG. 23 is a cross-sectional view of the cooling device 10000 according to the first embodiment of the present application.

The cooling device 10000 may include a reservoir 1100. The reservoir 1100 may be a cartridge accommodating a cryogen. As a specific example, the reservoir 1100 may be a cartridge accommodating $CO_2$.

The cooling device 10000 may include the solenoid valve 2100. The solenoid valve 2100 may perform discharge of a fluid and blockage of the fluid discharge in response to an electrical signal. As a more specific example, the solenoid valve 2100 may include an inlet into which the fluid flows, an outlet from which the fluid is discharged, a plunger configured to reciprocate to block a flow of the fluid, and an armature configured to generate an induced magnetic force.

In response to an electrical signal applied thereto, the solenoid valve 2100 may generate an electromagnetic force at the armature and change the plunger to an open state. The solenoid valve 2100 may remove the electromagnetic force generated at the armature and change the plunger to a closed state.

The cooling device 10000 may include the nozzle unit 4100. The nozzle unit 4100 may be provided in the form in which a cross-sectional area of a first end and a cross-sectional area of a second end are different. The nozzle unit 4100 may be provided in the form in which a cross-sectional area of a first end which is relatively more spaced apart from the cartridge is smaller than a second cross-sectional area. Here, since resistance applied to the fluid flow increases due to a decrease in the cross-sectional area of the first end, the nozzle unit 4100 may perform a function of allowing a constant amount of cryogen to be jetted to the outside of the cooling device 10000.

The cooling device 10000 may include a controller. The controller may generate a control signal for controlling the on/off and/or the opening/closing amount of the solenoid valve 2100 and transmit the generated control signal to the solenoid valve 2100.

The cooling device 10000 may include at least one pipe. The pipe may be used in forming a flow path to jet the cryogen discharged from the reservoir 1100 in the cooling device 10000 to the outside through the nozzle unit 4100.

The cooling device 10000 may include a pipe that involves in forming a flow path between a cryogen discharge port of the reservoir 1100 and the inlet of the solenoid valve 2100. At least one pipe may be disposed between the cryogen discharge port of the reservoir 1100 and the inlet of the solenoid valve 2100.

In a case in which a plurality of pipes are disposed between the cryogen discharge port of the reservoir 1100 and the inlet of the solenoid valve 2100, a first pipe and a second pipe may be connected in a form that does not cause much leakage of cryogen and form a flow path. As a specific example, the first pipe and the second pipe may be connected in the form of being fitted and coupled.

The cooling device 10000 may include a pipe that involves in forming a flow path between the outlet of the solenoid valve 2100 and a cryogen discharge port of the nozzle unit 4100.

In a case in which a plurality of pipes are disposed between the outlet of the solenoid valve 2100 and the cryogen discharge port of the nozzle unit 4100, a third pipe and a fourth pipe may be connected in a form that does not cause much leakage of cryogen and form a flow path. As a specific example, the third pipe and the fourth pipe may be connected in the form of being fitted and coupled.

The cooling device 10000 may further include a limited-capacity cryogen reservoir 3410 capable of accommodating a cryogen by a specific volume. The limited-capacity cryogen reservoir 3410 may accommodate a predetermined amount of cryogen.

The limited-capacity cryogen reservoir 3410 may be disposed between the solenoid valve 2100 and the reservoir 1100. An inflow port of the limited-capacity cryogen reservoir 1100 may be connected to the reservoir 1100 to allow a fluid to move. An outflow port of the limited-capacity cryogen reservoir 3410 may be connected to the solenoid valve 2100 to allow the fluid to move.

The cryogen may be movable from the reservoir 1100 to the limited-capacity cryogen reservoir 3410. Regardless of the opening and closing of the solenoid valve 2100, the cryogen may be in a state in which it is movable from the reservoir 1100 to the limited-capacity cryogen reservoir 3410.

The cryogen may be movable from the limited-capacity cryogen reservoir 3410 to the inlet of the solenoid valve 2100. Regardless of the opening and closing of the solenoid valve 2100, the cryogen may be in a state in which it is movable from the limited-capacity cryogen reservoir 3410 to the inlet of the solenoid valve 2100.

The cryogen may be movable from the limited-capacity cryogen reservoir 3410 to the outlet of the solenoid valve 2100. In a state in which the solenoid valve 2100 is open, the cryogen may be movable from the limited-capacity cryogen reservoir 3410 to the outlet of the solenoid valve 2100. However, in a state in which the solenoid valve 2100 is closed, movement of the cryogen from the limited-capacity cryogen reservoir 3410 to the outlet of the solenoid valve 2100 may be blocked.

A first pipe connected to the inflow port of the limited-capacity cryogen reservoir 3410 may have a relatively smaller cross-sectional area as compared with a second pipe connected to the outflow port of the limited-capacity cryogen reservoir 3410. The resistance loaded to the flow of the cryogen in the first pipe may be higher than the resistance loaded to the flow of the cryogen in the second pipe. That is, a pressure drop of the cryogen in the first pipe may be greater than a pressure drop of the cryogen in the second pipe. Here, a temperature drop of the cryogen in the first pipe may be greater than a temperature drop of the cryogen in the second pipe.

In the case of the cooling device 10000 in which a first pipe having a significantly smaller cross-sectional area than a second pipe is formed, the first pipe may serve as the flow-rate restriction unit 2200. In other words, in a case in which the first pipe has a sufficiently smaller cross-sectional area as compared with a plurality of other pipes formed in the cooling device 10000, a flow-rate passing through at least the first pipe may be determined as a flow-rate discharging from the cooling device 10000. Therefore, even in a case in which the solenoid valve 2100 is damaged, a flow-rate being carried away from the cooling device 10000 may be determined on the basis of the flow passing through the first pipe.

Also, in a case in which the cooling device 10000 according to an embodiment of the present application performs cooling in the form in which the valve 2100 is controlled to perform opening and closing during a predetermined short time, a flow-rate of the cryogen in the first pipe may be less than a flow-rate of the cryogen in the second pipe during the predetermined short time. Here, the amount of cryogen included in the limited-capacity cryogen reservoir 3410 may be reduced instantaneously.

However, in a case in which the cooling device 10000 according to an embodiment of the present application performs cooling in the form in which the valve 2100 is controlled to be open for a predetermined time or more, the flow-rate of the cryogen in the first pipe and the flow-rate of the cryogen in the second pipe may be substantially the same. Here, a pressure drop of the cryogen in the first pipe may be greater than a pressure drop of the cryogen in the second pipe.

The first pipe connected to the inflow port of the limited-capacity cryogen reservoir 3410 may lie on a virtual straight line with the second pipe connected to the outflow port of the limited-capacity cryogen reservoir 3410. The first pipe connected to the inflow port of the limited-capacity cryogen reservoir 3410 and the second pipe connected to the outflow port of the limited-capacity cryogen reservoir 3410 may be parallel but disposed on different planes. The first pipe connected to the inflow port of the limited-capacity cryogen reservoir 3410 may be disposed not to be parallel with the second pipe connected to the outflow port of the limited-capacity cryogen reservoir 3410.

In another embodiment, the first pipe connected to the inflow port of the limited-capacity cryogen reservoir 3410 may have substantially the same cross-sectional area as the second pipe connected to the outflow port of the limited-capacity cryogen reservoir 3410. The flow-rate of the cryogen in the first pipe may be substantially the same as the flow-rate of the cryogen in the second pipe. The pressure of the cryogen in the first pipe may be substantially the same as the pressure of the cryogen in the second pipe.

The cooling device 10000 may further include a filter 6200 for filtering impurities from a cryogen flowing in the cooling device 10000. The filter 6200 may be installed in at least one region of the flow path through which the cryogen flows in the cooling device 10000. The filter 6200 may have a form corresponding to a cross-sectional shape of a pipe. The filter 6200 may be formed of a porous material. The filter 6200 may be formed of metallic mesh. The filter 6200 may be formed of a material including paper or fiber. The filter 6200 may be formed of a hydrophobic material.

As a specific example, the filter 6200 may be disposed in the limited-capacity cryogen reservoir 3410. In the case in which the filter 620 is disposed in the limited-capacity cryogen reservoir 3410, there is an advantage in that the limited-capacity cryogen reservoir 3410 has a relatively large cross-sectional area and thus is possible to secure a contact area between the cryogen and the filter 6200.

Comparing cross-sectional areas of an inflow unit of the limited-capacity cryogen reservoir 3410 into which the cryogen flows, an outflow unit of the limited-capacity cryogen reservoir 3410 from which the cryogen is discharged, and the limited-capacity cryogen reservoir 3410, the cross-sectional area of the limited-capacity cryogen reservoir 3410 may be relatively larger than the cross-sectional area of the inflow unit and the cross-sectional area of the outflow unit.

A cross-sectional area of the filter 6200 may be larger than at least one of the cross-sectional area of the inflow unit and the cross-sectional area of the outflow unit. The cross-sectional area of the filter 6200 may be larger than at least one of a cross-sectional area of a first flow path connected to the inflow unit and a cross-sectional area of a second flow path connected to the outflow unit. As a specific example, the cross-sectional area of the filter 6200 may be relatively larger than the cross-sectional area of the inflow unit and the cross-sectional area of the outflow unit.

Also, according to an embodiment of the present application, the filter 6200 may be fitted and coupled to the limited-capacity cryogen reservoir 3410. The cross-sectional area of the filter 6200 may be less than or equal to the cross-sectional area of the limited-capacity cryogen reservoir 3410.

Figure 24:
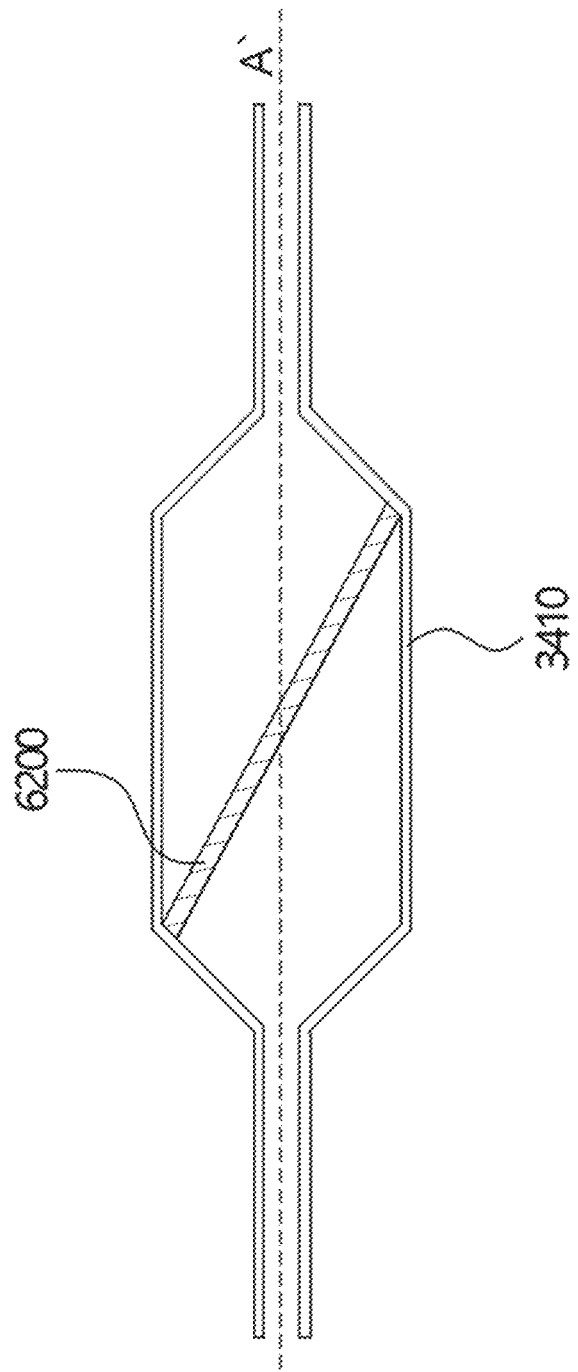
FIG. 24 is a view for describing a filter and a limited-capacity cryogen reservoir according to another embodiment of the present application.

FIG. 24 is a view for describing a filter 6200 and the limited-capacity cryogen reservoir 3410 according to another embodiment of the present application.

As illustrated in FIG. 23, the filter 6200 may be installed in the limited-capacity cryogen reservoir in a direction perpendicular to a direction in which the cryogen moves in the limited-capacity cryogen reservoir 3410. The filter 6200 may be installed in the limited-capacity cryogen reservoir in a direction perpendicular to a direction in which the cryogen moves from the reservoir 1100 to the nozzle unit 4100.

According to another embodiment of the present application, as illustrated in FIG. 24, the filter 6200 may be installed in the limited-capacity cryogen reservoir 3410 so as not to be perpendicular to the direction in which the cryogen moves in the limited-capacity cryogen reservoir 3410. The filter 6200 may be fitted and coupled to the limited-capacity cryogen reservoir 3410 in a direction not perpendicular to the direction in which the cryogen moves in the limited-capacity cryogen reservoir 3410.

The first pipe connected to the inflow port of the limited-capacity cryogen reservoir 3410 may lie on a virtual straight line A' with the second pipe connected to the outflow port of the limited-capacity cryogen reservoir 3410.

Although not illustrated, according to another embodiment of the present application, the first pipe connected to the inflow port of the limited-capacity cryogen reservoir 3410 and the second pipe connected to the outflow port of the limited-capacity cryogen reservoir 3410 may be parallel but disposed on different planes. When the filter 6200 is installed in the limited-capacity cryogen reservoir 3410 in a direction of tilting counterclockwise from a state of being perpendicular to the direction in which the cryogen moves in the limited-capacity cryogen reservoir 3410, the first pipe may be disposed relatively higher than the second pipe.

The filter 6200 has been described above according to some embodiments, but the filter 6200 may have various other positions, forms, materials, and the like. The position, form, and material of the filter 6200 may be simply selected by those of ordinary skill in the art, and thus position, form, and material of the filter 6200 should not be interpreted as being limited by those stated as examples in the present application.

A perforation structure 6100 for perforating the reservoir 1100 may be formed in the cooling device 10000. In a case in which the cooling device 10000 includes the reservoir 1100, the reservoir 1100 is provided in a replaceable form in some cases. In this case, when the reservoir 1100 is mounted on the cooling device 10000, the cooling device 10000 has to perform an operation of perforating to allow leakage of a fluid stored in the reservoir 1100. Thus, the perforation structure 6100 for perforating the reservoir 1100 may be formed in the cooling device 10000.

The perforation structure 6100 may be formed in any one region of the flow path formed between the reservoir 1100 and the inlet of the solenoid valve 2100.

The perforation structure 6100 may be formed in any one region of the flow path formed between the reservoir 1100 and the inlet of the limited-capacity cryogen reservoir 3410.

The perforation structure 6100 may be formed at one end of the flow path formed between the reservoir 1100 and the inlet of the solenoid valve 2100. The perforation structure 6100 may be formed at one end of the flow path formed between the reservoir 1100 and the inlet of the limited-capacity cryogen reservoir 3410.

Figure 25:
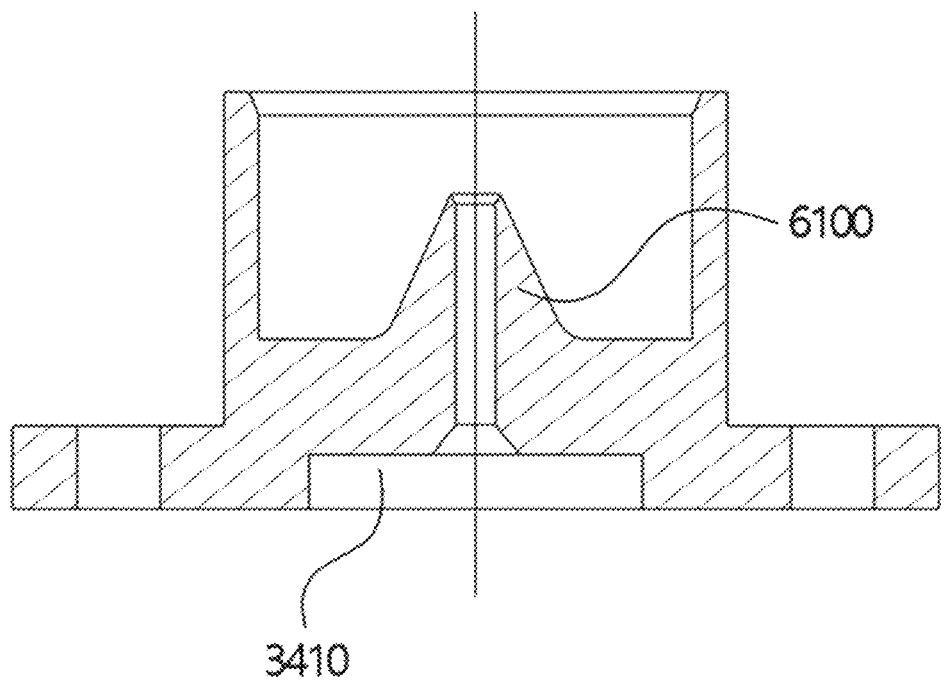
FIG. 25 is a view for describing a perforation structure of the cooling device according to an embodiment of the present application.

FIG. 25 is a view for describing the perforation structure 6100 of the cooling device 10000 according to an embodiment of the present application.

The cooling device 10000 may include, as the perforation structure 6100, a region in which an outer diameter of one end of the flow path gradually decreases. A region in which the outer diameter of the one end of the flow path is the smallest may be formed at a position more adjacent to the reservoir 1100 than a region in which the outer diameter of the one end of the flow path is the largest.

According to an embodiment of the present application, the perforation structure 6100 may perform a function of preventing the cryogen of the reservoir 1100 from being carried away. The perforation structure 6100 may perforate the reservoir 1100 and be disposed within a predetermined distance from the reservoir 1100. Here, the perforation structure 6100 may perform a function of preventing the cryogen from being carried away from the reservoir 1100.

As a specific example, the perforation structure 6100 may have a structure in which an outer diameter gradually decreases. The structure in which the outer diameter gradually decreases may form an inclined surface at an outer surface of the perforation structure 6100. The inclined outer surface of the perforation structure 6100 may directly come in close contact with a perforated portion of the reservoir 1100. Since the inclined outer surface of the perforation structure 6100 comes in close contact with the perforated portion of the reservoir 1100, even without a separate O-ring, it is possible to prevent leakage of the cryogen stored in the reservoir 1100 to the outside. In a case in which the perforation structure 6100 directly forms the reservoir 1100 and a sealing, even when the reservoir 1100 is separated from the perforation structure 6100, it is possible to derive an effect in that the cryogen remaining in the reservoir 1100 may smoothly come out.

The perforation structure 6100 may be formed of a material with a relatively high stiffness. The perforation structure 6100 may be formed of a material with a relatively high wear resistance. An outer side of the perforation structure 6100 may be formed of a material with a relatively higher stiffness or wear resistance as compared with the reservoir 1100.

The perforation structure 6100 may have a form in which it is coated with a material with a relatively high stiffness or wear resistance. An inner side of the perforation structure 6100 may be formed of the same material as the pipe of the cooling device 10000 and have a form in which the outer side of the perforation structure 6100 is coated with a material with a high stiffness.

The cooling device 10000 may further include an input unit 6300. The input unit 6300 may acquire a signal corresponding to a user input. The input unit 6300 may be implemented using a keyboard, a keypad, a button, a jog/shuttle, a wheel, and the like. The input unit 6300 may be a key pad utilized as a switch.

The cooling device 10000 may include a switch which generates an electrical signal in response to user contact. The switch may perform a function of generating an electrical signal in response to generation of an electrical or electrostatic signal according to user contact. Alternatively, the switch may perform a function of generating an electrical signal in response to generation of a pressure of a predetermined numerical value or higher according to user contact.

The cooling device 10000 may further include a power supply unit. The cooling device 10000 may further include a power supply unit which supplies power for driving the cooling device 10000. The power supply unit may include at least one of a direct-current power source for supplying direct current and an alternating-current power source for supplying alternating current. For example, the power supply unit may be a secondary battery.

The power supply unit may supply power to the control unit 5000. The power supply unit may supply power to the solenoid valve 2100. The power supply unit may supply power for controlling opening and closing of the solenoid valve 2100.

The cooling device 10000 according to an embodiment of the present application may be implemented in various forms. For example, the cooling device 10000 may have an elongated body. The cooling device 10000 may have a T-shaped body. The cooling device 10000 may have a C-shaped body.

Figure 26:
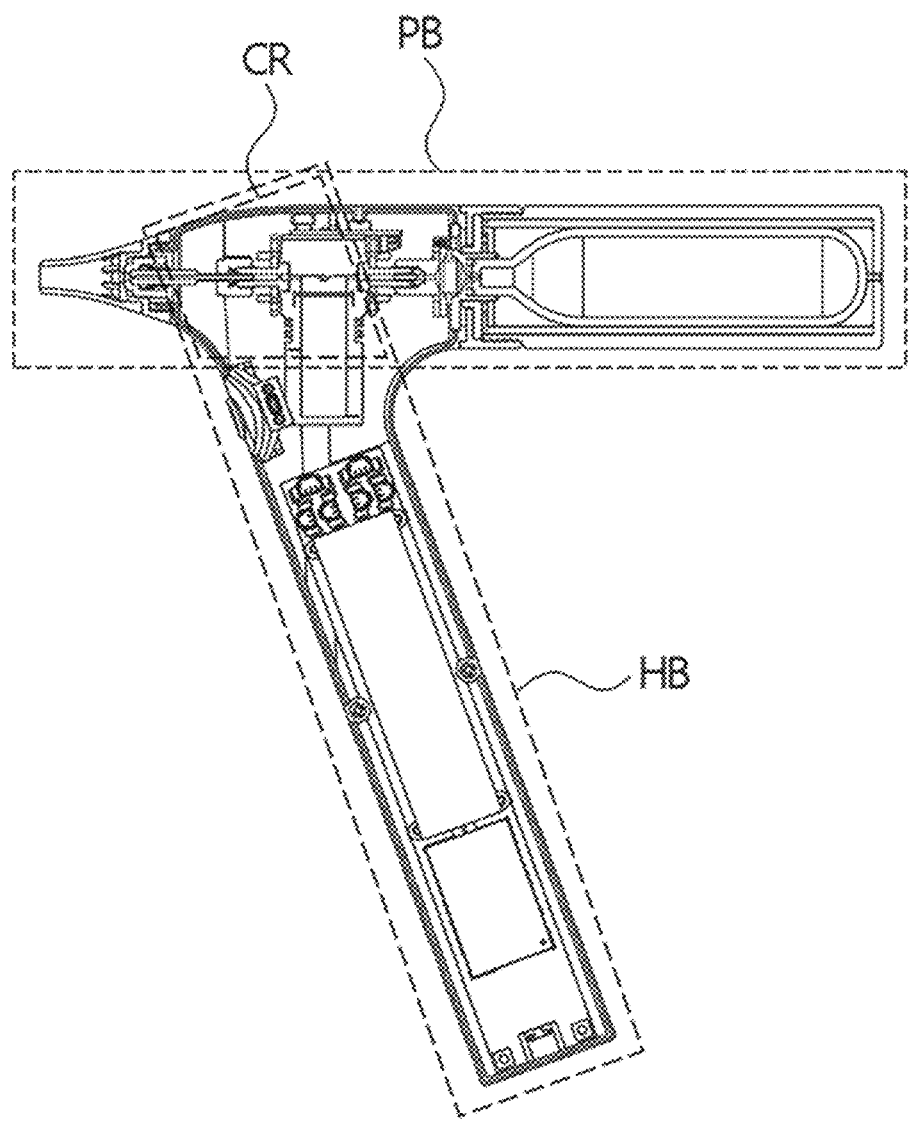
FIG. 26 is a view for describing a horizontal body PB and a hand body HB of the cooling device according to the first embodiment of the present application.

FIG. 26 is a view for describing a horizontal body PB and a hand body HB of the cooling device 10000 according to the first embodiment of the present application.

The cooling device 10000 according to the first embodiment of the present application may have a T-shaped body. The cooling device 10000 may have a T-shaped body including the horizontal body PB and the hand body HB.

The hand body HB may be spaced a predetermined distance apart from a front end of the horizontal body PB. The hand body HB may be integrally formed to have a predetermined angle with the horizontal body PB.

According to an embodiment of the present application, the reservoir 1100 may be disposed at one end of the horizontal body PB (hereinafter referred to as a rear end of the horizontal body PB). The nozzle unit 4100 may be disposed at the other end of the horizontal body PB (hereinafter referred to as the front end of the horizontal body PB).

The inlet of the solenoid valve 2100 may be disposed at the rear end of the horizontal body PB. A flow path through which a fluid may move may be formed between the inlet of the solenoid valve 2100 and the reservoir 1100, and the flow path may be disposed at the rear end of the horizontal body PB.

The outlet of the solenoid valve 2100 may be disposed at the front end of the horizontal body PB. A flow path through which a fluid may move may be formed between the outlet of the solenoid valve 2100 and the nozzle unit 4100, and the flow path may be disposed at the front end of the horizontal body PB.

The power supply unit may be disposed at the hand body HB. The input unit 6300 may be disposed at the hand body HB. The control unit 5000 may be disposed at the hand body HB.

The valve 2100 may be disposed in a region CR in which the horizontal body PB and the hand body HB are connected. According to circumstances, the armature of the solenoid valve 2100 may be disposed at an upper end of the hand body HB.

The flow path through which a fluid may move between the outlet of the solenoid valve 2100 and the nozzle unit 4100 may be formed in a second direction, which is parallel to or the same as a first direction in which the flow path through which a fluid may move between the inlet of the solenoid valve 2100 and the reservoir 1100 is formed.

The plunger may reciprocate between the inlet of the solenoid valve 2100 and the reservoir 1100 in a third direction, which is a direction perpendicular to the first direction in which the flow path through which a fluid may move is formed.

The cooling device 10000 according to another embodiment of the present application may be implemented in the form in which the reservoir 1100 is disposed at the hand body HB and the power supply unit is disposed at the rear end of the horizontal body PB.

The valve 2100 may be disposed in the region CR in which the horizontal body PB and the hand body HB are connected. According to circumstances, the armature of the solenoid valve 2100 may be disposed at the rear end of the horizontal body PB.

The structure of the cooling device 10000 according to the first embodiment has been described above with reference to some embodiments.

However, the design of the structure of the cooling device 10000 may be easily changed according to user convenience and the need of a producer, and the scope of the present application is not limited to the above-described embodiment.

The cooling device 10000 according to the first embodiment of the present application may perform the above-described cooling control, dynamic cooling control, provision of vibration, cryogen spraying uniformity control, driving control of the cooling device 10000, and/or control for preventing an excessive temperature rise.

Specific operations in which the cooling device 10000 according to the first embodiment performs the cooling control, the dynamic cooling control, the provision of vibration, the cryogen spraying uniformity control, the driving control of the cooling device 10000, and/or the control for preventing an excessive temperature rise have been described in detail above, and thus detailed descriptions thereof will be omitted.

However, in relation to an operation in which the cooling device 10000 according to the first embodiment performs the cooling control, a specific embodiment related to a pipe structure of the cooling device 10000 according to the first embodiment will be described below.

FIGS. 27 and 28 are views for describing an operation of the cooling device 10000 according to an embodiment of the present application.

When the valve 2100 of the cooling device 10000 is controlled to an open state, the cooling device 10000 may discharge a cryogen and cool a target region TR. The control unit 5000 may control the valve 2100 to the open state so that the cryogen is continuously sprayed to the target region TR for a predetermined time. The discharged cryogen may have a temperature lower than room temperature, and at least a portion of the discharged cryogen may reach the target region TR and cool the target region TR.

The phenomenon in which the discharged cryogen has a temperature lower than room temperature may be induced by expansion and contraction of the cryogen in the cooling device 10000.

A first point P1, a second point P2, a third point P3, a fourth point P4, a fifth point P5, a sixth point P6, and a seventh point P7 may correspond to an outflow unit of the guide unit, an outflow unit of the nozzle unit 4100, an outflow unit of the solenoid valve 2100, an inflow unit of the solenoid valve 2100, the limited-capacity cryogen reservoir 3410, a pipe inside the perforation structure 6100, and one point inside the reservoir 1100, respectively.

When the control unit 5000 opens the valve 2100 in order to cause the cryogen to discharge from the reservoir 1100, the cryogen, which is stored at a relatively high pressure, may expand in the limited-capacity cryogen reservoir 3410, and the pressure of the cryogen may decrease. The cryogen whose pressure is decreased in the limited-capacity cryogen reservoir 3410 may pass through the solenoid valve 2100 and reach the nozzle unit 4100. Although a small change in the pressure of the cryogen may occur while the cryogen moves from the limited-capacity cryogen reservoir 3410 to the nozzle unit 4100, this may be an insignificant change as compared with an amount of change in the pressure due to the expansion of the cryogen in the limited-capacity cryogen reservoir 3410.

When the cryogen is sprayed through the nozzle unit 4100, the pressure of the cryogen may decrease to an extent that it is close to the atmospheric pressure. In the cryogen, numerous pressure changes may occur when the cryogen moves from the reservoir 1100 to the guide unit 4210. However, particularly, when the cryogen passes through the limited-capacity cryogen reservoir 3410, a considerable pressure change may occur when the cryogen passes through the nozzle unit 4100.

Simultaneously with the pressure change of the cryogen, a temperature change of the cryogen may also occur. When the control unit 5000 opens the valve 2100 in order to cause the cryogen to discharge from the reservoir 1100, the cryogen, which is stored at a relatively high pressure, may expand in the limited-capacity cryogen reservoir 3410, and the pressure of the cryogen may decrease. The temperature of the cryogen which is expanded in the limited-capacity cryogen reservoir 3410 may significantly decrease. As a specific example, a pressure of a cryogen, which is stored at a pressure of about 57 bar in the reservoir 1100, may be changed to a pressure of about 30 bar as the cryogen passes through the limited-capacity cryogen reservoir 3410. Here, a temperature of a cryogen, which is stored at a temperature of about 25° C. in the reservoir 1100, may be changed to a temperature of about −25° C. as the cryogen passes through the limited-capacity cryogen reservoir 3410.

The cryogen whose pressure is decreased in the limited-capacity cryogen reservoir 3410 may pass through the solenoid valve 2100 and reach the nozzle unit 4100. A change in the pressure of the cryogen while the cryogen moves from the limited-capacity cryogen reservoir 3410 to the nozzle unit 4100 may be insignificant. However, the temperature of the cryogen may significantly increase through heating by an outside air temperature while the cryogen moves from the limited-capacity cryogen reservoir 3410 to the nozzle unit 4100. As a specific example, the cryogen has a pressure of about 30 bar while moving from the limited-capacity cryogen reservoir 3410 to the nozzle unit 4100 but has a temperature increasing from about −25° C. to about 10° C. while moving from the limited-capacity cryogen reservoir 3410 to the nozzle unit 4100.

When the cryogen is sprayed through the nozzle unit 4100, the pressure of the cryogen may decrease to an extent that it is close to the atmospheric pressure. As a specific example, the cryogen that passed through the limited-capacity cryogen reservoir 3410 may have a pressure of about 30 bar as the cryogen passes through the flow path formed in the cooling device 10000, and then, as the cryogen is sprayed through the nozzle unit 4100, the cryogen may have a pressure of about 1 bar. Here, the temperature of the cryogen that passed through the limited-capacity cryogen reservoir 3410 may increase and be 10° C. as the cryogen passes through the flow path formed in the cooling device 10000, and then, as the cryogen is sprayed through the nozzle unit 4100, the temperature of the cryogen may decrease to about −40° C.

The cryogen that passes through the nozzle unit 4100 and moves to one end of the guide unit 4210 may reach the target region TR while a pressure of the cryogen remains almost constant at 1 bar but the temperature of the cryogen increases to about −10° C. due to the outside air temperature. In this way, the cooling device 10000 may induce the cryogen to be expanded and/or contracted in the flow path formed therein and perform a function of providing the cryogen having a proper temperature to the target region TR.

Figure 29:
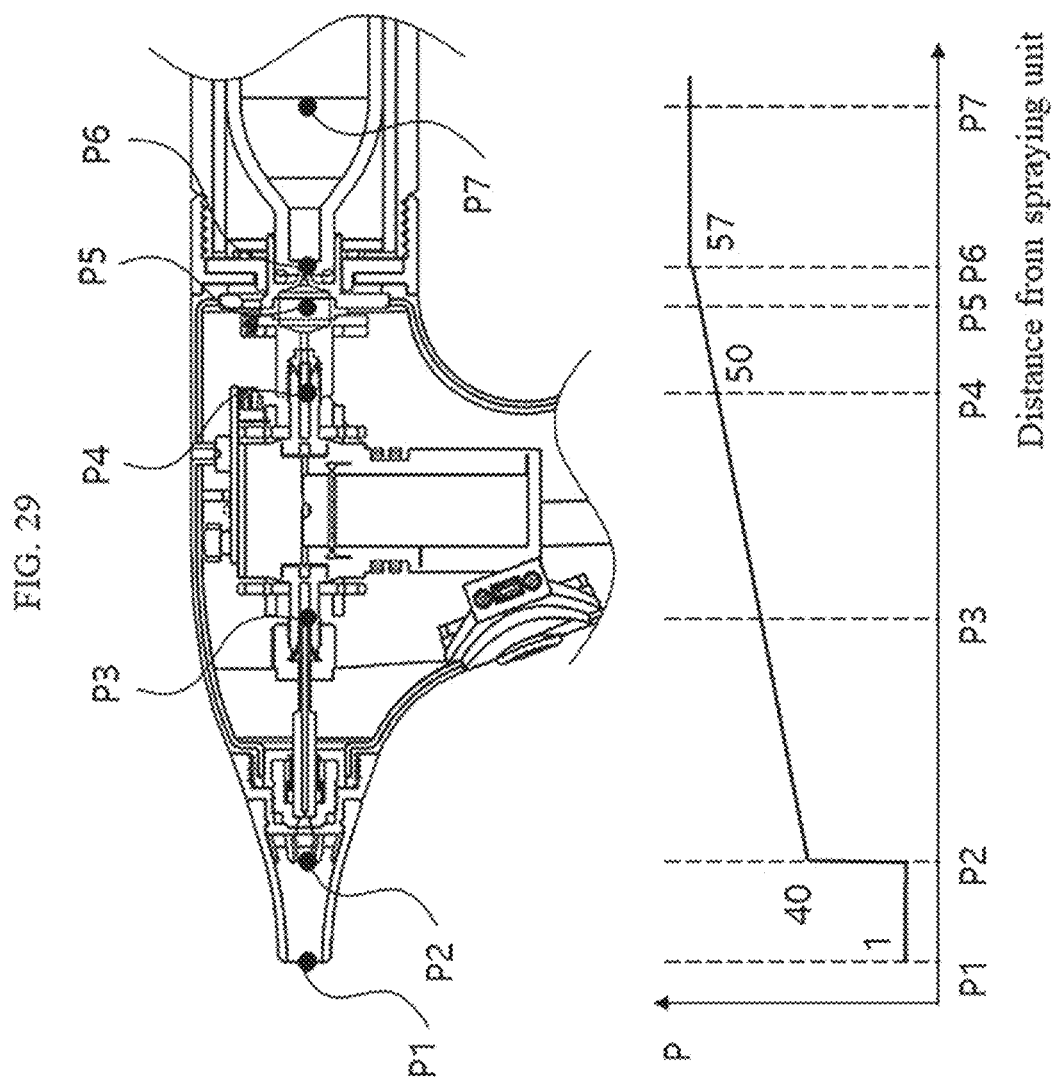

FIGS. 29 and 30 are views for describing an operation of the cooling device 10000 according to an embodiment of the present application.

The cooling device 1000 according to an embodiment of the present application may discharge a cryogen and cool the target region TR. The cooling device 10000 may discharge the cryogen in the form of performing the opening and closing of the valve 2100 multiple times. The cooling device 10000 according to an embodiment of the present application may discharge a cryogen and cool the target region TR. The cooling device 10000 may discharge the cryogen in the form of continuously performing the opening and closing of the valve 2100. As described above, the valve 2100 may repeat the opening and closing operations periodically or non-periodically.

The phenomenon in which the discharged cryogen has a temperature lower than room temperature may be induced by expansion and contraction of the cryogen in the cooling device 10000.

A first point Pt, a second point P2, a third point P3, a fourth point P4, a fifth point P5, a sixth point P6, and a seventh point P7 may correspond to an outflow unit of the guide unit, an outflow unit of the nozzle unit 4100, an outflow unit of the solenoid valve 2100, an inflow unit of the solenoid valve 2100, the limited-capacity cryogen reservoir 3410, a pipe inside the perforation structure 6100, and one point inside the reservoir 1100, respectively.

When the control unit 5000 repeats the opening and closing of the valve 2100 in order to cause the cryogen to discharge from the reservoir 1100, the cryogen, which is stored at a high pressure, may experience an insignificant pressure change until the cryogen reaches the solenoid valve 2100 after passing through the limited-capacity cryogen reservoir 3410. This may be due to a fluid being accommodated in the limited-capacity cryogen reservoir 3410 and the valve 2100 being closed before the accommodated fluid discharges entirely. In other words, the above-mentioned insignificant pressure change may be due to a phenomenon in which, as the valve 2100 repeats opening and closing, the cryogen disposed in the limited-capacity cryogen reservoir 3410 is jetted, and thus, sudden expansion of the cryogen in the limited-capacity cryogen reservoir 3410 does not occur.

The pressure of the cryogen may decrease while the cryogen passes through the outlet of the solenoid valve 2100 and reaches the nozzle unit 4100. When the cryogen is sprayed through the nozzle unit 4100, the pressure of the cryogen may decrease to an extent that it is close to the atmospheric pressure.

According to an embodiment of the present application, the pressure of the cryogen that decreases as the cryogen moves from the reservoir 1100 to the inlet of the valve 2100 may be lower than the pressure of the cryogen that decreases as the cryogen moves from the outlet of the valve 2100 to the outer side of the nozzle unit 4100.

Simultaneously with the pressure change of the cryogen, a temperature change of the cryogen may also occur.

When the control unit 5000 repeats the opening and closing of the valve 2100 in order to cause the cryogen to discharge from the reservoir 1100, the cryogen, which is stored at a high pressure, may experience an insignificant pressure change until the cryogen reaches the solenoid valve 2100 after passing through the limited-capacity cryogen reservoir 3410. The cryogen that flows into the inlet of the solenoid valve 2100 after passing through the limited-capacity cryogen reservoir 3410 from the reservoir 1100 may experience an insignificant temperature change.

As a specific example, the cryogen that flows into the inlet of the solenoid valve 2100 after passing through the limited-capacity cryogen reservoir 3410 from the reservoir 1100 may have a pressure of 57 bar and a temperature of 25° C. The cryogen that flows into the inlet of the solenoid valve 2100 after passing through the limited-capacity cryogen reservoir 3410 from the reservoir 1100 may have a pressure of about 50 bar and a temperature of about 20° C. which are slightly lower than the pressure and the temperature of the cryogen in the reservoir 1100. The pressure and temperature of the cryogen may be changed due to an influence of the outside temperature as the cryogen moves from the reservoir 1100 to the inlet of the solenoid valve 2100.

The pressure of the cryogen may somewhat decrease while the cryogen passes through the outlet of the solenoid valve 2100 and reaches the nozzle unit 4100. The temperature of the cryogen may somewhat decrease due to the pressure change and heating of the outside air while the cryogen passes through the outlet of the solenoid valve 2100 and reaches the nozzle unit 4100.

As a specific example, the pressure of the cryogen may decrease from about 50 bar to about 40 bar while the cryogen passes through the outlet of the solenoid valve 2100 and reaches the nozzle unit 4100. The temperature of the cryogen may decrease from about 20° C. to about 15° C. while the cryogen passes through the outlet of the solenoid valve 2100 and reaches the nozzle unit 4100.

When the cryogen is sprayed through the nozzle unit 4100, the pressure of the cryogen may decrease to an extent that it is close to the atmospheric pressure. As a specific example, the cryogen that passed through the limited-capacity cryogen reservoir 3410 may have a pressure of about 40 bar as the cryogen passes through the flow path formed in the cooling device 10000, and then, as the cryogen is sprayed through the nozzle unit 4100, the cryogen may have a pressure of about 1 bar. Here, the temperature of the cryogen that passed through the limited-capacity cryogen reservoir 3410 may be about 15° C. as the cryogen passes through the flow path formed in the cooling device 10000, and then, as the cryogen is sprayed through the nozzle unit 4100, the temperature of the cryogen may decrease to about −78° C.

The cryogen that passes through the nozzle unit 4100 and moves to one end of the guide unit 4210 may reach the target region TR while a pressure of the cryogen remains almost constant at 1 bar but the temperature of the cryogen increases to about −10° C. due to the outside air temperature. In this way, the cooling device 10000 may induce the cryogen to be expanded and/or contracted in the flow path formed therein and perform a function of providing the cryogen having a proper temperature to the target region TR.

According to an embodiment of the present application, the temperature of the cryogen that decreases as the cryogen moves from the reservoir 1100 to the inlet of the valve 2100 may be lower than the temperature of the cryogen that decreases as the cryogen moves from the outlet of the valve 2100 to the outer side of the nozzle unit 4100.

Even in a situation in which the control unit 5000 is unable to operate normally, and thus the valve 2100 is continuously open, the cooling device 10000 including the limited-capacity cryogen reservoir 3410 may perform safe cooling of the target region TR to about −10° C., which is similar to the temperature at the first point P1 in a state in which the valve 2100 is opened and closed during a short time due to normal control by the control unit 5000.

According to a specific embodiment of the present application, the valve 2100 may receive a pulse signal from the control unit 5000 periodically or non-periodically and control the amount of spraying material supplied, so that the cryogen may be transferred to the nozzle unit 4100 at a predetermined first temperature. The valve 2100 may receive the pulse signal, generate an electromagnetic force at the armature, change the plunger to an open state, and transfer the cryogen supplied to the first flow path, which is connected to the inlet of the valve 2100, to the second flow path, which is connected to the outlet of the valve 2100. The cryogen transferred to the second flow path may be sprayed from the nozzle unit 4100, be mixed with a flow of an external fluid present at the guide unit 4210 or freely expand before coming into contact with the target region, have the temperature changed to a second temperature, and be sprayed to the target region. While being sprayed, the sprayed cryogen may generate a predetermined pressure change periodically or non-periodically.

The operation in which the condition of the cryogen is regulated according to the expansion and contraction of the cryogen in the cooling device 10000 according to an embodiment of the present application has been described above. However, the above specific examples are merely given to assist in understanding of the present specification, and thus specific operations may be considerably changed according to the actual outside air temperature, type of cryogen, temperature of cryogen, cross-sectional area of a pipe, and the like. Therefore, in interpreting the scope of the present application, the scope of the present application should be interpreted by the claims of the present application without unnecessarily limiting the scope.

Cooling Device 10000 According to Second Embodiment

Figure 31:
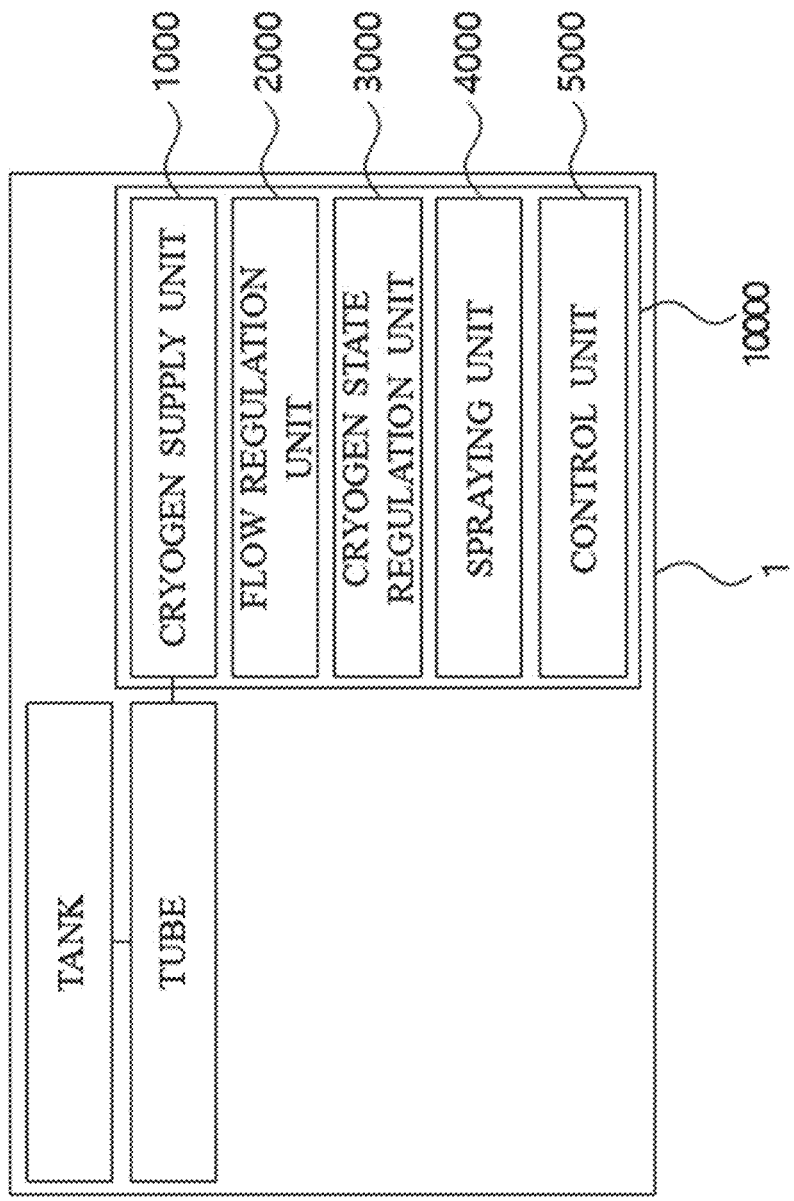
FIG. 31 is a view for describing a cooling device and a cooling system 1 according to a second embodiment of the present application.

FIG. 31 is a view for describing a cooling device 10000 and a cooling system 1 according to a second embodiment of the present application.

Referring to FIG. 31, the cooling system 1 according to an embodiment of the described technology may, in cooling a target region TR using a cryogen, include a tank configured to store the cryogen, a tube configured to transfer the cryogen to a cooling device, and the cooling device 100 disposed by the present application.

The cooling device 10000 may include a cryogen supply unit 1000, a flow regulation unit 2000, a cryogen state regulation unit 3000, a spraying unit 4000, and a control unit 5000.

As a more specific example, the cooling device 10000 according to the second embodiment of the present application may include a transfer unit 1200 as the cryogen supply unit 1000. The cooling device 10000 according to the second embodiment of the present application may include a valve as the flow regulation unit 2000.

The cooling device 10000 according to the second embodiment of the present application may include a spraying temperature controller 3100 as the cryogen state regulation unit 3000. The spraying temperature controller 3100 according to an embodiment of the present application may perform a function of controlling a temperature of a cryogen and controlling the temperature and pressure of the cryogen. In the sense that the spraying temperature controller 3100 performs a function of controlling the temperature and pressure of the cryogen, the spraying temperature controller 3100 may also be referred to as "cryogen temperature pressure controller."

The cooling device 10000 according to the second embodiment of the present application may include a cryogen cooling unit 3200 as the cryogen state regulation unit 3000. The cryogen cooling unit 3200 according to an embodiment of the present application may perform a function of controlling a temperature of a cryogen and keeping a pressure of the cryogen. In the sense that the cryogen cooling unit 3200 performs a pressure keeping function, the cryogen cooling unit 3200 may also be referred to as "cryogen pressure keeper."

The cooling device 10000 according to the second embodiment of the present application may further include a cryogen cyclone rotator 3300 configured to control a temperature of a cryogen by rotating the cryogen and increasing a contact area between the cryogen and a heating element.

The cooling device 10000 according to the second embodiment of the present application may further include a nozzle unit 4100 as the spraying unit 4000.

The cooling device 10000 according to the second embodiment of the present application may further include a heat providing barrier 4220 as the spraying unit 4000. The cooling device 10000 according to the second embodiment of the present application may further include a controller as the control unit 5000.

However, according to an embodiment of the present application, the cooling device 10000 may be provided by omitting any one of the above elements or adding other elements.

The control unit 5000 according to an embodiment of the present application may control the elements of the cooling device 10000. The control unit 5000 may control the cryogen pressure keeper 3200, the cryogen temperature pressure controller 3100, the cryogen cyclone rotator 3300, and/or the valve 2100. According to an embodiment of the described technology, at least one or more flow regulation units 2000 may be provided at necessary sites along a movement path of the cryogen, and the flow regulation unit may be electrically connected to the control unit 5000 so that the opening and closing of the flow regulation unit are controlled by control of the control unit 5000. The flow regulation unit 2000 may be implemented as a solenoid valve or the like such that the opening and closing thereof are controlled, or the flow regulation unit 2000 may be implemented as an actuator or the like and configured to also control the flow-rate of the cryogen. The at least one flow regulation unit 2000 may be electrically connected to the control unit 5000 and a spraying button so that a signal generated as the user operates the spraying button is input to the control unit 5000, the control unit 5000 controls the flow regulation unit 2000 on the basis of the input signal, and the spraying of the cryogen is smoothly performed.

The cooling device 1000 according to the described technology relates to a cooling device 10000 that controls a temperature of a sprayed cryogen. The cooling device 10000 may control the cryogen to be sprayed to the target region TR at a temperature different from an attribute temperature of the cryogen. According to an embodiment, the cooling device 10000 according to an embodiment of the present application may include controlling at least one of a target cooling temperature, a cooling speed, a target thawing temperature, and a thawing speed and dynamically control the temperature of the cryogen and, in controlling the cooling temperature, may cool the target region TR to a predetermined temperature using a parameter including heat applied to the cryogen.

The cooling device 10000 may cool any body part and may cool the skin, eyes, gums, or the like, for example.

Hereinafter, for convenience of description, the case in which the skin is cooled using the cooling device 10000 will be mainly described, but of course the described technology is not limited thereto. Also, the cooling device 10000 may be applied not only to treatment using cooling but also to a case in which anesthesia or hemostasis is required, a case in which antibacterial is required, a case in which a local site is frozen and removed such as when removing a spot, a wart, or a cool from the skin, and a case in which local anesthesia is required in a relatively short time such as during a small-scale laser procedure that involves depilation, dermabrasion, and botox.

Also, a body unit of the cooling device 10000 has an ergonomic shape so that the body unit may be gripped by a user's hand. For example, the body unit of the cooling device 10000 may be formed in any one of a pen shape or a pistol shape. Hereinafter, in the described technology, a case in which the body unit has a pistol shape will be mainly described, but the described technology is not limited thereto, and the body unit may have various other shapes.

In addition, the temperature pressure controller 3100 may be connected to the other side end of the transfer unit 1200, the cooling device 10000 may selectively spray the cryogen that flowed in through the transfer unit 1200, and a portion from which the cryogen is sprayed may be implemented in the form of a nozzle or the like. The cooling device 10000 may further include the heat providing barrier 4220 so that the cryogen sprayed from the nozzle unit 4100 cools an accurate target region through the spraying unit 4000 and cooling of regions other than the target region is prevented.

According to an embodiment of the present application, at least one or more cryogen pressure keepers 3200 may be disposed in a region where the temperature pressure controller 3100 and the transfer unit 20 are connected. The cryogen pressure keeper 3200 may keep a cryogen in a high-pressure state before the cryogen flows into the temperature pressure controller 3100 so that pressure loss of the cryogen is prevented and the cryogen is sprayed with a fast response speed.

According to an embodiment, the cryogen pressure keeper 3200 may be disposed in the cooling device 10000. According to an embodiment, the body unit may be formed of a plurality of body units, and the cryogen pressure keeper 3200 may be configured so that the cryogen pressure keeper 3200 is disposed in the body unit that may be gripped by the user.

A plurality of buttons and a display unit which are electrically connected to the control unit 5000 are disposed at an outer circumference of the body unit so as to be exposed to the outside. Spraying of the cryogen and the temperature of the cryogen may be controlled through the plurality of buttons, and the temperature/pressure of the cryogen, the temperature of the site subject to treatment, and a state of the device may be checked through the display unit. For example, among the plurality of buttons, one button may be used when automatically implementing a predetermined cooling protocol from the control unit 5000, and another button may be used when a user arbitrarily regulates cooling conditions manually by cutting off or supplying the power from or to a cryogen temperature pressure controller during operation.

Figure 32:
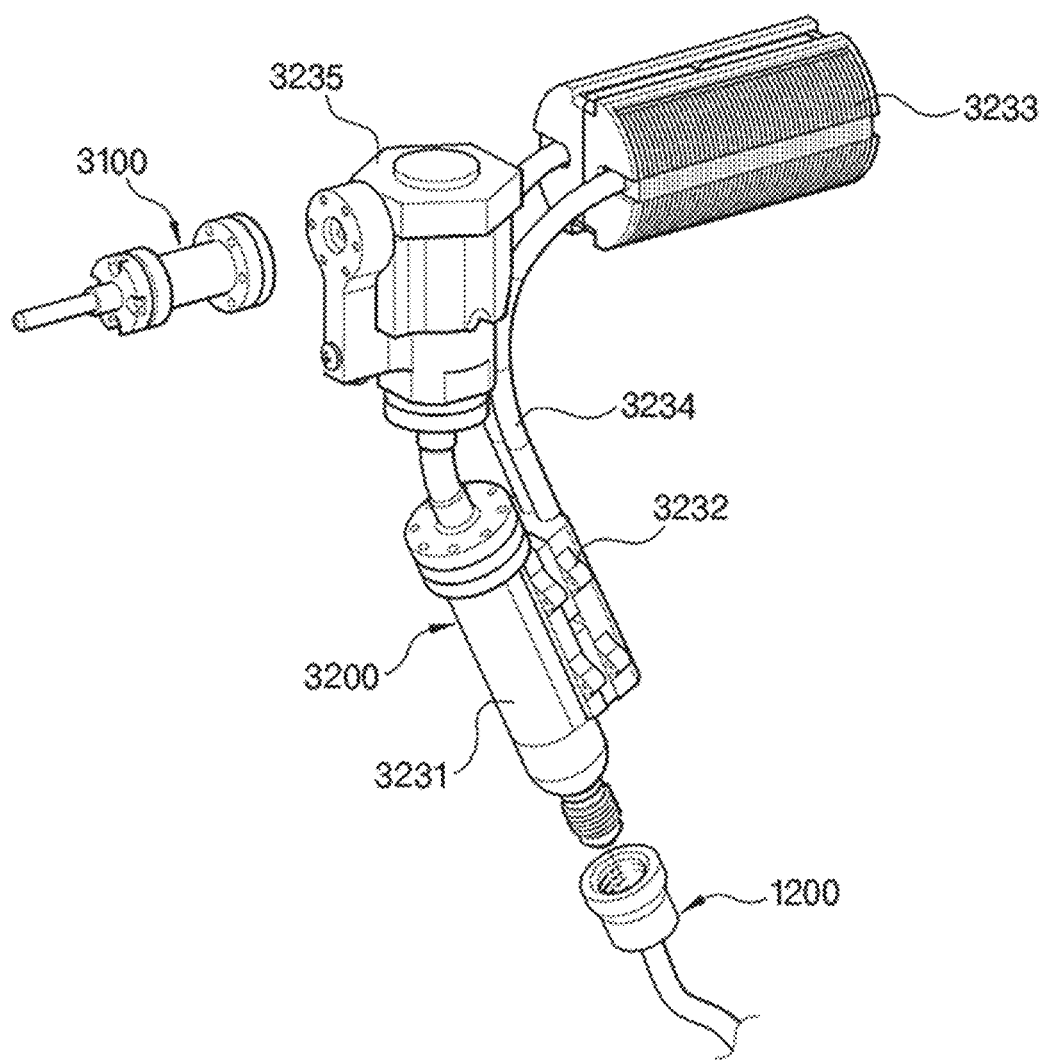
FIGS. 32 and 33 are views for describing a cryogen pressure keeper of the cooling device according to an embodiment of the present application.
Figure 33:
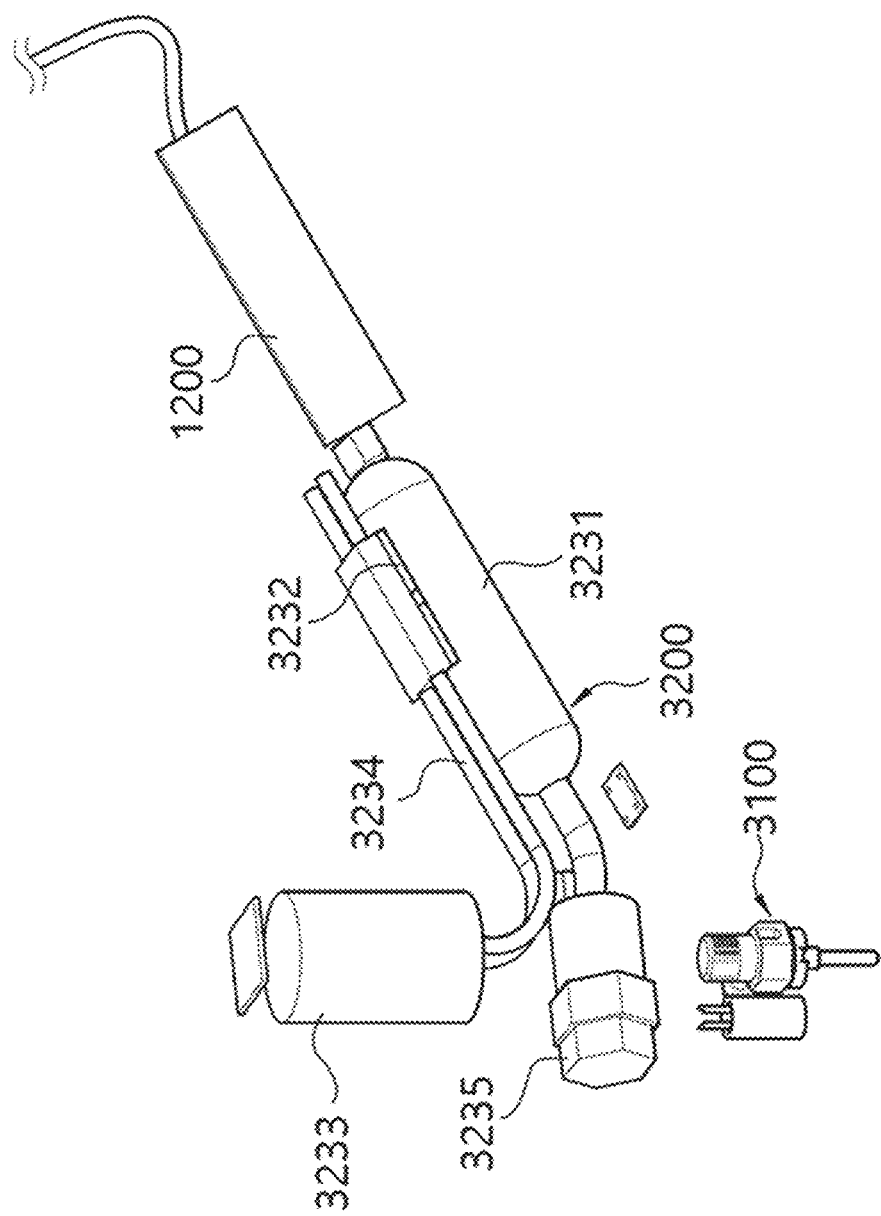

FIGS. 32 and 33 are views for describing the cryogen pressure keeper 3200 of the cooling device 10000 according to an embodiment of the present application.

In cooling a target region TR through a cryogen, using a medical cooling device according to the described technology, the cryogen flows into a tube, which transfers the cryogen to the cooling device, and the cryogen temperature pressure controller 3100 of the cooling device 10000 from a tank storing the cryogen, and the cryogen is sprayed with a predetermined temperature and pressure.

Here, due to a transfer path of the transfer unit 1200 and the cryogen temperature pressure controller 3100, the cryogen makes thermal-mechanical contact with the transfer unit 1200 while moving, and thus loss of temperature and pressure occurs. Also, a response time of spraying of a cryogen according to the button control may be delayed. The described technology includes the cryogen pressure keeper 3200 disposed adjacent to an input end of the cryogen temperature pressure controller 3100 so that, regardless of loss that occurs in a tube connecting the transfer unit 1200 and the tank, the cryogen is stably supplied to the nozzle unit 4100 at a predetermined temperature or pressure, and the cryogen is sprayed while minimizing the time taken for the cryogen to reach a normal state at the predetermined temperature. Such a fast normal-state-reaching time is the key performance in the above-described dynamic cooling control. Also, according to an embodiment, in a case in which the transfer path is long, a plurality of cryogen pressure keepers 3200 may be configured corresponding to the transfer path.

As described above, the dynamic temperature control unit according to the described technology may control a temperature of a cryogen corresponding to a path. According to an embodiment, temperature control of a cryogen is possible through heating or cooling by selective or non-selective association between the tank in which the cryogen is stored, the tube connecting the tank and the cooling device 10000, and each element of the cooling device 1000.

According to an embodiment, precise temperature control of the cryogen may be performed through cooling of the cryogen pressure keeper 3200, heating of the cryogen temperature pressure controller 3100, or cooling or heating of the heat providing barrier 4220. Hereinafter, a configuration of the cryogen pressure keeper 3020 will be described with reference to FIG. 32.

Referring to FIG. 32, the cryogen pressure keeper 3200 is disposed between a tube, which connects a tank formed of a hose or the like and the cooling device 10000, and the cryogen temperature pressure controller 3100 which sprays the cryogen at a predetermined temperature and pressure. The cryogen pressure keeper 3200 performs a function of keeping the pressure of the cryogen to a predetermined pressure or higher even when a certain amount of cryogen exits when the cryogen is supplied to the nozzle unit 4100 so that, when the cryogen is sprayed, the cryogen is sprayed after rapidly reaching a predetermined condition.

According to an embodiment of the described technology, the cryogen pressure keeper 3200 may store, in terms of mass, a larger amount of cryogen than the cryogen sprayed from the nozzle unit 4100. As an example, the cryogen pressure keeper 3200 may store a cryogen having a mass that is twice or more of a mass of the cryogen sprayed from the nozzle unit 4100 per second. As a more specific example, the cryogen pressure keeper 3200 may store a cryogen having a mass that is five times or more of a mass of the cryogen sprayed from the nozzle unit 4100 per second. Also, the cryogen pressure keeper 3200 may keep the stored cryogen in a liquid phase, thereby keeping a significantly larger mass of cryogen in the same volume and keeping the pressure of the cryogen when the cryogen is consumed in the nozzle unit 4100.

According to an embodiment, the cryogen pressure keeper 3200 according to the described technology is disposed at a proximal end of the cryogen temperature pressure controller 3100, i.e., a cryogen inflow side thereof, and the cryogen temperature pressure controller 3100 and the cryogen pressure keeper 3200 are coupled through a coupling unit including a cryogen transfer path. The coupling unit may include a high-pressure valve and the operation of the high-pressure valve may be controlled manually or automatically. Here, in order to insulate the cryogen pressure keeper 3200 and the cryogen temperature pressure controller 3100 from a surrounding cryogen transfer path, the cryogen pressure keeper 3200 and the cryogen temperature pressure controller 3100 may be coupled to the remaining cryogen transfer path through a material whose thermal conductivity is 20 W/m-K or lower, more specifically, a material whose thermal conductivity is 1 W/m-K or lower.

According to an embodiment, the flow-rate of cryogen may be controlled so that a predetermined cooling condition is reached according to control of the control unit 5000. In this case, a valve of the coupling unit may regulate the flow-rate of cryogen through rotation of a needle valve or the like or through a motorized actuator, a flow path that guides the cryogen, which flowed in through the cryogen pressure keeper 3200, to the cryogen temperature pressure controller 3100 may be disposed inside the body unit, and the control unit 5000 that controls the spraying of the cryogen and the temperature of the cryogen may be embedded as an electronic circuit such as a printed circuit board (PCB).

In an embodiment, the high-pressure valve may be configured as a solenoid valve that performs an on-off function. Here, the flow-rate of cryogen may be controlled to a predetermined flow by controlling a time at which the solenoid valve is opened periodically.

According to an embodiment, as described above, in order to keep a larger mass of cryogen per unit volume, the cryogen pressure keeper 3200 may keep a temperature of the cryogen at a temperature lower than or equal to a temperature of the tank and keep the stored cryogen in a liquid phase. According to an embodiment, since the cryogen pressure keeper 3200 keeps the stored cryogen in a predetermined thermodynamic state and keeps the pressure of the cryogen while the cryogen is sprayed, the cryogen sprayed from the cryogen temperature pressure controller 3100 may reach the predetermined thermodynamic state within five seconds. According to another embodiment, the cryogen sprayed from the cryogen temperature pressure controller 3100 may reach the thermodynamic state within one second. Here, the thermodynamic state of the sprayed cryogen may include at least one of a solid phase or a liquid phase.

Referring to FIG. 32, the cryogen pressure keeper 3200 includes a cryogen reservoir 3231 configured to store a cryogen, a cooling generator 3232 configured to cool the cryogen reservoir 3231, a heat dissipater 3233 configured to dissipate heat generated from the cooling generator 3232, and a heat pipe 3234 configured to thermally couple the cooling generator 3232 and the heat dissipater 3233. The cryogen stored in the cryogen reservoir 3231 is cooled by a thermoelectric element, which is the cooling generator 3232 disposed at one side of the cryogen pressure keeper 3200, and is present in a liquid phase or a state in which a liquid phase and a gas phase are mixed. Preferably, by cooling through the control unit and the cooling generator 3232, the cryogen present in the reservoir 3231 is kept as a liquid-phase cryogen in a thermodynamic state. Here, the cryogen pressure keeper 3200 may include a siphon structure to prevent a back flow of the liquid-phase cryogen present in the reservoir 3231 to the cryogen transfer unit 1200.

According to an embodiment, the cryogen pressure keeper 3200 may be disposed within a distance less than or equal to 30 cm from the cryogen temperature pressure controller 3100, and, in order to keep the thermodynamic phase of the cryogen stored therein constant, the cryogen pressure keeper 3200 may be formed of a material having thermal conductivity of 10 W/m-K or higher. Also, the cryogen pressure keeper 3200 may be insulated using an insulating member formed of a material whose thermal conductivity is 10 W/m-K or lower so that an influence from the outside is minimized.

Also, in order to make the cryogen pressure keeper 3200 and the cryogen temperature pressure controller 3100 thermally independent, in a flow path in which the cryogen pressure keeper 3200 and the cryogen temperature pressure controller 3100 are connected, the thermal conductivity of at least one element may be 10 W/K or lower. According to an embodiment, the cryogen pressure keeper 3200 may also be provided as a plurality of cryogen pressure keepers 3200 according to a flow path in which a cryogen selectively flows.

According to the described technology, a cryogen is supplied to the cryogen temperature pressure controller 3100 through a valve which controls the opening and closing of the cryogen pressure keeper 3200 or the flow-rate of the cryogen. Here, according to a preferred embodiment of the described technology, a solenoid valve 2100 which is electrically connected to the control unit 5000 and whose opening and closing are controlled by control of the control unit is embedded. The solenoid valve 2100 selectively opens or closes the flow path through which the cryogen flows by control of the control unit 5000.

Here, preferably, the solenoid valve 2100 is disposed on the flow path between the cryogen temperature pressure controller 3100 and the cryogen pressure keeper 3200 so that the pressure of the cryogen, which has a high pressure, is continuously kept.

Therefore, the solenoid valve 2100 is electrically connected to the control unit 5000 and the spraying button, a signal generated as the user operates the spraying button is input to the control unit 5000, and the control unit controls the opening of the solenoid valve 2100 on the basis of the input signal so that the cryogen is sprayed. In still another embodiment, the solenoid valve 2100 may automatically perform a plurality of opening and closing operations according to a predetermined protocol from the control unit 5000 and thus may be open only for a predetermined amount of time during a treatment time. For example, the control unit 5000 may partially open the solenoid valve 2100 periodically using a pulsed width modulation (PWM) technique. More specifically, the control unit 5000 may open the solenoid valve 2100 only during 50% time at a frequency of 3 Hz.

FIG. 33 is a view illustrating a cooling structure that the cryogen pressure keeper 3200 has when the cryogen pressure keeper 320 additionally serves as a cryogen temperature pressure keeper that keeps a thermodynamic phase through the cooling supplied from the cooling generator 3232 according to an embodiment of the present application. In addition, it is self-evident that the cryogen temperature pressure keeper, which is an embodiment derived from the cryogen pressure keeper 3200, is differentiated from the cryogen temperature pressure controller 3100 which performs prompt dynamic control on the thermodynamic phase of the cryogen.

Referring to FIG. 33, the cryogen temperature pressure keeper according to the described technology is kept cool by the cooling generator 3232 thermally coupled thereto. A configuration of the cooling generator 3232 may have any form as long as cooling energy can be supplied to the cryogen pressure keeper 3230. In a case in which the cooling generator 3232 uses a thermoelectric element, when current is applied to the thermoelectric element, due to the Peltier effect, an endothermic reaction may occur on a side of the thermoelectric element coming into contact with the cryogen temperature pressure keeper, and an exothermic reaction may occur on a side of the thermoelectric element coming into contact with the heat dissipater 3233. In this way, cooling heat in a region where the cooling generator 3232 and a subject come into contact may be transferred to a cryogen, which is being sprayed, through the cooling generator 3232 and the cryogen temperature pressure keeper, and heat generated in the cooling generator 3232 may be dissipated to the outside via the heat dissipater 3233 which will be described below.

The heat dissipater 3233 may discharge heat generated from the cooling generator 3232 to the outside. The heat dissipater 3233 may also be referred to as "heat sink," "heat discharger," "heat emitter," "heat spreader," or the like. The heat dissipater 3233 may be formed of a thermally-conductive material to efficiently discharge heat generated in the process in which the cooling generator 3232 generates cooling energy. For heat dissipation efficiency, the heat dissipater 3233 may be formed of two or more heat dissipating units which are coupled. Here, a fan may be disposed between the heat dissipating units.

The heat dissipater 3233 and the cooling generator 3232 may be disposed to be spaced apart through a heat transfer medium and keep the cryogen pressure keeper cool. In order to allow an air flow formed from a cooling fan to pass between heat dissipation fins, a suction port and a discharge port may be formed in the heat dissipater 3233 according to the described technology. As another embodiment, suction ports and discharge ports corresponding to the number of cooling fins may be formed in the heat dissipater 3233. In other words, a plurality of suction ports and discharge ports which are perforated in a direction not parallel to an axial direction of the body unit may be formed in the heat dissipater 3233. By action of the cooling fins, air may be suctioned through the suction port of the heat dissipater 3233 and discharged through the discharge port of the heat dissipater 3233. Here, positions of the plurality of suction ports and the plurality of discharge ports may correspond so that the plurality of suction ports and the plurality of discharge ports overlap each other, and a cooling fin may be disposed between each pair of the suction port and the discharge port. In this way, since an air flow formed from the cooling fin may be formed through each pair of the suction port and the discharge port, the heat transfer between the heat dissipater 3233 and the air may be maximized.

The heat pipe 3234 according to the described technology serves to mediate the heat transfer between the cooling generator 3232 and the heat dissipater 3233. The heat transfer medium, which includes the heat pipe 3234 and the like, performs a function of connecting the cooling generator 3232 and the heat dissipater 3233 and transferring heat from the cooling generator 3232 to the heat dissipater 3233 while allowing the heat dissipater, which includes a cooling fan and the like, to be spaced apart, thereby allowing the body unit to be configured in consideration of user convenience. That is, the body unit according to the described technology has a structure formed of a plurality of body units. The cryogen pressure keeper 3200 may be disposed in a first body unit, and the heat dissipater 3234 may be configured in a second body unit. In this way, convenience of operation and heat dissipation efficiency of cooling fans may be improved.

Here, the heat transfer medium according to the described technology may be the heat pipe 3234 or a vapor chamber and may include a pipe main body and a phase change material disposed inside the pipe main body. The pipe main body of the heat transfer medium may be formed of a material having high thermal conductivity in order to effectively transfer the heat generated from the cooling generator to the phase change material inside the pipe main body by coming into contact with the cooling generator 3232. Here, the phase change material is a material that stores a large amount of thermal energy or releases the stored thermal energy through a phase change process. The phase change material has an intrinsic ability to store heat.

Also, since, in the medical cooling device, the heat dissipater 3233 and the cooling fin are disposed at a rear end of the body unit that is spaced apart from a treatment site which is at a distal end from which the cryogen is sprayed, the effect of air flow that may occur at the treatment site may be minimized so that the risk of injection or the like is reduced. In this way, since the heat dissipater 3233 is disposed to be spaced apart from the cryogen temperature pressure keeper instead of being disposed to be adjacent thereto, the cooling device according to the present embodiment may provide a structure that can be gripped by the user to improve an ease of operation by the user and may also be implemented in various other structures not described herein for efficiency of the performance.

FIGS. 34 to 38 are views illustrating configurations of the temperature pressure controller 3100 according to an embodiment of the present application. In the described technology, the thermodynamic phase (temperature, pressure) of the cryogen may be controlled corresponding to a path through which the cryogen moves. The control of the thermodynamic phase of the cryogen is possible through heating or cooling by selective or non-selective association with each element of the cooling device. According to an embodiment, the case in which the thermodynamic phase of the cryogen is controlled using thermal energy will be mainly described, but the pressure of the cryogen may be controlled using other types of energy, e.g., mechanical energy. According to another embodiment, the cooling control on the cryogen pressure keeper 3200 and the heating control on the cryogen temperature pressure controller 3100 will be mainly described, but the present application is not limited thereto, and temperature control on the elements may be performed in various other ways. For example, when the medical cooling device is used for killing cells such as during cancer treatment, the cryogen temperature pressure controller 3100 may also receive cooling control.

Figure 34:
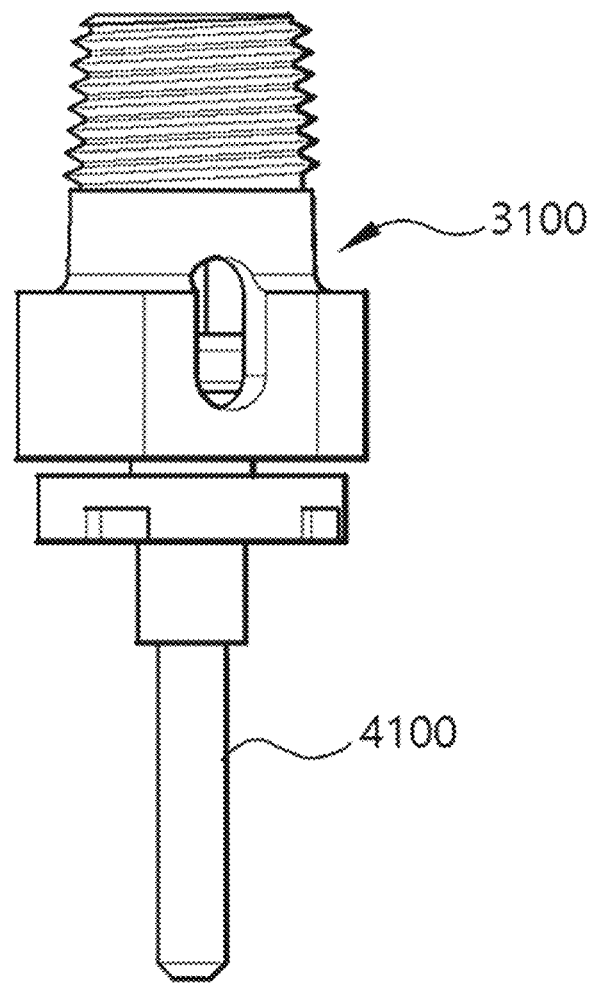
FIGS. 34, 35, 36, 37 and 38 are views illustrating configurations of a temperature pressure controller according to an embodiment of the present application.
Figure 35:
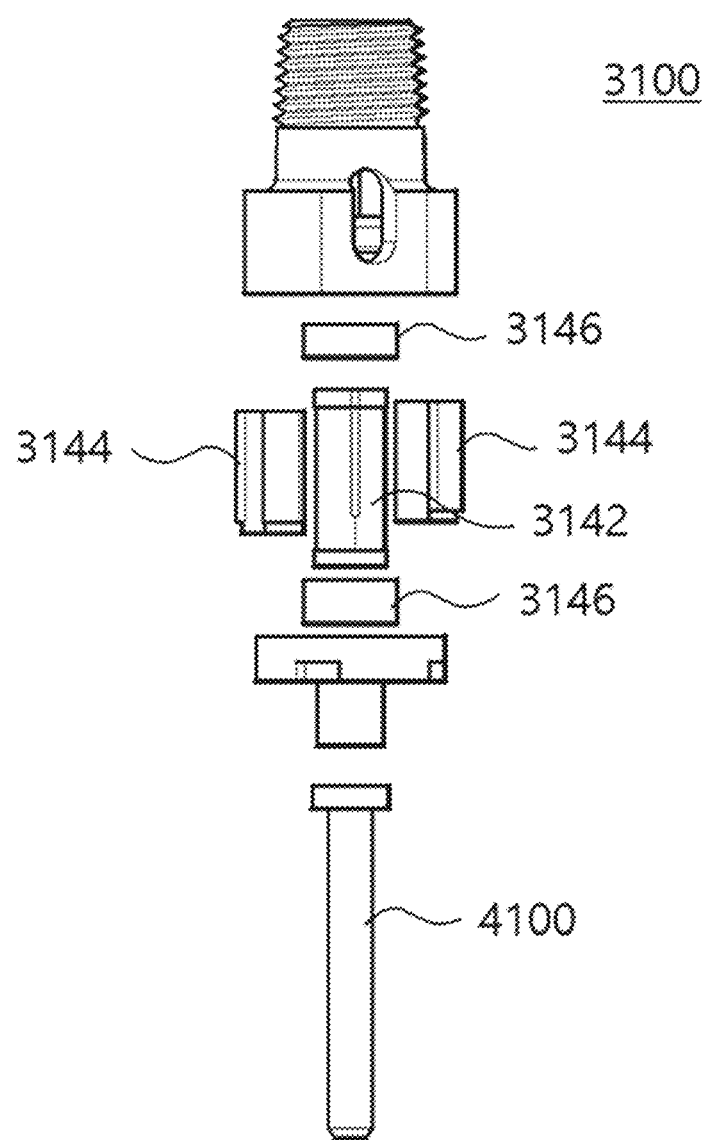
Figure 36:
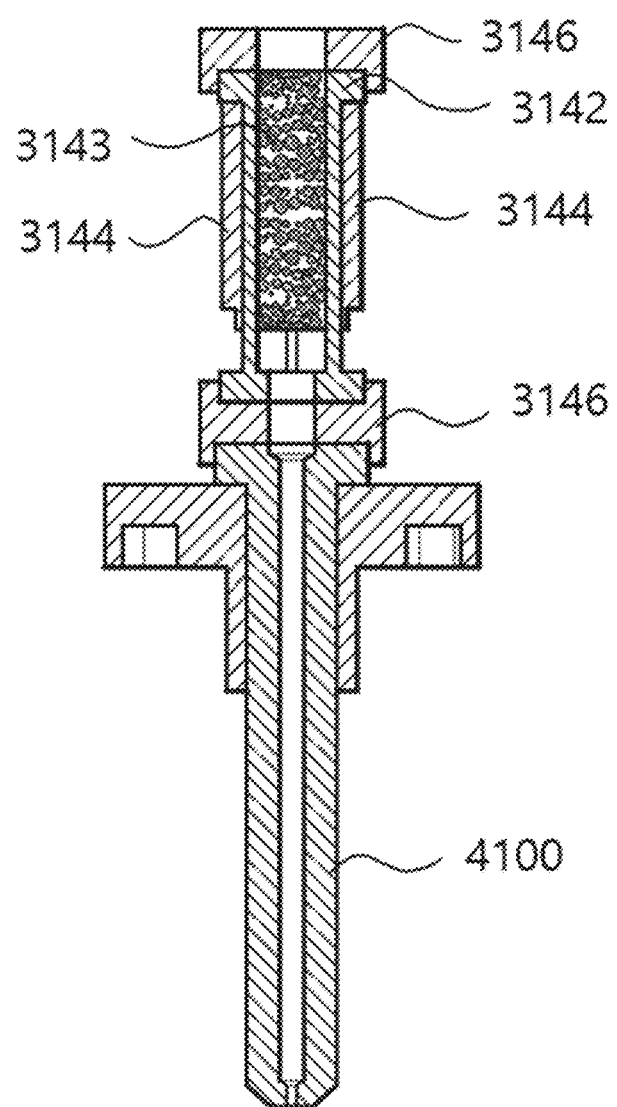

FIG. 34 is a view illustrating a configuration of the cryogen temperature pressure controller 310 according to an embodiment of the present application. FIG. 35 is an exploded view of the cryogen temperature pressure controller 3100 according to a preferred embodiment of the described technology, and FIG. 36 is a view illustrating a see-through view of the cryogen temperature pressure controller 3100 according to a preferred embodiment of the described technology.

According to an embodiment, the cryogen temperature pressure controller 3100 according to the described technology is formed of a heat transfer medium structure between the cryogen and the thermoelectric element on the basis of thermoelectric element-based heating control. Also, the cryogen temperature pressure controller 3100 includes a nozzle structure in which the amount of cryogen sprayed and the Joule-Thomson effect may be optimized.

Referring to FIG. 34, the cryogen temperature pressure controller 3100 of the medical cooling device according to the described technology may control spraying of the cryogen, which is being sprayed to a site subject to treatment, at a predetermined pressure or temperature. The configuration of the cryogen temperature pressure controller 3100 includes a barrel unit which allows the cryogen to flow in and move to the nozzle unit 4100 and the nozzle unit 4100 which sprays the cryogen which flowed in from the barrel unit.

According to a preferred embodiment of the described technology, at one side of the barrel unit, in which a flow path through which the cryogen flows is formed, through which the cryogen flows into the nozzle unit 4100, a heat transfer medium 3142 for, prior to spraying of the cryogen, pre-treating the cryogen with heat through thermal contact with the cryogen inside the barrel unit may be further provided.

In the nozzle unit 4100, a nozzle with a narrower width than the flow path of the barrel unit through which a high-pressure cryogen flows is formed. As the flow path is opened, the high-pressure cryogen is guided to the nozzle along the flow path, and the cryogen discharged through the nozzle is sprayed in a cooled state through the nozzle due to the Joule-Thomson effect.

Here, the Joule-Thomson effect refers to a phenomenon in which temperature drops when a compressed gas expands. The Joule-Thomson effect refers to a phenomenon in which temperature changes in relation to a thermodynamic phase which consists of the pressure and temperature and is a phenomenon applied when liquefying the air or cooling using a refrigerant. The Joule-Thomson effect is a phenomenon in which, in a case in which an aperture such as an orifice is inserted into a flow path of a fluid, the temperature of the fluid drops at a rear portion of the aperture. The Joule-Thomson effect refers to a phenomenon with which, when a gas freely expands, i.e., when the gas goes through adiabatic expansion without any exchange with the outside, internal energy of the gas almost does not change. The Joule-Thomson effect refers to an effect in which free adiabatic expansion of a gas is performed to obtain a low temperature using a gas liquefying device.

Due to the Joule-Thomson effect, the pressure of the cryogen which is sprayed through the nozzle rapidly changes and the cryogen is cooled. When the cryogen is sprayed to a site subject to treatment, as the cryogen comes into contact with the site subject to treatment and take away heat from the site subject to treatment, the site subject to treatment is cooled.

Here, precise temperature control of the sprayed cryogen is performed by the cryogen temperature pressure controller 3100 included in the nozzle unit 4100. Hereinafter, the cryogen temperature pressure controller 3100 will be mainly described. Temperature control of cryogen through the heat transfer medium 3143 of the cryogen temperature pressure controller 3100 will be described in detail below with reference to the drawings.

The cryogen sprayed from the cryogen temperature pressure controller 3100 which controls the temperature and pressure of the cryogen is sprayed to the outside of the cooling device, i.e., to the target region, through the nozzle unit 4100 and cools the target region to a desired temperature.

The cryogen temperature pressure controller 3100 according to the described technology provides heat to the cryogen prior to spraying of the cryogen and allows precise temperature control of the cryogen. According to an embodiment, by increasing the spraying temperature of the cryogen through the above configuration, the cryogen temperature pressure controller 3100 may prevent cells of the site subject to treatment from dying due to supercooling or control the cooling temperature of the site subject to treatment within a temperature range suitable for a desired therapeutic effect.

Conventionally, cryotherapy or cold therapy using liquid nitrogen is mostly used. However, since a cooling condition is not controlled, there is a side effect in that, when killing cells in lesions, a large amount of normal cells around the cells in lesions are destructed. The cooling treatment according to the described technology is aimed at killing cells including vascular cells at a temperature lower than or equal to −40° C. (or −25° C. vary according to cells). At temperatures in a range of −40° C. (or −25° C., vary according to cells) to 0° C., apoptosis or an immune activation effect may be aimed at. The described technology has an effect in that, through the above-described cryogen temperature pressure controller 3100, the cryogen can be sprayed corresponding to an optimal temperature according to the target region TR, the treatment site, or the treatment purpose or sprayed at an optimal cooling speed, an optimal thawing speed, and at a plurality of temperatures.

Referring to FIG. 36, more closely looking at the configuration of the cryogen temperature pressure controller 3100 according to the described technology, the cryogen temperature pressure controller 3100 includes a hollow barrel formed therein and a holder unit 3142, which has a contact surface for coming into contact with a heat generator 3144, formed at an outer circumferential surface, and, as the heat generator 3144 is thermally coupled to an outer circumferential surface of the holder unit 3142, the cryogen temperature pressure controller 3100 performs a function of supplying heat to the cryogen flowing in the barrel unit of the cryogen temperature pressure controller 3100.

According to a preferred embodiment of the described technology, the heat transfer medium 3143 for efficiently performing heat transfer of the cryogen may be accommodated in one side of the barrel, i.e., the hollow, of the holder unit 3142. According to an embodiment, the heat transfer medium 3143 may be formed of a material whose thermal conductivity is 10 W/m-K or higher and is formed at an inflow unit of the nozzle unit 4100 in the barrel through which the cryogen flows. According to an embodiment, in order to efficiently transfer heat to the cryogen, the heat transfer medium 3143 has a structure capable of increasing a contact area with the cryogen. For example, the heat transfer medium 3143 may be formed of a porous material. For example, the heat transfer medium 3143 may be formed of a porous material which is formed by sintering metal particles having high thermal conductivity.

The heat generator 3144, the holder unit 3142, and the heat transfer medium 3143 are thermally coupled, and heat exchange occurs through thermal contact between the cryogen and a plurality of heat transfer media 3143 provided in the flow path. Therefore, the cryogen flows into the nozzle through the hollow of the holder unit 3142, and the cryogen which flowed into the nozzle is sprayed as it discharges to the outside. When the cryogen flows into the hollow of the barrel, the thermodynamic phase, i.e., the temperature and pressure, of the cryogen may be controlled or increased through thermal contact with the heat transfer medium 3143 formed in the flow path.

The function of the cryogen temperature pressure controller 3100 controlling the pressure as well as the temperature of the cryogen may allow the cryogen temperature pressure controller 3100 to serve as a thermodynamic active valve which restricts the flow of cryogen by a pressure due to energy applied to the cryogen temperature pressure controller 3100. In this way, the cryogen temperature pressure controller 3100 may reduce the cryogen flow-rate itself in addition to decreasing the temperature of the cryogen.

According to an embodiment, the heat generator 3144 may be formed of a thermoelectric element and transfer the heat generated from the heat generator 3144 in a selective direction, i.e., in a direction toward the holder unit 3142. Here, when power is supplied to the heat generator 3144 by control of the control unit, the heat generator 3144 may generate heat by the power. The heat generated by the heat generator 3144 is conducted to the holder unit 3142, and, as the heat conducted to the holder unit 3142 is conducted to the heat transfer medium 3143 embedded inside the holder unit 3142, the cryogen flowing along the flow path of the heat transfer medium 3143 receives heat and is heated.

Figure 37:
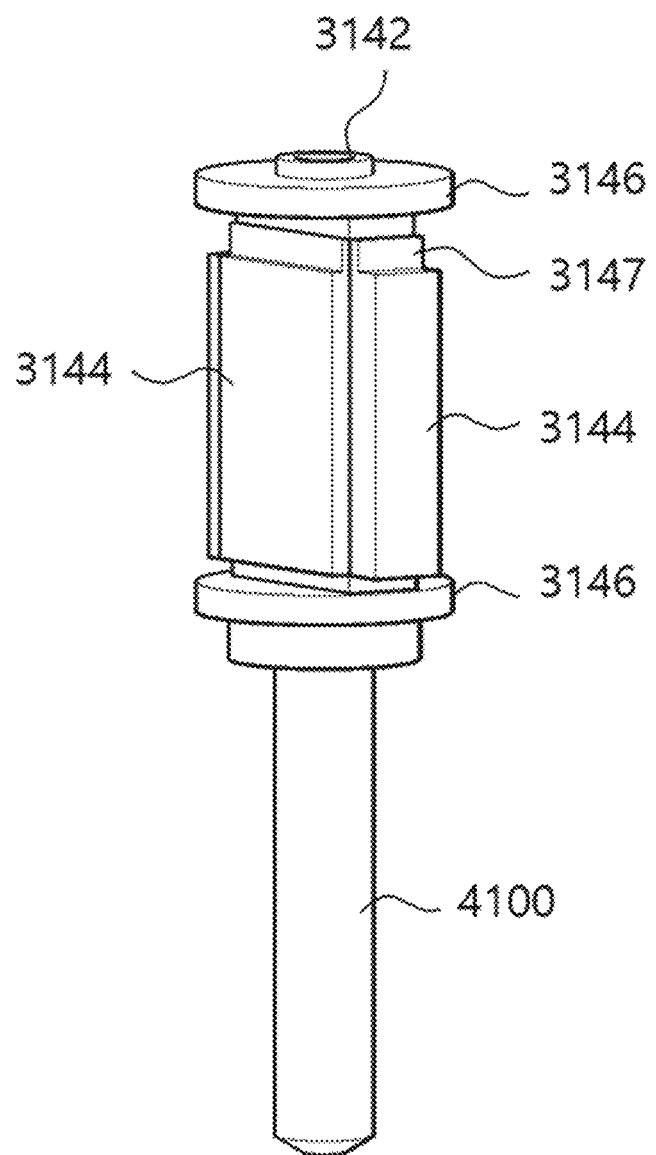
Figure 38:
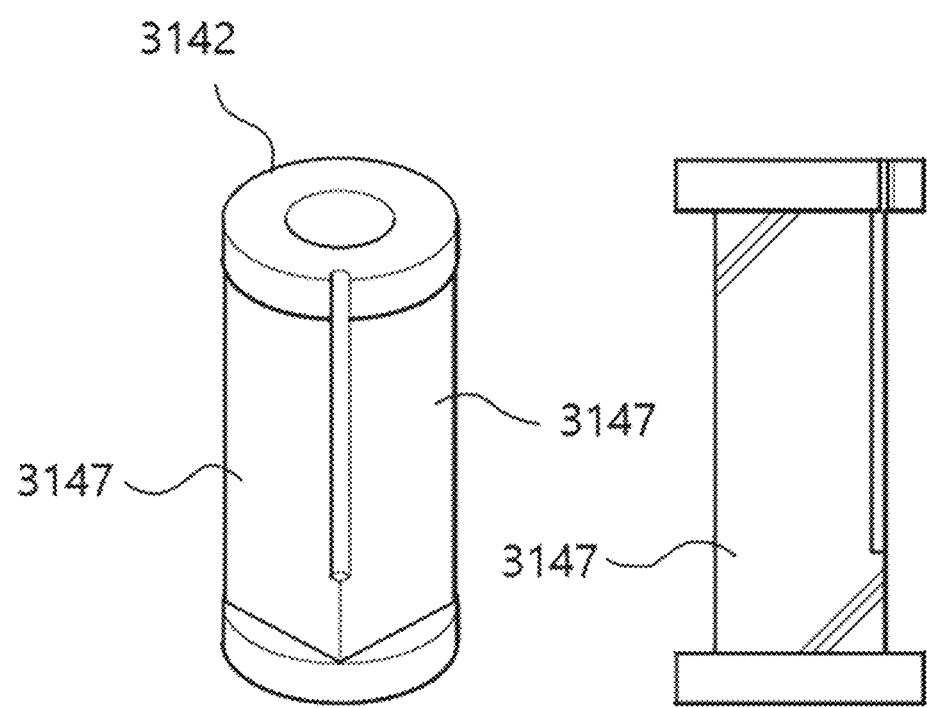

FIG. 37 is a view illustrating a mounting structure of the heat generator 3144 according to an embodiment of the present application, and FIG. 38 is a view illustrating a configuration of the holder unit 3142 according to an embodiment of the present application.

According to an embodiment, the holder unit 3142 has a tubular form in which a hollow, through which a cryogen flows, is formed. The outer circumferential surface of the holder unit 3142 serves as a binding fixing surface 3147 to which the heat generator 3144 is bound and fixed. Here, the binding fixing surface 3147 may be provided as a plurality of binding fixing surfaces 3147 disposed radially or symmetrically about the central axis of the holder unit 3142. For example, as illustrated in FIG. 37, four binding fixing surfaces 3147 may be formed around the hollow of the holder unit 3142, and each of a total of four heat generators 3144 may be bound and fixed to one of the binding fixing surfaces 3147.

Here, in the described technology, only the case in which the four binding fixing surfaces 3147 are formed in the holder unit 3142 will be described, but the described technology is not limited thereto. The number of binding fixing surfaces 3147 may also be changed to various other numbers such as two, three, and five according to a controlled temperature range and a quantity of heat generated by the heat generator 3144.

Here, the heat generator 3144 is preferably formed of a thermoelectric element capable of controlling a heat generation direction using an external power supply. However, the heat generator 3144 may also be formed of a nichrome wire which generates heat using an external power supply.

Here, the heat transfer medium 3143 according to the described technology may form a plurality of fins in a flow path through which the cryogen flows so that a heat transfer area with the cryogen increases. Alternatively, the heat transfer medium 3143 may be formed of a porous structure and increase a heat transfer area with the cryogen. Here, the heat transfer medium 3143 formed of the porous structure simultaneously performs functions of absorbing noise generated when the cryogen flows and decreasing the pressure of the cryogen.

Also, the heat transfer medium 3143 may regulate the flow-rate of the cryogen. According to a length of a section in which the heat transfer medium 3143 is formed and the size or structure of the heat transfer medium 3143, the flow path of the heat transfer medium 3143 becomes narrower than a conventional barrel such that the heat transfer medium 3143 serves to decrease the flow-rate of the cryogen passing through the flow path of the heat transfer medium 3143. In addition, the heat transfer medium 3143 may serve to absorb sound.

That is, when heat is selectively provided to the cryogen by using the heat generator 3144 included in the cryogen temperature pressure controller 3100, the heat transfer medium 3143 may heat the cryogen and regulate the flow-rate of the cryogen so as to control the temperature of the site subject to treatment so that the cells of the site subject to treatment are not frozen and destructed.

Further, the heat transfer medium 3143 according to the described technology may be a heat generating material that generates heat by itself, instead of a heat transfer medium that mediates the heat transfer. In one embodiment, a heat generating material formed of a nichrome w % ire may be installed along an inner surface of a hollow of the holder unit 3142 through which the cryogen flows and may directly provide heat to the cryogen flowing through the hollow of the holder unit 3142.

In addition, the cryogen temperature pressure controller 3100 has a small contact area with surrounding utensils or is insulated from the surrounding utensils through an insulating member 3146 having thermal conductivity of lower than or equal to 10 W/m-K. Here, Teflon may be applied as the insulating member 3146.

The insulating member 3146 may be provided at each of an inflow side and an outflow side of the holder unit 3142, thermally insulated from the nozzle unit 4100 and the transfer unit 1200 to minimize an influence from the outside, and allow the cryogen to be sprayed with fast responsivity under a predetermined condition.

According to a preferred embodiment of the described technology, the cryogen temperature pressure controller 3100 may generate heat for a corresponding designated time after use of the medical cooling device and then remove the cryogen remaining therein.

Figure 39:
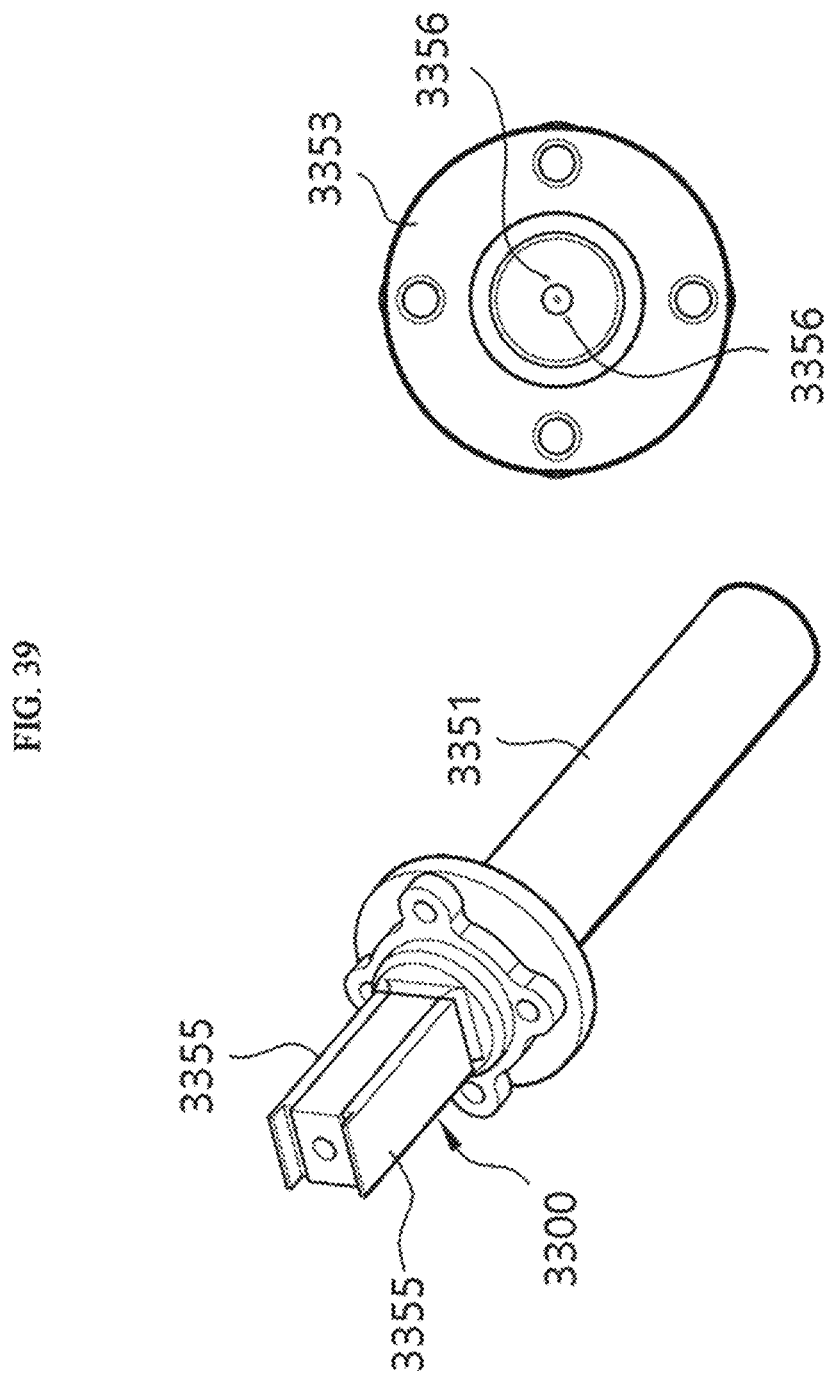
FIGS. 39, 40 and 41 are views for describing configurations of a cryogen cyclone rotator according to an embodiment of the present application.
Figure 40:
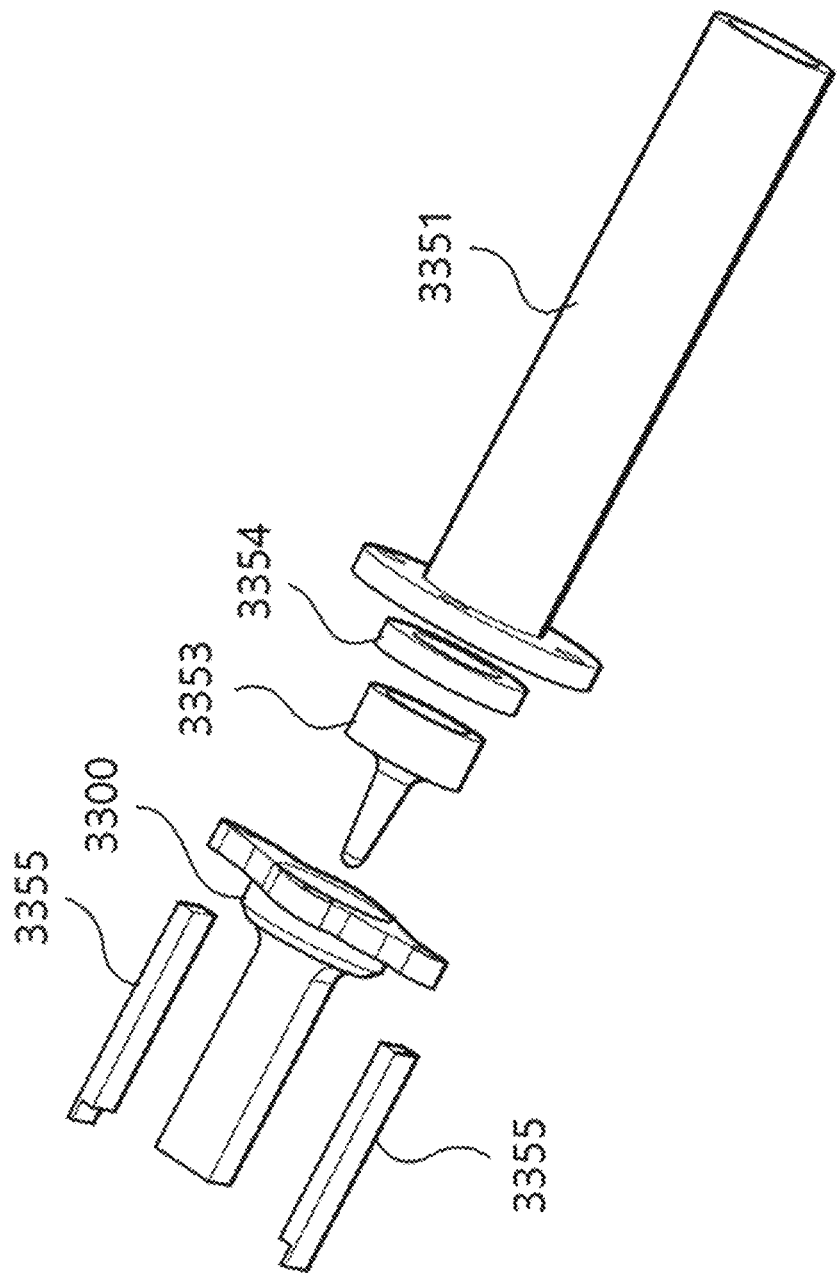
Figure 41:
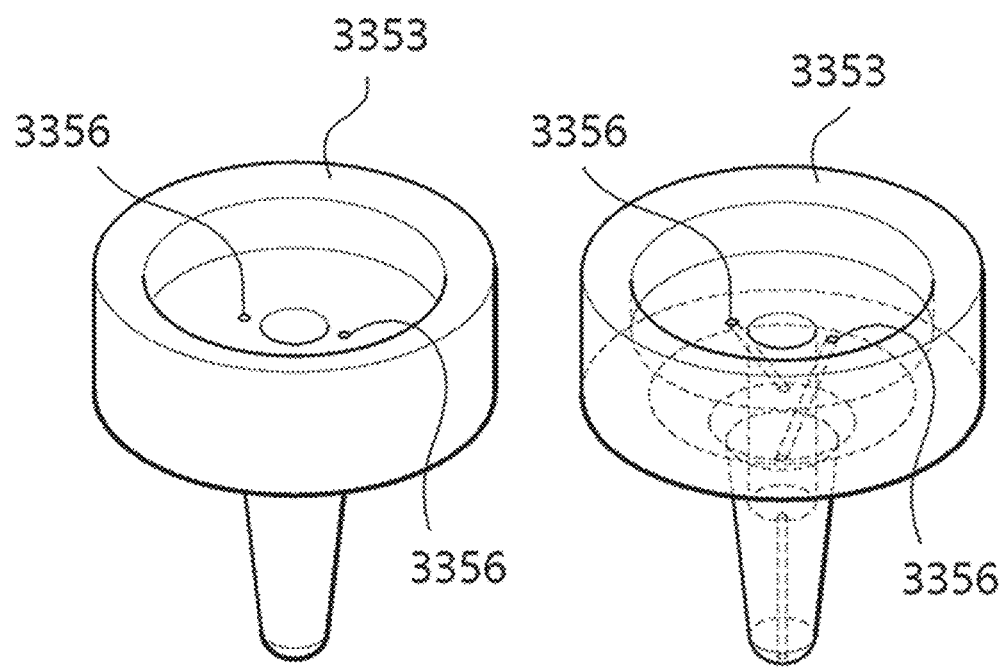

FIGS. 39 to 41 are views for describing configurations of a cryogen cyclone rotator 3300 according to an embodiment of the present application. More specifically, FIGS. 39 and 40 are views illustrating the configuration of the cryogen cyclone rotator 3300, and FIG. 41 is a view illustrating a configuration of a cryogen cyclone generator 3353 according to an embodiment of the present application.

The cooling device 10000 according to an embodiment of the present application includes the cryogen cyclone rotator 3300 which sprays a cryogen diagonally, rotates air and the cryogen through rotation in the form of eddy current, and then allows the cryogen to be sprayed to the outside. The cryogen cyclone rotator 3300 includes the cryogen cyclone generator 3353 as a key component therein. Hereinafter, the configuration of the cryogen cyclone rotator 3300 will be described in detail with reference to the drawings.

FIG. 39 is a view illustrating the configuration of the cryogen cyclone rotator 3300, and FIG. 40 is a view illustrating an exploded view of the cryogen cyclone rotator 3300.

First, referring to FIG. 39, the cooling device 10000 according to an embodiment of the present application, which is a medical cooling device according to the described technology, includes a cryogen inflow unit 3351 through which the cryogen flows in, the cryogen cyclone generator 3353 configured to spray the cryogen, which flowed in through the cryogen inflow unit 3351, in a diagonal direction, and the cryogen cyclone rotator 3300 configured to induce rotation of the cryogen in the form of eddy current. According to an embodiment, the cryogen inflow unit 331 and the cryogen cyclone rotator 3300 or the cryogen cyclone generator 3353 are coupled with a sealing member 3354 such as a gasket.

The cryogen that flowed into the transfer unit 1200 from a tank through a tube and passed through the transfer unit 1200 flows into the cryogen cyclone generator 3353 through the cryogen inflow unit 3351. The cryogen cyclone generator 3353 sprays the flowed-in cryogen diagonally, rotates the air and the cryogen through rotation in the form of eddy current, and then allows the cryogen to be sprayed to the outside.

A fluid in which the air and cryogen spread in the diagonal direction are mixed comes into contact with an inner circumferential surface of the cryogen cyclone rotator 3300 diagonally instead of in a straight line. In this way, the cryogen flow itself may be adjusted, and a substantial contact area may be increased without increasing mass of the heat transfer medium. That is, since, unlike the above-described heat transfer medium configured in the cryogen temperature pressure controller, the contact area with the cryogen is increased without increasing the mass of the heat transfer medium, there is an effect in that it is possible to simultaneously increase the quantity of heat transferred and the thermal response speed. Also, due to a difference in a frictional force that occurs as the cryogen rotates at the inner circumferential surface of the cryogen cyclone rotator 3300 and the cryogen in a gas phase, liquid phase, or solid phase comes into contact with the inner circumferential surface of the cryogen cyclone rotator 3300 due to a centrifugal force, there is an effect in that the spraying speed or the spraying temperature of the cryogen can be selectively and effectively controlled. For example, due to a high frictional force between the solid-phase cryogen and the inner circumferential surface of the cryogen cyclone rotator 3300, the rotating speed may be selectively decreased, a contact time between the cryogen and the inner circumferential surface of the cryogen cyclone rotator 3300 may increase as a result, and the quantity of heat transferred from the inner circumferential surface of the cryogen cyclone rotator 3300 to the solid-phase cryogen may be selectively increased.

While the above-described cryogen control through the heat transfer medium of the cryogen temperature pressure controller may be referred to as "control before spraying the cryogen," the cryogen control using the cryogen cyclone rotator 3300 may be referred to as "control after spraying the cryogen." Here, the heat transfer medium may be disposed to come into contact with the outer circumferential surface of the cryogen cyclone rotator 3300. Through such a configuration, in a state in which the cryogen cyclone rotator 3300 and the heat transfer medium are thermally coupled, the cryogen rotates in the form of eddy current and comes into thermal contact with the inner circumferential surface of the cryogen cyclone rotator so that, even after the cryogen is sprayed through the nozzle, the temperature of the cryogen may be controlled through the heat transfer between the cryogen cyclone rotator and the cryogen.

Referring to FIG. 39, a cross-sectional view of the cryogen cyclone rotator 3300 is illustrated. The cryogen cyclone generator 3353 is provided inside the cryogen cyclone rotator 3300. According to an embodiment, the cryogen cyclone generator 3353 has a circular outer shape, but of course the cryogen cyclone generator 3353 may be implemented in other shapes. The cryogen cyclone generator 3353 includes one or more diagonally-formed flow paths 3356. Preferably, the diagonally-formed flow paths 3356 may be formed radially or symmetrically about the central axis of the cryogen cyclone generator 3353.

The cryogen sprayed by the diagonally-formed flow paths 3356 leaks in the diagonal direction through the diagonally-formed flow paths 3356 and is cooled and sprayed due to the Joule-Thomson phenomenon at the same time. The cryogen flows diagonally, moves in the form of eddy current through collision with the inner circumferential surface of the cryogen cyclone rotator 3300, is jetted to the outside, and reaches the target region TR at a reduced spraying speed and temperature.

Referring to FIG. 40, the outer circumferential surface of the cryogen cyclone rotator 3300 is configured to come into contact with a thermoelectric element 3355. According to a preferred embodiment of the described technology, the outer circumferential surface of the cryogen cyclone rotator 3300, i.e., a contact surface with the thermoelectric element 3355, may be formed as a flat surface for contact with the thermoelectric element 3355 or efficiency of heat transfer. Here, the outer circumferential surface may be provided as a plurality of outer circumferential surfaces disposed radially or symmetrically about the central axis of the cryogen cyclone rotator 3300. As illustrated in FIG. 37, four outer circumferential surfaces may be formed, and each of a total of four thermoelectric elements 3355 may be bound and fixed to one of the outer circumferential surfaces. Here, in the described technology, only the case in which the four outer circumferential surfaces are formed will be described, but the described technology is not limited thereto. The number of outer circumferential surfaces may also be changed to various other numbers such as two, three, and five according to a controlled temperature range, a target region, a treatment site, or a treatment purpose.

Here, the length of the cryogen cyclone rotator 3300 may also be changed according to a controlled temperature range, a target region, a treatment site, or a treatment purpose. As described above, since it is possible to reduce the speed of the cryogen and control the temperature of the cryogen through the movement of cryogen sprayed in the diagonal direction, according to an embodiment, the inner circumferential surface of the cryogen cyclone rotator 3300 is preferably configured to have a sufficient length so that cryogen speed control or cryogen temperature control is possible.

According to an embodiment of the described technology, a coupling unit between the cryogen inflow unit 3351 and the cryogen cyclone generator 3353 may be formed of the sealing member 3354 such as a gasket. In this way, while improving the sealing performance, the sealing member 3354 may be formed of a material such as Teflon and effectively block the heat transfer.

FIG. 41 is a view illustrating a configuration of the cryogen cyclone generator 3353 according to a preferred embodiment of the described technology.

The cryogen cyclone generator 3353 according to the described technology allows the cryogen to flow in the form of eddy current. In cooling the target region TR using the cryogen, the cryogen sprayed in the diagonal direction rotates due to the cryogen cyclone rotator 3300, which induces rotation of the cryogen in the form of eddy current, and then is sprayed to a treatment region.

Here, for the rotation, the cryogen cyclone generator 3353, in which a first diagonally-formed flow path 3356 is formed, is required to spray the cryogen in the diagonal direction. Referring to FIG. 41, a perspective view and a see-through view of the cryogen cyclone generator are illustrated.

In order to spray the cryogen in the diagonal direction, the cryogen cyclone generator 3353 may further include a second diagonally-formed flow path 3356. Here, in a case in which the plurality of diagonally-formed flow paths 3356 are formed in the cryogen cyclone generator 3353, preferably, the diagonally-formed flow paths 3356 are disposed to be symmetrical and spray the cryogen in opposite directions so that the eddy current of cryogen is symmetrically and stably generated.

According to a preferred embodiment of the described technology, the cryogen cyclone generator 3353 may further include a flow path which causes perpendicular incidence of a cryogen and be configured to more precisely control the spraying speed by associating spraying in the diagonal direction and spraying in a forward direction.

The cryogen cyclone rotator 3300 controls the temperature of the cryogen through contact with the cryogen being sprayed. Since a trajectory of a fluid increases due to the incidence of the cryogen in the diagonal direction, the contact surface and contact time between the cryogen and the cryogen cyclone rotator 3300 may increase as compared with when the cryogen is incident perpendicularly. Also, due to the increased contact area and contact time between the cryogen and the cryogen cyclone rotator 3300, the heat transfer between the cryogen and the cryogen cyclone rotator 3300 may be increased.

Also, in the cryogen sprayed in a plurality of phases including at least two of gas, liquid, and solid phases, relatively more contact or friction may occur between the cryogen cyclone rotator 3300 and the cryogen present in the liquid or solid phase. That is, the cryogen present in the liquid or solid phase may rotate in a slower rotation speed than the cryogen present in the gas phase, and a relatively larger quantity of heat may be transferred to the cryogen present in the solid or liquid phase that rotates relatively slowly.

FIGS. 42 to 45 are views for describing configurations of the heat providing barrier 4220 according to an embodiment of the present application. Hereinafter, the configuration of the heat providing barrier 4220 will be described in detail with reference to the drawings.

Figure 42:
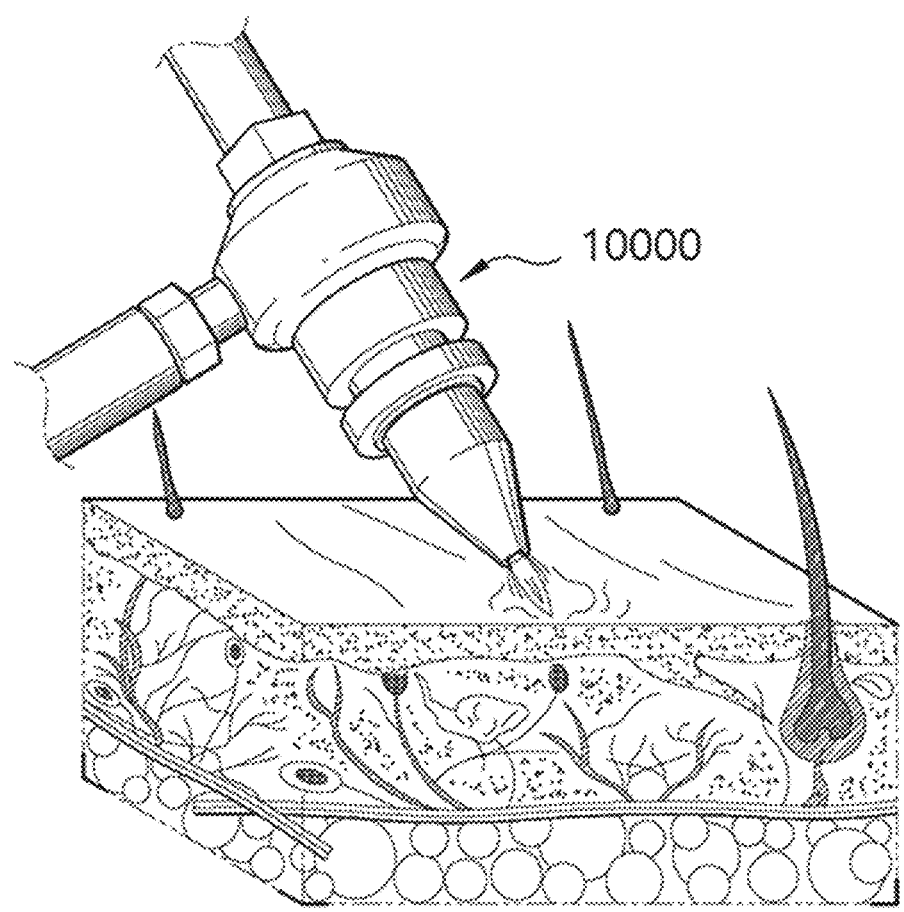
FIGS. 42, 43 and 44 and 45 are views for describing configurations of a heat providing barrier according to an embodiment of the present application.
Figure 43:
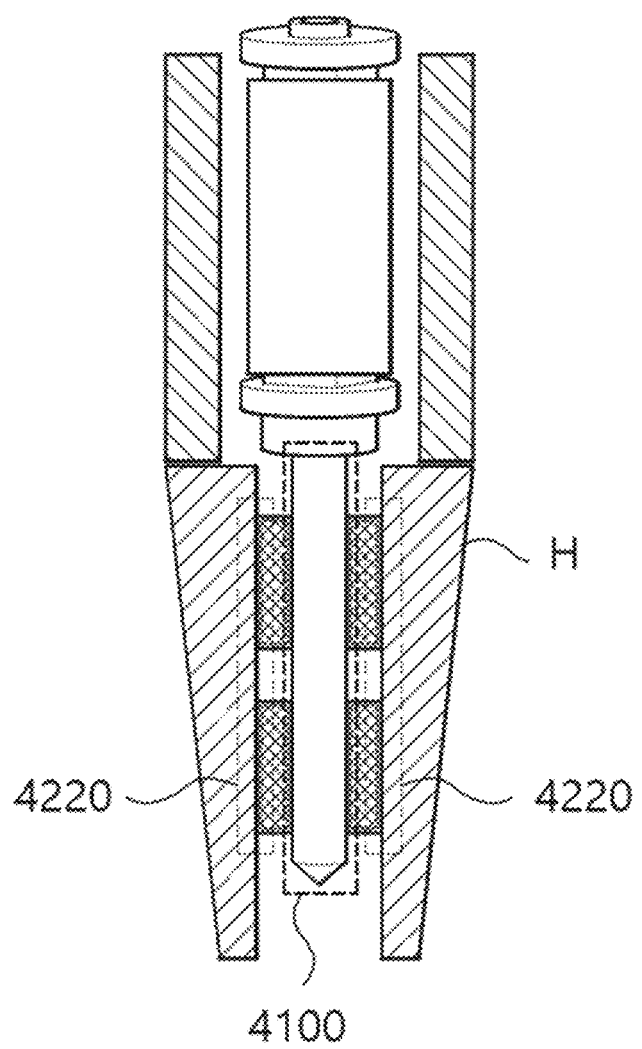

FIG. 42 is a view illustrating a use example of the cooling device 10000 according to an embodiment of the present application, and FIG. 43 is a view illustrating a configuration of the heat providing barrier 4220 according to an embodiment of the present application.

Referring to FIGS. 42 and 43, the nozzle unit 4100, which sprays the cryogen, and the heat providing barrier 4220 may be provided in a region of the spraying unit 4000 of the cooling device 10000 according to the described technology. Here, the heat providing barrier 4220 is a region other than the target region, i.e., the treatment site, and performs a function of supplying heat to the barrier of the treatment site in order to prevent the spread of cooling. Also, the heat providing barrier 4220 may further decrease the temperature of the center of the treatment site through the heat supplied to the barrier of the treatment site. In this way, there is an effect in that it is possible to realize a cooling temperature required for a treatment purpose at a deeper depth while destruction of normal cells surrounding the cells in lesions is minimized. Here, the heat supplied from the heat providing barrier 4220 allows the temperature of the surroundings of the treatment site to be kept at a temperature at which cryoanesthesia occurs. In this way, there is an effect in that, in addition to simply protecting the normal cells surrounding the cells in lesions, pain is minimized when removing the cells in lesions that are located in the center of the treatment site.

According to an embodiment, the heat providing barrier 4220 may be provided in a housing H of the spraying unit 4000. Methods of supplying heat from the heat providing barrier 4220 to a barrier portion of the target region TR include a first method in which the heat is provided through physical contact and a second method in which the heat is provided by a non-contact method through a separate gas or the like. The contact-type heat providing method will be described in detail with reference to FIG. 44, and the configuration of the non-contact type heat providing barrier will be described with reference to FIG. 45.

Here, the first method according to the described technology requires a separate outflow port 4166 to allow the cryogen to leak to the outside after coming into contact with the target region TR. The second method according to the described technology may, in addition to the nozzle unit 4100 for spraying the cryogen, further include another nozzle unit 4110 for spraying a gas for providing the heat.

The control unit according to the described technology may control heat applied to the heat providing barrier 4220. According to control of the control unit, the heat providing barrier 4220 of the medical cooling device may serve to supply heat at a predetermined temperature to the barrier of the target region TR.

Here, a differential heat transferring barrier 4265 such as a thermoelectric element for supplying heat is provided at an inner side of the heat providing barrier 4220. According to an embodiment, the differential heat transferring barrier 4265 may have one side thermally coupled with the heat providing barrier 4220 and the other surface thermally coupled to the nozzle unit 4100 so that the differential heat transferring barrier 4265 simultaneously performs heating of the heat providing barrier 4220 and cooling of the nozzle unit 4100. Here, the differential heat transferring barrier 4265 may be implemented as a thermoelectric element or the like.

According to the described technology, in a case in which the nozzle unit 4100 is cooled by the differential heat transferring barrier 4265, the temperature of the cryogen sprayed from the nozzle is controlled through contact with an inner surface of the nozzle unit 4100. That is, the cryogen sprayed from the nozzle is jetted to the outside as the cryogen flows through the nozzle unit 4100. Here, while the cryogen flows through the nozzle unit 4100, the temperature of the cryogen may be controlled through thermal contact or thermal exchange with the inner circumferential surface of the nozzle unit 4100. Through such a configuration, temperature control may be performed regarding the temperature of the target region TR and the barrier of the target region TR, and, by the heat providing barrier 4220, it is possible to prevent the cooling effect from spreading to a region outside the target region TR.

Figure 44:
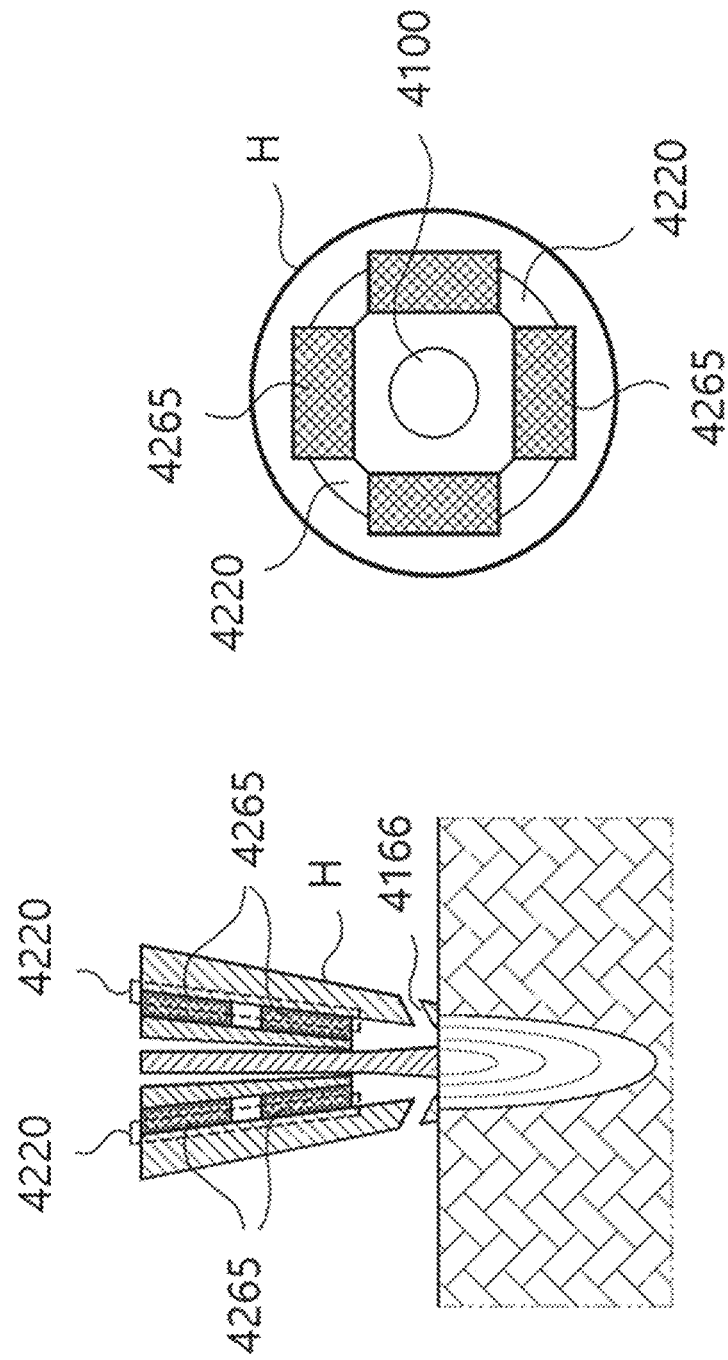

FIG. 44 is a view illustrating a configuration of the contact-type heat supplying method according to a preferred embodiment of the described technology.

The contact-type heat supplying method may include a first nozzle unit 4100, the differential heat transferring barrier 4265, and the heat providing barrier 4220.

A nozzle through which the flowed-in cryogen is sprayed to the outside through one side is provided in the first nozzle unit 4100. That is, the cryogen may be sprayed through the nozzle and cool the site subject to treatment.

According to an embodiment, the cryogen sprayed through the first nozzle unit 4100 may include at least liquid particles or gas particles. As the cryogen is sprayed through the nozzle of the first nozzle unit 4100, the temperature of the cryogen may decrease due to the Joule-Thomson effect, and the cryogen may cool a local site on the skin.

Also, the heat providing barrier 4220 is for minimizing damage to cells surrounding the treatment site and is provided along an outer surface of the first nozzle unit 4100. More specifically, the heat providing barrier may be thermally coupled to the first nozzle unit 4100 through a heat medium. i.e., the differential heat transferring barrier 4265.

According to an embodiment, the heat providing barrier 4220 may be formed of a material whose thermal conductivity is 10 W/m-K or higher. The heat providing barrier 4220 formed of such a material may, through coming into contact with the target region TR, transfer the heat received from the differential heat transferring barrier 4265 to the barrier of the target region TR. Here, instead of being formed of a thermoelectric element, the differential heat transferring barrier 4265 may also be formed of a nichrome wire or the like and thermally coupled to the heat providing barrier 4220.

According to an embodiment, the heat providing barrier 4220 may have an inverted conical shape provided along the outer circumferential surface of the first nozzle unit 4100. A movement space in which the cryogen flows may be formed in one side of the heat providing barrier 4220. The cryogen sprayed from the nozzle is sprayed to the skin along the movement space formed in the guide unit, and then the cryogen leaks to the outside through a cryogen outlet.

A barrier of the site subject to treatment is formed by the heat providing barrier 4220. In this way, movement of the cryogen to the outside of the site subject to treatment may be prevented. As the cryogen is induced to be intensively sprayed to the site subject to treatment, the efficiency and accuracy of cooling treatment may be improved such that the safety is improved.

Figure 45:
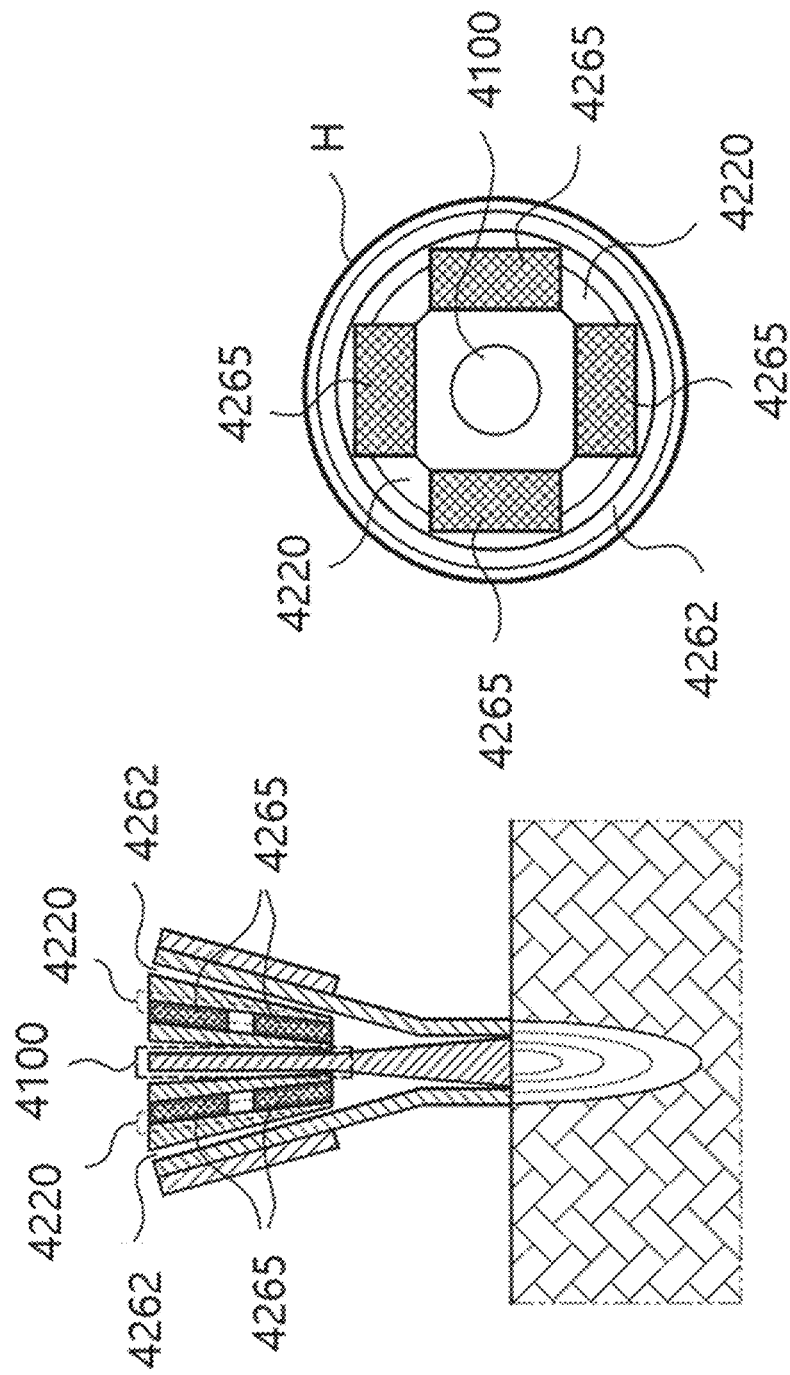

FIG. 45 is a view illustrating a configuration of the non-contact type heat providing barrier according to a preferred embodiment of the described technology.

The non-contact type heat providing barrier 4220 according to the described technology may spray a spraying material formed of gas to a barrier region, thereby simultaneously preventing the spread of cryogen and preventing the spread of the effect of cooling the treatment site to the outside of the barrier of the treatment site.

Referring to FIG. 45, the heat providing barrier 4220 may further include a fluid spraying unit 4262 configured to spray a fluid to the barrier of the target region, and heat may be supplied to the barrier of the target region by the fluid flowing through the fluid spraying unit 4262. Here, in the fluid spraying unit 4262, a plurality of heat dissipation fins may be formed for efficient heat transfer with the spraying material.

Here, the nozzle unit 4100 sprays the cryogen, and the fluid spraying unit 4262 sprays the spraying material. The nozzle unit 4100 may receive the cryogen from a cryogen tank accommodating the cryogen and spray the cryogen to a local treatment site to cool the skin. Here, preferably, the cryogen is $CO_2$, but is not limited thereto. Different types of cryogens may also be applied according to the purpose of treating the skin. Preferably, the cryogen is stored in the form of liquefied gas in the cryogen tank.

According to an embodiment, the spraying material may be the same as the cryogen or use a gaseous cryogen different from the cryogen. Even when a gaseous cryogen same as the cryogen is used as the spraying material, the cryogens may be stored in a single storage tank or separately stored in different storage tanks.

According to an embodiment of the described technology, the fluid spraying unit 4262 may be formed of a circumferential shape and spray the spraying material. An outer side portion of the fluid spraying unit 4262 may form a case, and an inner side portion of the fluid spraying unit 4262 may be thermally coupled with the differential heat transferring barrier 4265.

That is, a heat-generating surface of the differential heat transferring barrier 4265 may be thermally coupled to one surface of the inner circumferential portion of the fluid spraying unit 4262, and a cooling surface of the differential heat transferring barrier 4265 may be thermally coupled with one surface of the nozzle unit 4100. By such a configuration, through thermal contact with the inner side portion of the fluid spraying unit 4262, the spraying material moving through the fluid spraying unit 4262 may have an effect of receiving heat even while being sprayed.

According to an embodiment, by the cooling barrier, it is possible to prevent the spread of cooling energy to a region other than the treatment site while controlling the cooling temperature of the treatment site to a temperature range of −40° C. to 10° C.

Cooling Device 10000 According to Third Embodiment

Figure 46:
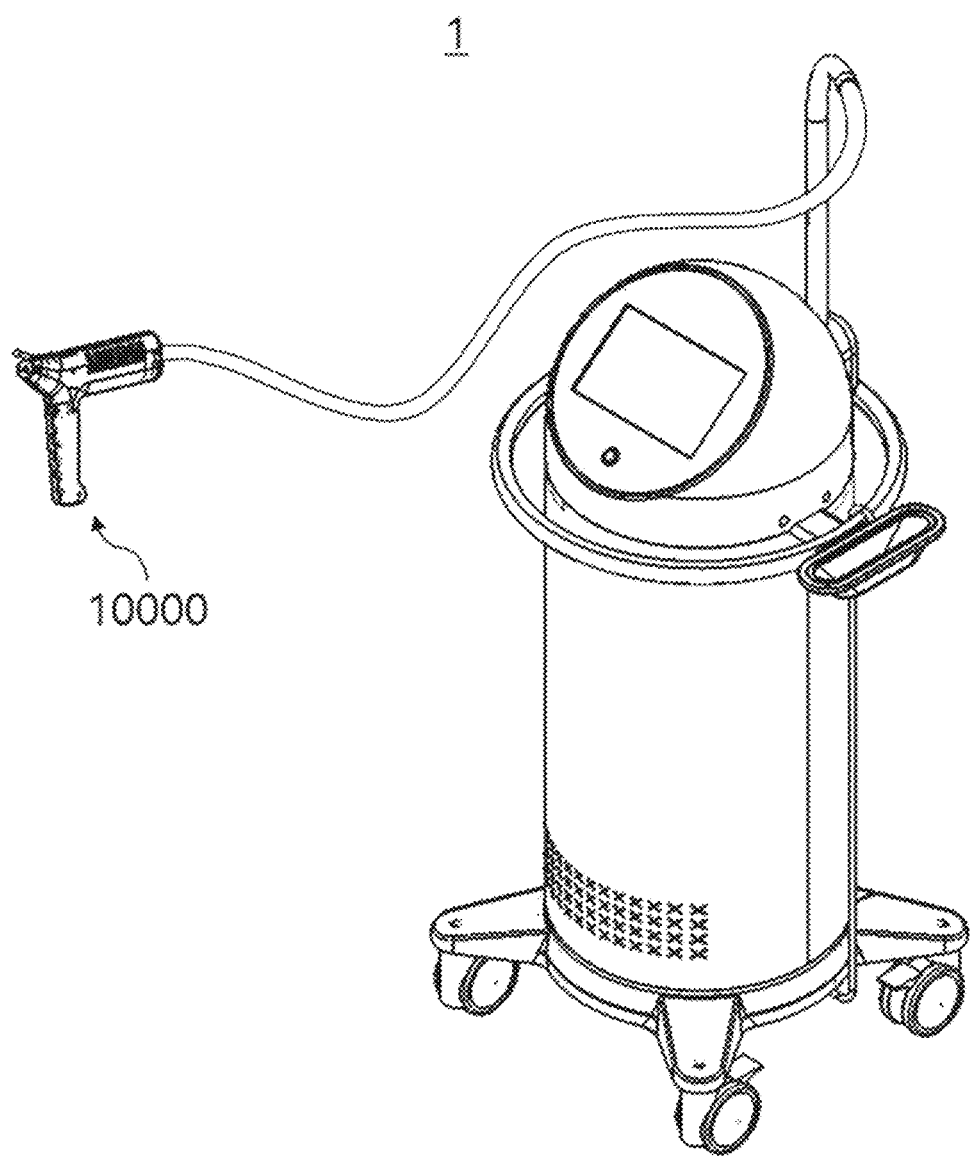
FIG. 46 is a view for describing a cooling system including a cooling device according to a third embodiment of the present application.

FIG. 46 is a view for describing a cooling system 1 including a cooling device 10000 according to a third embodiment of the present application.

The cooling device 10000 according to the third embodiment of the present application may include a cryogen supply unit 1000, a flow regulation unit 2000, a cryogen state regulation unit 3000, a spraying unit 4000, and a control unit 5000.

The cooling device 10000 according to the third embodiment of the present application may include a transfer unit 1200, a solenoid valve 2100, a cryogen cooling unit 3200, a spraying temperature controller 3100, a nozzle unit 4100, and the control unit 5000.

The cooling device 10000 according to the second embodiment of the present application may be the cooling device 10000 further including the cryogen cyclone rotator 3300 and the heat providing barrier 4220, as compared with the cooling device 10000 according to the third embodiment of the present application.

The cooling system 1 according to an embodiment of the present application may include the cooling device 10000, a hose connected to the cooling device 10000, and a cryogen storage tank.

Figure 47:
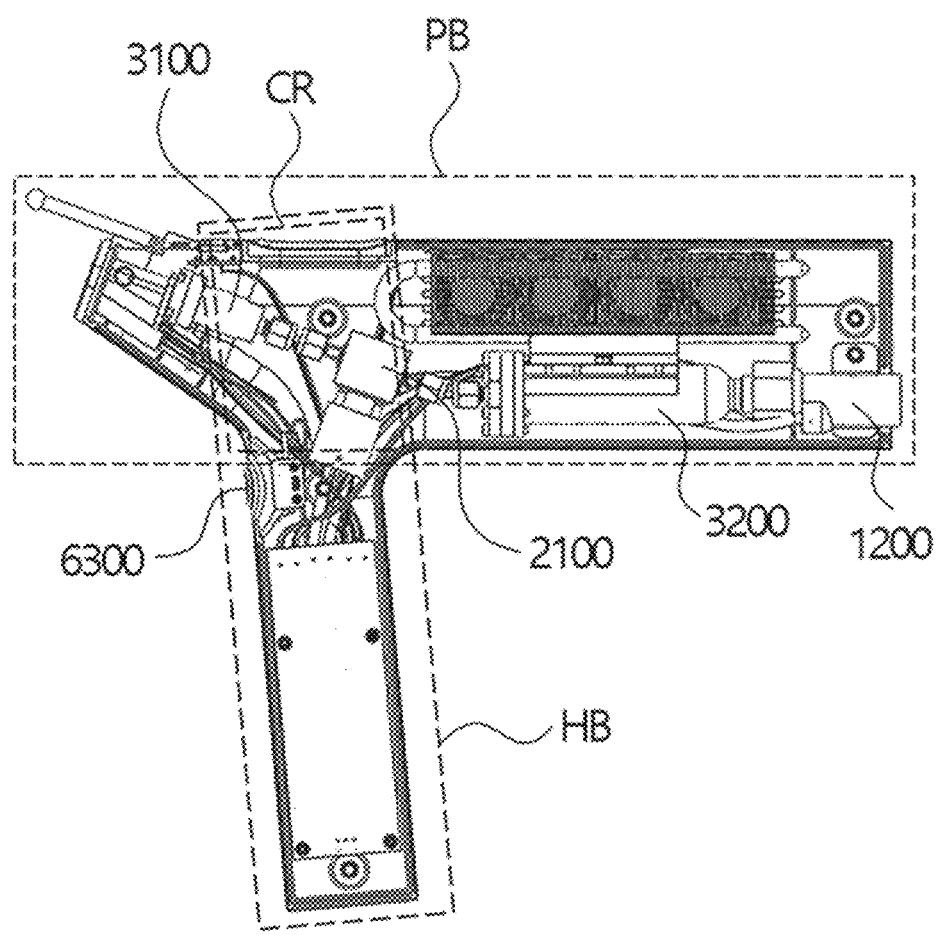
FIG. 47 is a cross-sectional view of the cooling device according to the third embodiment of the present application.

FIG. 47 is a cross-sectional view of the cooling device 10000 according to the third embodiment of the present application.

The cooling device 10000 may include the transfer unit 1200. The transfer unit 1200 may be an inflow port that receives the cryogen from the tank. As a specific example, the transfer unit 1200 may receive $CO_2$ from the cryogen storage tank accommodating $CO_2$ and transfer the received $CO_2$ to one element of the cooling device 10000.

The cooling device 10000 may include the cryogen cooling unit 3200. The cryogen cooling unit 3200 may change a state of the cryogen that passed through the transfer unit 1200. The cryogen cooling unit 3200 may perform a function of cooling the cryogen that passed through the transfer unit 1200.

The cooling device 10000 may include the solenoid valve 2100. The solenoid valve 2100 may perform discharge of a fluid and blockage of the discharge of the fluid in response to an electrical signal. As a more specific example, the solenoid valve 2100 may include an inlet into which the fluid flows, an outlet from which the fluid discharges, a plunger configured to reciprocate to block a flow of the fluid, and an armature configured to generate an induced magnetic force.

In response to an electrical signal applied thereto, the solenoid valve 2100 may generate an electromagnetic force at the armature and change the plunger to an open state. The solenoid valve 2100 may remove the electromagnetic force generated at the armature and change the plunger to a closed state.

As described in detail above regarding the cooling device 10000 according to the second embodiment, the cryogen cooling unit 3200 may include a reservoir configured to accommodate the cryogen, a cooling element configured to cool the reservoir, and a heat dissipater configured to dissipate heat generated in the cooling element.

The cryogen cooling unit 3200 may be connected to the transfer unit 1200 through a first flow path. The first flow path may perform a function of transferring the cryogen from the transfer unit 1200 to the cryogen cooling unit 3200.

The cryogen cooling unit 3200 may be connected to the inlet of the solenoid valve 2100 through a second flow path. The second flow path may perform a function of transferring the cryogen from the cryogen cooling unit 3200 to the inlet of the solenoid valve 2100.

The cryogen cooling unit 3200 may cool the cryogen in the cryogen cooling unit 3200 so as to increase a proportion of liquid phase in the cryogen in the second flow path more than a proportion of liquid phase in the cryogen in the first flow path. The cryogen cooling unit 3200 may cool the cryogen in the reservoir of the cryogen cooling unit 3200.

The cooling device 10000 may include the nozzle unit 4100. The nozzle unit 4100 may be provided in the form in which a cross-sectional area of a first end is different from a cross-sectional area of a second end. The nozzle unit 4100 may be provided in the form in which the cross-sectional area of the first end, which is relatively more spaced apart from the transfer unit 1200, is smaller than the second cross-sectional area. Here, because of the phenomenon in which, due to the decrease of the cross-sectional area at the first end, the pressure increases and the pressure energy changes to speed energy, the nozzle unit 4100 may perform a function of allowing the cryogen to spray to the outside of the cooling device 10000.

As described in detail above regarding the cooling device 10000 according to the second embodiment, the spraying temperature controller 3100 may include a flow path through which cryogen may move and a heating element disposed around the flow path and configured to control the temperature of the cryogen in the flow path.

According to an embodiment of the present application, the heating element may be a thermoelectric element. The thermoelectric element may include a first side thermally connected to the cryogen and configured to heat the cryogen and a second side configured to perform an endothermic reaction according to an exothermic reaction of the first side. Here, the first side may be disposed more adjacent to the nozzle unit 4100 than the second side. In other words, the first side may be disposed more adjacent to the fluid moved by the cryogen than the second side.

The spraying temperature controller 3100 may be connected to the outlet of the solenoid valve 2100 through a third flow path. The third flow path may perform a function of transferring the cryogen from the outlet of the solenoid valve 2100 to a flow path in the spraying temperature controller 3100.

The spraying temperature controller 3100 may be connected to one end of the nozzle unit 4100 through a fourth flow path. The fourth flow path may perform a function of transferring the cryogen, which passed through the spraying temperature controller 3100, to the other end of the nozzle unit 4100. Here, the other end of the nozzle unit 4100 may be formed at an outer side of the housing of the cooling device 10000.

The cooling device 10000 may include at least one pipe. The pipe may be used in forming a flow path so that the cryogen, which is transferred from the transfer unit 1200 in the cooling device 10000, sprays to the outside through the nozzle unit 4100.

The cooling device 10000 may include a pipe that involves in forming a flow path used in moving the cryogen to the solenoid valve 2100 from the transfer unit 1200 via the cryogen cooling unit 3200. At least one pipe may be disposed between the transfer unit 1200 and the inlet of the solenoid valve 2100.

In a case in which a plurality of pipes are disposed between the transfer unit 1200 and the inlet of the solenoid valve 2100, a first pipe and a second pipe may be connected in a form that does not cause much leakage of cryogen and form a flow path. As a specific example, the first pipe and the second pipe may be connected in the form of being fitted and coupled.

The cooling device 10000 may include a pipe that involves in forming a flow path used in moving the cryogen to a cryogen discharge port of the nozzle unit 4100 from the outlet of the solenoid valve 2100 via the spraying temperature controller 3100.

In a case in which a plurality of pipes are disposed between the outlet of the solenoid valve 2100 and the cryogen discharge port of the nozzle unit 4100, a third pipe and a fourth pipe may be connected in a form that does not cause much leakage of cryogen and form a flow path. As a specific example, the third pipe and the fourth pipe may be connected in the form of being fitted and coupled.

The cooling device 10000 may further include a filter 6200 for filtering impurities from a cryogen flowing in the cooling device 10000. The filter 6200 may be installed in at least one region of the flow path through which the cryogen flows in the cooling device 10000. The filter $62(x)$ may have a form corresponding to a cross-sectional shape of a pipe. The filter 6200 may be formed of a porous material. The filter 6200 may be formed of a hydrophobic material.

The cooling system 1 may further include an input unit 6300. The input unit 6300 may acquire a signal corresponding to a user input. The input unit 6300 may be implemented using a keyboard, a keypad, a button, a jog/shuttle, a wheel, and the like. The input unit 6300 may be a key pad utilized as a switch.

The input unit 6300 may be included in the cooling device 10000 according to the third embodiment of the present application. The input unit 6300 may be formed in a main body that is separately present outside the cooling device 10000. Here, the main body may be electrically connected with the cooling device 10000 and control the cooling device 10000 on the basis of information input through the input unit 6300.

The cooling device 10000 according to the third embodiment of the present application may include a switch which generates an electrical signal in response to user contact. The switch may perform a function of generating an electrical signal in response to generation of an electrostatic signal according to user contact. Alternatively, the switch may perform a function of generating an electrical signal in response to generation of a pressure of a predetermined numerical value or higher according to user contact.

The cooling system 1 may include the control unit 5000. The cooling system 1 may include a controller. The controller may generate a control signal for controlling the on/off and/or the opening/closing amount of the solenoid valve 2100 and transmit the generated control signal to the solenoid valve 2100. The controller may generate a control signal for controlling the on/off of and/or the amount of current applied to a cooling element of the cryogen cooling unit 3200 and transmit the generated control signal to the cooling element. The controller may generate a control signal for controlling the on/off of and/or the amount of current applied to a heating element of the spraying temperature controller 3100 and transmit the generated control signal to the heating element.

The controller may be included in the cooling device 10000 according to the third embodiment of the present application. The controller formed in a main body that is separately present outside the cooling device 10000. Here, the main body may be electrically connected with the cooling device 10000 and perform a function of providing the control signal generated by the controller to at least one region of the cooling device 10000.

The cooling system 1 may further include a power supply unit. The cooling system 1 may further include a power supply unit which supplies power for driving the cooling device 10000. The power supply unit may include at least one of a direct-current power source for supplying direct current and an alternating-current power source for supplying alternating current. For example, the power supply unit may be in the form of a battery or a dry cell. As another example, the power supply unit may be in the form of a power line that receives power.

The power supply unit may be included in the cooling device 10000 according to the third embodiment of the present application. The power supply unit may be formed in a main body that is separately present outside the cooling device 10000. Here, the main body may be electrically connected with the cooling device 10000 and perform a function of providing the power input through the power supply unit to at least one region of the cooling device 10000.

The power supply unit may supply power to the control unit 5000. The power supply unit may supply power to the solenoid valve 2100. The power supply unit may supply power for controlling the opening and closing of the solenoid valve 2100.

The cooling system 1 may include a sensor for measuring the amount of cryogen remaining in the reservoir 1100. As a specific example, the sensor may measure a weight of the reservoir 1100 and measure the amount of cryogen remaining therein.

The cooling system 1 may include a sensor for measuring a temperature of the target region TR. The sensor for measuring the temperature of the target region TR may be a non-contact type temperature sensor. According to an embodiment of the present application, the cooling system 1 may further include an independent sensor to verify the sensor for measuring the temperature of the target region TR that is included in the cooling device 100M. The sensor that verifies the sensor measuring the temperature of the target region TR may be a non-contact type temperature sensor. As a specific example, the cooling system 1 may include a first infrared temperature sensor and a second infrared temperature sensor. The first infrared temperature sensor may be a sensor for measuring the temperature of the target region TR. The second infrared temperature sensor may be a temperature sensor for verifying the first infrared temperature sensor. In a case in which a first value is measured from the first infrared temperature sensor and a second value is measured from the second infrared temperature sensor, the control unit 5000 may compare the first value and the second value. By comparing the first value and the second value, the control unit 5000 may check whether the first infrared temperature sensor operates normally.

The cooling device 10000 according to the third embodiment of the present application may have a T-shaped body. The cooling device 10000 may have a T-shaped body including a horizontal body PB and a hand body HB.

The hand body HB may be spaced a predetermined distance apart from a front end of the horizontal body PB. The hand body HB may be integrally formed to have a predetermined angle with the horizontal body PB.

According to an embodiment of the present application, the transfer unit 1200 may be disposed at one end of the horizontal body PB (hereinafter referred to as a rear end of the horizontal body PB). The nozzle unit 4100 may be disposed at the other end of the horizontal body PB (hereinafter referred to as the front end of the horizontal body PB).

The inlet of the solenoid valve 2100 may be disposed at the rear end of the horizontal body PB. A flow path through which a fluid may move may be formed between the inlet of the solenoid valve 2100 and the transfer unit 1200, and the flow path may be disposed at the rear end of the horizontal body PB. The cryogen cooling unit 3200 may be disposed between the inlet of the solenoid valve 2100 and the transfer unit 1200, and the cryogen cooling unit 3200 may be disposed at the rear end of the horizontal body HB.

In a case in which the cryogen cooling unit 3200 includes a heat sink, the heat sink may be disposed at the rear end of the horizontal body PB. The heat sink may perform a function of dissipating heat generated according to an operation of a cooling element of the cryogen cooling unit 3200. Here, the heat from the cryogen supply unit 1000 may also be dissipated together from the heat sink.

The outlet of the solenoid valve 2100 may be disposed at the front end of the horizontal body PB. A flow path through which a fluid may move may be formed between the outlet of the solenoid valve 2100 and the nozzle unit 4100, and the flow path may be disposed at the front end of the horizontal body PB. The spraying temperature controller 3100 may be disposed between the outlet of the solenoid valve 2100 and the nozzle unit 4100, and the spraying temperature controller 3100 may be disposed at the front end of the horizontal body PB.

According to circumstances, the power supply unit may be disposed at the hand body PB. The input unit 6300 may be disposed at the hand body HB. The control unit 5000 may be disposed at the hand body HB.

The valve 2100 may be disposed in a region CR in which the horizontal body PB and the hand body HB are connected. According to circumstances, the armature of the solenoid valve 2100 may be disposed at an upper end of the hand body HB.

The flow path through which a fluid may move between the outlet of the solenoid valve 2100 and the nozzle unit 4100 may be formed in a second direction, which is parallel to or the same as a first direction in which the flow path through which a fluid may move between the inlet of the solenoid valve 2100 and the reservoir 1100 is formed.

The plunger may reciprocate between the inlet of the solenoid valve 2100 and the reservoir 1100 in a third direction, which is a direction perpendicular to the first direction in which the flow path through which a fluid may move is formed.

The cooling device 10000 according to another embodiment of the present application may be implemented in the form in which the transfer unit 1200 is disposed at the hand body HB and the power supply unit is disposed at the rear end of the horizontal body PB.

The valve 2100 may be disposed in the region CR in which the horizontal body PB and the hand body HB are connected. According to circumstances, the armature of the solenoid valve 2100 may be disposed at the rear end of the horizontal body PB.

The structure of the cooling device 10000 according to the third embodiment has been described above with reference to some embodiments.

However, the design of the structure of the cooling device 10000 may be easily changed according to user convenience and the need of a producer, and the scope of the present application is not limited to the above-described embodiment.

The cooling device 10000 according to the third embodiment of the present application may perform the above-described cooling control, dynamic cooling control, provision of vibration, cryogen spraying uniformity control, driving control of the cooling device 10000, and/or control for preventing an excessive temperature rise.

Specific operations in which the cooling device 10000 according to the third embodiment performs the cooling control, the dynamic cooling control, the provision of vibration, the cryogen spraying uniformity control, the driving control of the cooling device 10000, and/or the control for preventing an excessive temperature rise have been described in detail above, and thus detailed descriptions thereof will be omitted.

The configurations and characteristics of the present application have been described above on the basis of the embodiments according to the present application, but the present application is not limited thereto. It should be apparent to those of ordinary skill in the art to which the present application pertains that various changes or modifications may be made within the idea and scope of the present application. Note that such changes or modifications also belong to the scope of the appended claims.

What is claimed is:

1. A hand-held cooling device for supplying a cryogen to a target region for cryotherapy, the hand-held cooling device comprising:
a cryogen container configured to contain a first cryogen;
a nozzle configured to spray a first modified cryogen to the target region;
a valve disposed between the cryogen container and the nozzle and configured to regulate a flow of the first cryogen; and
a cryogen temperature regulator disposed between the nozzle and the valve and configured to receive the first cryogen from the valve and output the first modified cryogen to the nozzle,
wherein the cryogen temperature regulator comprises:
a holder tube disposed between the valve and the nozzle and configured to receive the first cryogen from the valve via a first end thereof and output the first modified cryogen to the nozzle via a second end thereof;
a porous structure disposed inside the holder tube and configured to receive the first cryogen, having a first temperature, from the valve and output the first modified cryogen, having a second temperature higher than the first temperature, toward the nozzle; and
a heater disposed around an outer circumferential surface of the holder tube and configured to apply heat to the holder tube.

2. The hand-held cooling device according to claim 1, wherein the heater is configured to increase the first temperature of the first cryogen to the second temperature of the first modified cryogen while the first cryogen passes through the porous structure such that the first modified cryogen having the second temperature is output from the holder tube toward the nozzle.

3. The hand-held cooling device according to claim 1, wherein the holder tube comprises a plurality of binding fixing surfaces disposed radially or symmetrically about a central axis thereof, and wherein the heater comprises a plurality of heating elements respectively fixed to the plurality of binding fixing surfaces.

4. The hand-held cooling device according to claim 1, wherein at least a portion of the porous structure is in direct physical contact with an inner wall of the holder tube, and wherein the porous structure extends from the first end of the holder tube to a region in the inner wall of the holder tube adjacent to the second end of the holder tube.

5. The hand-held cooling device according to claim 1, wherein the heater is in direct physical contact with the outer circumferential surface of the holder tube, and wherein the heater substantially axially overlaps the porous structure.

6. The hand-held cooling device according to claim 1, wherein the cryogen temperature regulator further comprises:
a first insulating member coupled to the first end of the holder tube and configured to thermally insulate the holder tube from the cryogen container and the valve; and
a second insulating member disposed between the second end of the holder tube and the nozzle and configured to thermally insulate the holder tube from the nozzle.

7. The hand-held cooling device according to claim 6, wherein the first insulating member is disposed around and in direct physical contact with an outer surface of the first end of the holder tube, and wherein the second insulating member is disposed around and in direct physical contact with an outer surface of the second end of the holder tube.

8. The hand-held cooling device according to claim 1, wherein the holder tube is longer than the porous structure and the heater, and wherein the porous structure is longer than the heater.

9. The hand-held cooling device according to claim 1, wherein the first modified cryogen has a pressure higher than that of the first cryogen.

10. The hand-held cooling device according to claim 1, wherein the porous structure comprises a sintered metal structure having thermal conductivity, the sintered metal structure configured to be heated by the heater and subsequently heat the first cryogen to increase the first temperature of the first cryogen to the second temperature of the first modified cryogen.

11. The hand-held cooling device according to claim 1, further comprising a main controller configured to control closing and opening operations of the valve and activating and deactivating operations of the cryogen temperature regulator.

12. The hand-held cooling device according to claim 11, wherein the main controller is configured to deactivate the cryogen temperature regulator before closing the valve so as to cool the cryogen temperature regulator.

13. The hand-held cooling device according to claim 12, wherein the main controller is further configured to control the valve and the cryogen temperature regulator such that the cryogen temperature regulator outputs a second modified cryogen to the nozzle after the cryogen temperature regulator is deactivated, the second modified cryogen having a third temperature not higher than the second temperature.

14. The hand-held cooling device according to claim 12, wherein the main controller is further configured to transmit a pulse signal for opening or closing the valve, and within a predetermined time from when a transmission of the pulse signal terminates, to transmit a signal for deactivating the cryogen temperature regulator.

15. The hand-held cooling device according to claim 1, further comprising:
a cryogen cooler configured to receive the first cryogen from the cryogen container and maintain a pressure of the first cryogen at a predetermined pressure; and
a power supply configured to supply power to at least one of the valve or the cryogen temperature regulator.

16. The hand-held cooling device according to claim 15, further comprising:
an upper body; and
a hand body spaced apart from a front end of the upper body by a predetermined distance and integrally formed to have a predetermined angle with the upper body,
wherein the cryogen cooler is disposed at a rear end of the upper body,
wherein the nozzle is disposed at the front end of the upper body, and wherein the power supply is disposed in the hand body.

17. A hand-held cooling device for supplying a cryogen to a target region for cryotherapy, the hand-held cooling device comprising:
a cryogen container configured to contain a first cryogen;
a nozzle configured to spray a first modified cryogen to the target region;

a valve disposed between the cryogen container and the nozzle and configured to regulate a flow of the first cryogen; and a cryogen temperature regulator disposed between the nozzle and the valve and configured to receive the first cryogen from the valve and output the first modified cryogen to the nozzle, wherein the cryogen temperature regulator comprises:
  a holder tube disposed between the valve and the nozzle; and
  a porous structure disposed inside the holder tube and comprising a thermally conductive material, the porous structure configured to receive the first cryogen, having a first temperature, from the valve and pass the received first cryogen therethrough while allowing the first cryogen to exchange heat with the thermally conductive material so as to output the first modified cryogen having a second temperature higher than the first temperature.

18. The hand-held cooling device according to claim 17, further comprising a heater disposed around an outer circumferential surface of the holder tube and configured to apply heat to the holder tube so as to heat the thermally conductive material of the porous structure.

19. The hand-held cooling device according to claim 18, wherein the heater is configured to increase the first temperature of the first cryogen to the second temperature of the first modified cryogen while the first cryogen passes through the porous structure such that the first modified cryogen having the second temperature is output from the holder tube to the nozzle.

20. The hand-held cooling device according to claim 17, wherein the cryogen temperature regulator further comprises:
  a first insulating member coupled to a first end of the holder tube and configured to thermally insulate the holder tube from the cryogen container and the valve; and
  a second insulating member disposed between a second end of the holder tube and the nozzle and configured to thermally insulate the holder tube from the nozzle, wherein the second end of the holder tube is opposing the first end of the holder tube, and wherein the second end of the holder tube is closer to the nozzle than the first end of the holder tube.

* * * * *